United States Patent
Njar et al.

(10) Patent No.: US 9,387,216 B2
(45) Date of Patent: *Jul. 12, 2016

(54) BIOMARKERS FOR TREATMENT OF NEOPLASTIC DISORDERS USING ANDROGEN-TARGETED THERAPIES

(71) Applicants: Tokai Pharmaceuticals, Inc., Boston, MA (US); University of Washington, Seattle, WA (US); University of Maryland, Baltimore, Baltimore, MD (US)

(72) Inventors: Vincent C. O. Njar, Glen Burnie, MD (US); Amina Zoubeidi, Vancouver (CA); Karen Ferrante, Boston, MA (US); Eva Corey, Seattle, WA (US); Douglas B. Jacoby, Wellesley, MA (US)

(73) Assignees: Tokai Pharmaceuticals, Inc., Boston, MA (US); University of Washington, Seattle, WA (US); University of Maryland, Baltimore, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/792,490

(22) Filed: Jul. 6, 2015

(65) Prior Publication Data

US 2015/0374721 A1 Dec. 31, 2015

Related U.S. Application Data

(63) Continuation of application No. 14/758,938, filed as application No. PCT/US2014/050793 on Aug. 12, 2014.

(60) Provisional application No. 61/865,038, filed on Aug. 12, 2013, provisional application No. 61/990,570, filed on May 8, 2014, provisional application No. 62/002,110, filed on May 22, 2014.

(51) Int. Cl.
*A61K 31/58* (2006.01)
*C07J 43/00* (2006.01)
*C12Q 1/68* (2006.01)

(52) U.S. Cl.
CPC .............. *A61K 31/58* (2013.01); *C07J 43/003* (2013.01); *C12Q 1/6886* (2013.01); *C12Q 2600/156* (2013.01); *C12Q 2600/158* (2013.01)

(58) Field of Classification Search
CPC ..................................................... A61K 31/58
USPC ........................................................ 514/394
See application file for complete search history.

(56) References Cited

U.S. PATENT DOCUMENTS

| | | | |
|---|---|---|---|
| 2,664,423 | A | 12/1953 | Rorig |
| 3,060,174 | A | 10/1962 | Albert et al. |
| 3,313,809 | A | 4/1967 | Clinton et al. |
| 3,317,520 | A | 5/1967 | Clinton |
| 3,480,621 | A | 11/1969 | Loken et al. |
| 3,539,687 | A | 11/1970 | Kuhnen et al. |
| 4,000,125 | A | 12/1976 | Casagrande et al. |
| 4,316,885 | A | 2/1982 | Rakhit |
| 4,650,803 | A | 3/1987 | Stella et al. |
| 5,023,263 | A | 6/1991 | Von Burg |
| 5,023,264 | A | 6/1991 | Caufield et al. |
| 5,028,726 | A | 7/1991 | Farrell |
| 5,100,883 | A | 3/1992 | Schiehser |
| 5,104,895 | A | 4/1992 | Spinelli et al. |
| 5,118,677 | A | 6/1992 | Caufield |
| 5,118,678 | A | 6/1992 | Kao et al. |
| 5,120,842 | A | 6/1992 | Failli et al. |
| 5,151,413 | A | 9/1992 | Caufield et al. |
| 5,162,333 | A | 11/1992 | Failli et al. |
| 5,177,203 | A | 1/1993 | Failli et al. |
| 5,221,670 | A | 6/1993 | Caufield |
| 5,232,917 | A | 8/1993 | Bolger et al. |
| 5,233,036 | A | 8/1993 | Hughes |
| 5,237,064 | A | 8/1993 | Bakshi et al. |
| 5,256,790 | A | 10/1993 | Nelson |
| 5,258,389 | A | 11/1993 | Goulet et al. |
| 5,260,300 | A | 11/1993 | Hu |
| 5,262,423 | A | 11/1993 | Kao |
| 5,264,427 | A | 11/1993 | Brodie et al. |
| 5,270,163 | A | 12/1993 | Gold et al. |
| 5,300,294 | A | 4/1994 | Johnson |
| 5,302,584 | A | 4/1994 | Kao et al. |
| 5,362,718 | A | 11/1994 | Skotnicki et al. |
| 5,373,014 | A | 12/1994 | Failli et al. |

(Continued)

FOREIGN PATENT DOCUMENTS

| CN | 101023349 A | 8/2007 |
|---|---|---|
| EP | 0469548 A2 | 2/1992 |

(Continued)

OTHER PUBLICATIONS

Ferraldeschi et al., The Cancer J., vol. 19(1), Jan./Feb. 2013.*

(Continued)

*Primary Examiner* — Taofiq A Solola

(74) *Attorney, Agent, or Firm* — Choate, Hall & Stewart LLP; Brenda Herschbach Jarrell

(57) ABSTRACT

Described herein are methods and compositions for the treatment of prostate cancer in a subject in need thereof. The prostate cancer may be a castration resistant and an androgen receptor antagonist-resistant prostate cancer. The methods may comprise administering to the subject a CYP17-lyase inhibitor of Formula II.

30 Claims, 24 Drawing Sheets

(56) References Cited

U.S. PATENT DOCUMENTS

| | | | |
|---|---|---|---|
| 5,378,836 A | 1/1995 | Kao et al. |
| 5,385,908 A | 1/1995 | Nelson et al. |
| 5,385,909 A | 1/1995 | Nelson et al. |
| 5,385,910 A | 1/1995 | Ocain et al. |
| 5,385,936 A | 1/1995 | Flack et al. |
| 5,389,639 A | 2/1995 | Failli et al. |
| 5,391,730 A | 2/1995 | Skotnicki et al. |
| 5,411,967 A | 5/1995 | Kao et al. |
| 5,434,260 A | 7/1995 | Skotnicki et al. |
| 5,456,923 A | 10/1995 | Nakamichi et al. |
| 5,463,048 A | 10/1995 | Skotnicki et al. |
| 5,475,096 A | 12/1995 | Gold et al. |
| 5,480,988 A | 1/1996 | Failli et al. |
| 5,480,989 A | 1/1996 | Kao et al. |
| 5,489,680 A | 2/1996 | Failli et al. |
| 5,491,231 A | 2/1996 | Nelson et al. |
| 5,496,556 A | 3/1996 | Johnson |
| 5,504,091 A | 4/1996 | Molnar-Kimber et al. |
| 5,512,570 A | 4/1996 | Dorn et al. |
| 5,563,145 A | 10/1996 | Failli et al. |
| 5,567,588 A | 10/1996 | Gold et al. |
| 5,595,877 A | 1/1997 | Gold et al. |
| 5,601,981 A | 2/1997 | Malins |
| 5,604,213 A | 2/1997 | Barrie et al. |
| 5,620,986 A | 4/1997 | Witzel et al. |
| 5,637,310 A | 6/1997 | Johnson |
| 5,637,459 A | 6/1997 | Burke et al. |
| 5,660,985 A | 8/1997 | Pieken et al. |
| 5,665,772 A | 9/1997 | Cottens et al. |
| 5,670,637 A | 9/1997 | Gold et al. |
| 5,672,605 A | 9/1997 | Or et al. |
| 5,683,867 A | 11/1997 | Biesecker et al. |
| 5,696,249 A | 12/1997 | Gold et al. |
| 5,707,796 A | 1/1998 | Gold et al. |
| 5,721,227 A | 2/1998 | Melloni et al. |
| 5,741,795 A | 4/1998 | Aster et al. |
| 5,780,462 A | 7/1998 | Lee et al. |
| 5,994,334 A | 11/1999 | Brodie et al. |
| 5,994,335 A | 11/1999 | Brodie et al. |
| 6,011,020 A | 1/2000 | Gold et al. |
| 6,133,280 A | 10/2000 | Brodie et al. |
| 6,200,965 B1 | 3/2001 | Brodie et al. |
| 6,368,598 B1 | 4/2002 | D'Amico et al. |
| 6,444,649 B1 | 9/2002 | Inamori et al. |
| 6,444,683 B2 | 9/2002 | Brodie et al. |
| 6,548,555 B1 | 4/2003 | Curatolo et al. |
| 6,763,607 B2 | 7/2004 | Dobry et al. |
| 6,933,312 B2 | 8/2005 | Price et al. |
| 6,960,584 B2 | 11/2005 | Carling et al. |
| 6,973,741 B2 | 12/2005 | Beyerinck et al. |
| 6,982,258 B2 | 1/2006 | Posner et al. |
| 7,098,208 B2 | 8/2006 | Owens et al. |
| 7,192,974 B2 | 3/2007 | Gravestock et al. |
| 7,223,738 B2 | 5/2007 | Bilodeau et al. |
| 7,304,063 B2 | 12/2007 | Bilodeau et al. |
| 7,378,403 B2 | 5/2008 | Kozikowski et al. |
| 7,396,832 B2 | 7/2008 | Lindsley et al. |
| 7,399,764 B2 | 7/2008 | Duggan et al. |
| 7,414,055 B2 | 8/2008 | Duggan et al. |
| 7,544,677 B2 | 6/2009 | Bilodeau et al. |
| 7,576,209 B2 | 8/2009 | Kelly et al. |
| 7,579,355 B2 | 8/2009 | Bilodeau et al. |
| 7,589,068 B2 | 9/2009 | Cosford et al. |
| 7,604,947 B2 | 10/2009 | Gudas |
| 7,638,530 B2 | 12/2009 | Bilodeau et al. |
| 7,655,649 B2 | 2/2010 | Bilodeau et al. |
| 7,705,014 B2 | 4/2010 | Chen et al. |
| 7,750,151 B2 | 7/2010 | Bilodeau et al. |
| 7,780,988 B2 | 8/2010 | Beyerinck et al. |
| 7,807,393 B2 | 10/2010 | Thaxton et al. |
| 7,875,599 B2 * | 1/2011 | Brodie .................. C07J 43/003 514/176 |
| 7,887,840 B2 | 2/2011 | Curatolo et al. |
| 7,943,732 B2 | 5/2011 | Reed |
| 7,960,435 B2 | 6/2011 | Njar et al. |
| 8,003,643 B2 | 8/2011 | Bilodeau et al. |
| 8,003,651 B2 | 8/2011 | Mitchell et al. |
| 8,008,317 B2 | 8/2011 | Armstrong et al. |
| 8,026,286 B2 | 9/2011 | Curatolo et al. |
| 8,110,550 B2 | 2/2012 | Brodie et al. |
| 8,129,184 B2 | 3/2012 | Yu |
| 8,133,724 B2 | 3/2012 | Qiu et al. |
| 8,168,652 B2 | 5/2012 | Sanderson et al. |
| 8,263,357 B2 | 9/2012 | Reed |
| 8,273,782 B2 | 9/2012 | Seefeld et al. |
| 8,324,221 B2 | 12/2012 | Banka et al. |
| 8,785,423 B2 | 7/2014 | Njar et al. |
| 8,791,094 B2 | 7/2014 | Morrison et al. |
| 8,791,095 B2 | 7/2014 | Casebier |
| 8,822,438 B2 | 9/2014 | Auerbach et al. |
| 8,841,422 B2 | 9/2014 | Qiu et al. |
| 9,018,198 B2 | 4/2015 | Njar et al. |
| 9,156,878 B2 | 10/2015 | Morrison et al. |
| 2001/0001099 A1 | 5/2001 | Brodie et al. |
| 2002/0009494 A1 | 1/2002 | Curatolo et al. |
| 2003/0054053 A1 | 3/2003 | Young et al. |
| 2003/0059471 A1 | 3/2003 | Compton et al. |
| 2004/0058896 A1 | 3/2004 | Dietrich et al. |
| 2006/0013873 A1 | 1/2006 | Yang et al. |
| 2007/0037887 A1 | 2/2007 | Santen et al. |
| 2007/0185152 A1 | 8/2007 | Yamashita et al. |
| 2007/0238647 A1 | 10/2007 | Bowen et al. |
| 2008/0058301 A1 | 3/2008 | Lardy et al. |
| 2008/0280864 A1 | 11/2008 | Brodie et al. |
| 2009/0012045 A1 | 1/2009 | Hitoshi et al. |
| 2009/0047252 A1 | 2/2009 | Cai et al. |
| 2009/0048149 A1 | 2/2009 | Ng et al. |
| 2009/0221672 A1 | 9/2009 | Zhang et al. |
| 2010/0009397 A1 | 1/2010 | Sebti et al. |
| 2010/0029667 A1 | 2/2010 | Ketner et al. |
| 2010/0047338 A1 | 2/2010 | Brodie et al. |
| 2010/0048524 A1 | 2/2010 | Brodie et al. |
| 2010/0048912 A1 | 2/2010 | Brodie et al. |
| 2010/0048913 A1 | 2/2010 | Brodie et al. |
| 2010/0048914 A1 | 2/2010 | Brodie et al. |
| 2010/0068802 A1 | 3/2010 | Qiu et al. |
| 2010/0137269 A1 | 6/2010 | Brodie et al. |
| 2010/0298383 A1 | 11/2010 | Ng et al. |
| 2011/0034428 A1 | 2/2011 | Morrison et al. |
| 2011/0105445 A1 | 5/2011 | Njar et al. |
| 2011/0110926 A1 * | 5/2011 | Luo .................. C07K 16/2869 424/130.1 |
| 2011/0118219 A1 | 5/2011 | Njar et al. |
| 2011/0160170 A1 | 6/2011 | Njar et al. |
| 2011/0178070 A1 | 7/2011 | Gong et al. |
| 2011/0195966 A1 | 8/2011 | Garcia-Echeverria et al. |
| 2011/0224223 A1 | 9/2011 | Shokat et al. |
| 2011/0312916 A1 | 12/2011 | Casebier |
| 2011/0312924 A1 | 12/2011 | Casebier |
| 2011/0313229 A1 | 12/2011 | Sugaya et al. |
| 2011/0319369 A1 | 12/2011 | Casebier et al. |
| 2012/0028972 A1 | 2/2012 | Wong et al. |
| 2012/0282331 A1 | 11/2012 | Chappel et al. |
| 2013/0130241 A1 | 5/2013 | Dehm |
| 2014/0288036 A1 | 9/2014 | Brodie et al. |
| 2014/0288037 A1 | 9/2014 | Casebier et al. |
| 2014/0343024 A1 | 11/2014 | Morrison et al. |
| 2014/0371181 A1 | 12/2014 | Casebier |
| 2015/0005265 A1 | 1/2015 | Stewart |
| 2015/0051179 A1 | 2/2015 | Casebier |
| 2015/0166599 A1 | 6/2015 | Morrison et al. |
| 2015/0174143 A1 | 6/2015 | Njar et al. |
| 2015/0203528 A1 | 7/2015 | Morrison et al. |
| 2015/0297615 A1 | 10/2015 | Njar et al. |
| 2015/0320770 A1 | 11/2015 | Casebier et al. |
| 2015/0361126 A1 | 12/2015 | Njar et al. |
| 2016/0000808 A1 | 1/2016 | Njar et al. |
| 2016/0038511 A1 | 2/2016 | Njar et al. |

FOREIGN PATENT DOCUMENTS

| | | |
|---|---|---|
| EP | 1712222 A2 | 10/2006 |
| EP | 0901786 B1 | 6/2007 |
| EP | 1530457 B1 | 9/2009 |

(56) References Cited

FOREIGN PATENT DOCUMENTS

| | | |
|---|---|---|
| GB | 972672 A | 10/1964 |
| GB | 2479337 A | 10/2011 |
| JP | 38-022578 | 10/1963 |
| JP | S51-41372 A | 4/1976 |
| JP | 56-003000 | 1/1981 |
| JP | H06-192287 A | 7/1994 |
| JP | H07-505377 A | 6/1995 |
| JP | H08-509617 A | 10/1996 |
| JP | 2008-536807 A | 9/2008 |
| WO | WO-92/05179 A1 | 4/1992 |
| WO | WO-93/11130 A1 | 6/1993 |
| WO | WO-93/20097 A1 | 10/1993 |
| WO | WO-94/02136 A1 | 2/1994 |
| WO | WO-94/02485 A1 | 2/1994 |
| WO | WO-94/09010 A1 | 4/1994 |
| WO | WO-94/25626 A1 | 11/1994 |
| WO | WO-95/14023 A1 | 5/1995 |
| WO | WO-95/16691 A1 | 6/1995 |
| WO | WO-96/41807 A1 | 12/1996 |
| WO | WO-98/02441 A2 | 1/1998 |
| WO | WO-99/63974 A2 | 12/1999 |
| WO | WO-01/14387 A1 | 3/2001 |
| WO | WO-01/19828 A2 | 3/2001 |
| WO | WO-03/032950 A1 | 4/2003 |
| WO | WO-2005/009429 A1 | 2/2005 |
| WO | WO-2005/014023 A1 | 2/2005 |
| WO | WO-2005/047289 A1 | 5/2005 |
| WO | WO-2005/097107 A2 | 10/2005 |
| WO | WO-2006/093993 A1 | 9/2006 |
| WO | WO-2007/061737 A2 | 5/2007 |
| WO | WO-2007/064993 A2 | 6/2007 |
| WO | WO-2007/087395 A2 | 8/2007 |
| WO | WO-2008/027855 A2 | 3/2008 |
| WO | WO-2008/109163 A1 | 9/2008 |
| WO | WO-2008/154382 A1 | 12/2008 |
| WO | WO-2009/114658 A2 | 9/2009 |
| WO | WO-2009/120565 A2 | 10/2009 |
| WO | WO-2010/028646 A1 | 3/2010 |
| WO | WO-2010/089763 A2 | 8/2010 |
| WO | WO-2010/091299 A2 | 8/2010 |
| WO | WO-2010/091306 A1 | 8/2010 |
| WO | WO-2010/111132 A2 | 9/2010 |
| WO | WO-2011/116344 A2 | 9/2011 |
| WO | WO-2012/129408 A2 | 9/2012 |
| WO | WO-2013/012959 A1 | 1/2013 |
| WO | WO-2013/079964 A1 | 6/2013 |
| WO | WO-2013/096907 A1 | 6/2013 |
| WO | WO-2014/153215 A1 | 9/2014 |
| WO | WO-2015/023710 A1 | 2/2015 |

OTHER PUBLICATIONS

Abstract of NIH Grant Project Reference No. 2R01 CA27440-25A1, approximate submission date Feb. 18, 2004; approximate award date Sep. 23, 2004.
Abstract of NIH Grant Project Reference No. 3R01 CA27440-23S1, approximate date May 3, 2002; approximate award date Jun. 21, 2002.
Abstract of NIH Grant Project Reference No. 3R01 CA27440-24S1, approximate date Apr. 1, 2003; approximate award date Jun. 3, 2003.
Abstract of NIH Grant Project Reference No. 5R01 CA27440-23, approximate date Jan. 21, 2002; approximate award date Apr. 29, 2002.
Abstract of NIH Grant Project Reference No. 5R01 CA27440-24, approximate date Feb. 20, 2003; approximate award date Jun. 3, 2003.
Abstract of NIH Grant Project Reference No. 5R01 CA27440-26, approximate submission date Jul. 1, 2005; approximate award date Aug. 2, 2005.
Abstract of NIH Grant Project Reference No. 5R01 CA27440-27, approximate submission date Apr. 26, 2006.
Abstract of NIH Grant Project Reference No. 3R01 CA27440-22S1, approximate date Jun. 21, 2001; approximate award date Aug. 17, 2001.
Angelastro, M.R. et al., 17 beta-(cyclopropylamino)-androst-5-en-3 beta-ol, a selective mechanism-based inhibitor of cytochrome P450(17 alpha) (steroid 17 alpha-hydroxylase/C17-20 lyase), Biochemical and Biophysical Research Communications, 162(3):1571-1577 (1989).
Armstrong, A.J. et al., A pharmacodynamic study of rapamycin in men with intermediate to high risk localized prostate cancer: A Department of Defense Prostate Cancer Clinical Trials Consortium Trial, Clin. Cancer Res., 16(11):3057-66 (2010).
Auchus, R.J. et al., Use of Prednisone with Abiraterone Acetate in Metastatic Castration-Resistant Prostate Cancer, The Oncologist, 19:1-10 (2014).
Ausubel, et al. Current Protocols in Molecular Biology. 1987.
Author Not Known, Definition of Poloxamer, Wikipedia.org, 3 pages, retrieved in May 1, 2014 <http://en.wikipedia.org/wiki/Poloxamer>.
Author Not Known, Highlights of Prescribing Information for Lupron Depot, AbbVie Inc., Chicago, IL, Takeda Pharmaceutical Company, Japan, 26 pages, initial U.S. Approval: 1989, most recent update: 2014.
Author Not Known, Phase I Study of Palomid 529 a Dual TORC1/2 Inhibitor of the PI3K/Akt/mTOR Pathway for Advanced Neovascular Age-Related Macular Degeneration (P52901), ClinicalTrials.gov: A Service of the U.S. National Institutes of Health (2012), 3 pages, retrieved on Sep. 16, 2015 <https://clinicaltrials.gov/ct2/show/NCT01033721>.
Ayub, M. et al., Inhibition of testicular 17 alpha-hydroxylase and 17,20-lyase but not 3 beta-hydroxysteroid dehydrogenase-isomerase or 17 beta-hydroxysteroid oxidoreductase by ketoconazole and other imidazole drugs, Journal of Steroid Biochemistry, 28(5):521-531 (1987).
Baldo, P. et al., mTOR pathway and mTOR inhibitors as agents for cancer therapy, Curr. Cancer Drug Targets, 8(8):647-65 (2008). [Abstract Only].
Banks, P.K. et al., Regulation of ovarian steroid biosynthesis by estrogen during proestrus in the rat, Endocrinology, 129(3):1295-1304 (1991).
Barrie, S. E. et al., Pharmacology of novel steroidal inhibitors of cytochrome P450(17) alpha (17 alpha-hydroxylase/C17-20 lyase). J Steroid Biochem Mol Biol. 50:(5-6):267-273 (1994).
Barrie, S.E. et al., Inhibition of 17 alpha-hydroxylase/C17-C20 lyase by bifluranol and its analogues, Journal of Steroid Biochemistry, 33(6):1191-1195 (1989).
Berge, et al. Pharmaceutical Salts. Journal of Pharmaceutical Sciences, 66 (1); 1977: 1-17.
Brodie, A.M.H. et al., Inactivation of aromatase in vitro by 4-hydroxy-4-androstene-3,17-dione and 4-acetoxy-4-androstene-3,17-dione and sustained effects in vivo, Steroids, 38(6):693-702 (1981).
Brodie, A.M.H. et al., Studies on the mechanism of estrogen biosynthesis in the rat ovary—I, Journal of Steroid Biochemistry, 7(10):787-793 (1976).
Brodie, A.M.H. Steroidogenesis Pathway Enzymes—Section 9A Introduction, Design of Enzyme Inhibitors as Drugs vol. 2, M. Sandler and H.J. Smith, Oxford University Press, (Ch. 9):414-423 (1993).
Brodie, A.M.H., et al. Lack of evidence for aromatase in human prostatic tissues: effects of 4-hydroxyandrostenedione and other inhibitors on androgen metabolism, Cancer Research, 49(23):6551-6555 (1989).
Brodie, A.M.H., Inhibitors of Steroid Biosynthesis, Design of Enzyme Inhibitors as Drugs vol. 2, M. Sandler and H.J. Smith, Oxford University Press, (Ch.16):503-522 (1993).
Brodie, A.M.H., Steroidogenesis Pathway Enzymes—Aromatase Inhibitors, Design of Enzyme Inhibitors as Drugs vol. 2, M. Sandler and H.J. Smith, Oxford University Press, (Section 9B):424-438 (1993).
Bruchovsky, N and Wilson, J., The conversion of testosterone to 5-alpha-androstan-17-beta-ol-3-one by rat prostate in vivo and in vitro. J Biol Chem. 243(8):2012-2021 (1968).
Bruno, R. D. et al., 17.alpha.-Hydroxylase/17,20 Lyase Inhibitor VN/124-1 Inhibits Growth of Androgen-independent Prostate Can-

(56) References Cited

OTHER PUBLICATIONS cer Cells via Induction of theEndoplasmic Reticulum Stress Response, Molecular Cancer Therapeutics, 7 (9), 2828-2836 (2008).
Bruno, R.D. et al., Synthesis and biological evaluations of putative metabolically stable analogs of VN/124-1 (TOK-001): head to head anti-tumor efficacy evaluation of VN/124-1 (TOK-001) and abiraterone in LAPC-4 human prostate cancer xenograft model, Steroids, 76(12):1268-79 (2011).
Bruno, R.D. et al., Targeting cytochrome P450 enzymes: a new approach in anti-cancer drug development, Bioorganic & Medicinal Chemistry, 15(15):5047-5060 (2007).
Bulun, S.E. et al., Use of tissue-specific promoters in the regulation of aromatase cytochrome P450 gene expression in human testicular and ovarian sex cord tumors, as well as in normal fetal and adult gonads, The Journal of Clinical Endocrinology & Metabolism, 77(6):1616-1621 (1993).
Burkhart, J. P. et al., Inhibition of steroid C17(20) lyase with C-17-heteroaryl steroids. Bioorg Med Chem. 4(9):1411-1420 (1996).
Bühler, Pharmaceutical Technology of BASF Excipient, 3rd revised edition, pp. 6-164 (2008).
Chang, S.S., Treatment options for hormone refractory prostate cancer, Rev. Urol., 9 (Suppl 2): S13-S18 (2007).
Chao, J. et al., A versatile synthesis of 17-heterosrylandrostenes via palladium-mediated Suzuki cross-coupling with heteroarylboronic acids, Steroids, 71(7):585-590 (2006).
Chaumeil, J. C., Micronization: A Method of Improving the Bioavailability of Poorly Soluble Drugs, Meth Find Exp Clin Pharmacol 20(3):211-215 (1998).
Chen, C. D. et al., Molecular determinants of resistance to antiandrogen therapy, Nat Med. 10(1):33-39 (2004).
Chengjie, R. et al., Syntheses and Pharmacological Activity of some 17-[2'substituted)-4'-pyrimidyl] androstene derivativies as inhibitors of human 17alpha-hydroxylase/C17,20-lyse., J. Chin. Pharm. Sci., 10(1): 3-8 (2001).
Chomczynski, P. and Sacchi, N., Single-step method of RNA isolation by acid guanidinium thiocyanate-phenol-chloroform extraction, Analytical Biochemistry, 162(1):156-159 (1987).
Choshi, T. et al., Total synthesis of grossularines-1 and -2. J. Org. Chem. 60:5899-5904 (1995).
Christensen, S.B. et al., Thapsigargin analogues for targeting programmed death of androgen-independent prostate cancer cells, Bioorganic & Medicinal Chemistry, 7(7):1273-1280 (1999).
Church, G.M. and Gilbert, W., Genomic sequencing, Proceedings of the National Academy of Sciences of the USA, 81(7):1991-1995 (1984).
Clement, O., et al., Three dimensional pharmacophore modeling of human CYP17 inhibitors. Potential agents for prostate cancer therapy, Journal of Medicinal Chemistry,46(12):2345-2351 (2003).
Coen, P. et al., An aromatase-producing sex-cord tumor resulting in prepubertal gynecomastia, The New England Journal of Medicine, 324(5):317-322 (1991).
Cohen, S.M. et al., Comparison of the effects of new specific azasteroid inhibitors of steroid 5 alpha-reductase on canine hyperplastic prostate: suppression of prostatic DHT correlated with prostate regression, The Prostate, 26(2):55-71 (1995).
Communication pursuant to Article 94(3) EPC for EP 10150763.0, 12 pages (Mar. 23, 2012).
Communication Pursuant to Article 94(3) EPC for EP 10704283.0, 9 pages (Nov. 6, 2012).
Coombes, R.C. et al., 4-Hydroxyandrostenedione treatment for postmenopausal patients with advanced breast cancer, Steroids, 50(1-3):245-252 (1987).
Covey, D.F. et al., 10 beta-propynyl-substituted steroids. Mechanism-based enzyme-activated irreversible inhibitors of estrogen biosynthesis, The Journal of Biological Chemistry, 256(3):1076-1079 (1980).
Crawford, E. D. et al., A controlled trial of leuprolide with and without flutamide in prostatic carcinoma, New Eng J Med. 321:419-424 (1989).

Crawford, E.D. et al., Treatment of newly diagnosed stage D2 prostate cancer with leuprolide and flutamide or leuprolide alone, phase III: prognostic significance of minimal disease, J. Urol., Abstract from AUA Eighty-Seventh Annual Meeting, May 10-14, 1992, 147:417A (1992).
De Souza, et al. Enhancement of paclitaxel activity against hormone-refractory prostate cancer cells in vitro and in vivo by quinacrine. Br J Cancer. 1997; 75 (11): 1593-600.
Dehm, S.M., et al., Splicing of a Novel Androgen Receptor Exon Generates a Constitutively Active Androgen Receptor that Mediates Prostate Cancer Therapy Resistance, Cancer Res., 68(13):5469-5477 (2008).
Denis, L., Role of maximal androgen blockade in advanced prostate cancer. The Prostate Supplement, 5:17-22 (1994).
Denmeade, S.R. and Isaacs, J.T., A history of prostate cancer treatment. Nat Rev Cancer. 2(5):389-396 (2002).
Denmeade, S.R. and Isaacs, J.T., The SERCA pump as a therapeutic target: making a "smart bomb" for prostate cancer, Cancer Biology & Therapy, 4(1):14-22 (2005).
Di Salle, E. et al., Effects of 5 alpha-reductase inhibitors on intraprostatic androgens in the rat, The Journal of Steroid Biochemistry and Molecular Biology, 53(1-6):381-385 (1995).
Dihrendra, K. et al, Solid dispersions: a review, Pak. J. Pharm. Sci., 22(2):234-246 (2009).
Doorenbos, N.J. and Milewich, L., 17-beta-isoxazolyl and 17-beta-pyrazolyl steroids from 3-beta-hydroxy-21-formylpregn-5-en-20-one. Structural assignments, The Journal of Organic Chemistry, 31(10):3193-3199 (1966).
Dorwald, F.Z., Side Reactions in Organic Synthesis: A Guide to Successful Synthesis Design, Weinheim: WILEY-VCH Verlag GmbH and Co. KGaA, Preface, 4 pages (2005).
Duc, I. et al., In vitro and in vivo models for the evaluation of potent inhibitors of male rat 17alpha-hydroxylase/C17,20-lyase, J. Steroid. Biochem. Mol. Biol., 84(5):537-42 (2003).
Eisenhauer, et al. New response evaluation criteria in solid tumours: revises RECIST guideline (version 1.1), Eur. J. Cancer, 45(2): 228-47 (2009).
Elliott, G.B et al. Latent carcinoma of the prostate in a 24-year-old man receiving cyclophosphamide and azathioprine, Can. Med. Assoc. J., 116 (6):651-2 (1977).
Evans, B. E. et al., Methods for drug discovery: development of potent, selective, orally effective cholecystokinin antagonists. J Med Chem, 31(12):2235-2246 (1988).
Examination Report for GB 1114154.6, 2 pages (May 30, 2013).
Extended European Search Report for EP 06736460, 15 pages (Jul. 29, 2009).
Extended European Search Report for EP 10150763.0, 14 pages (Dec. 2, 2010).
Extended European Search Report for EP 10807167.1, 10 pages (Nov. 6, 2012).
Extended European Search Report for EP 10830591.3, 8 pages (Feb. 20, 2013).
Extended European Search Report for EP 12814940.8, 5 pages (May 18, 2015).
Extended European Search Report for EP 12859516.2, 8 pages (May 26, 2015).
Fedorak, et al. A novel colon-specific steroid prodrug enhances sodium chloride absorption in rat colitis. Am J Physiol. Aug. 1995; 269 (2 Pt 1): G210-8.
Feldman, B.J. et al., The development of androgen-independent prostate cancer, Nature Reviews Cancer, 1(1):34-45 (2001).
Forti, G. et al., Three-month treatment with a long-acting gonadotropin-releasing hormone agonist of patients with benign prostatic hyperplasia: effects on tissue androgen concentration, 5 alpha-reductase activity and androgen receptor content, The Journal of Clinical Endocrinology & Metabolism, 68(2):461-468 (1989).
Frey, B.M. et al., Pharmacokinetics of 3 prednisolone prodrugs. Evidence of therapeutic inequivalence in renal transplant patients with rejection, Transplantation, 39(3):270-274 (1985).
Frye, S.V. et al., 6-Azasteroids: potent dual inhibitors of human type 1 and 2 steroid 5 alpha-reductase, The Journal of Medicinal Chemistry, 36(26):4313-4315 (1993).

(56) References Cited

OTHER PUBLICATIONS

Frye, S.V. et al., 6-Azasteroids: structure-activity relationships for inhibition of type 1 and 2 human 5 alpha-reductase and human adrenal 3 beta-hydroxy-delta 5-steroid dehydrogenase/3-keto-delta 5-steroid isomerase, The Journal of Medicinal Chemistry, 37(15):2352-2360 (1994).

Frye, S.V. et al., Structure-activity relationships for inhibition of type 1 and 2 human 5 alpha-reductase and human adrenal 3 beta-hydroxy-delta 5-steroid dehydrogenase/3-keto-delta 5-steroid isomerase by 6-azaandrost-4-en-3-ones: optimization of the C17 substituent, The Journal of Medicinal Chemistry, 38(14):2621-2627 (1995).

Funke, R. et al., A Phase Ib/II Study Testing the Safety and Efficacy of Combined Inhibition of the PI3K/Akt and Androgen Receptor Signaling Pathways in Castration-resistant Prostate Cancer: GDC-0068 or GDC-0980 with Abiraterone Acetate Versus Abiraterone Acetate, Array Biopharma, TPS2616, 1 page (2012), retrieved on Sep. 25, 2012 <http://www.arraybiopharma.com/_documents/Publication/PubAttachment524.pdf>.

Gaddipati, J.P. et al., Frequent detection of codon 877 mutation in the androgen receptor gene in advanced prostate cancers, Cancer Research, 54(11):2861-2864 (1994).

Garde, D., Tokai Pharmaceuticals' Reformulated Galeterone Demonstrates Robust PSA Reductions in Advanced Prostate Cancer Patients, FierceBiotech, 2 pages, Jan. 2, 2014. URL: http://www.fiercebiotech.com/node/349034/print (Retrieved from the Internet Jul. 28, 2015).

Garrett, R. H. et al. [Editors]. Chapter 8: Lipids. Biochemistry (Second Edition). Saunders College Publishing. pp. 238-258 (1999).

Geller, J. et al., Comparison of prostatic cancer tissue dihydrotestosterone levels at the time of relapse following orchiectomy or estrogen therapy, The Journal of Urology, 132(4):693-696 (1984).

Gold, R. et al., Detection of DNA fragmentation in apoptosis: application of in situ nick translation to cell culture systems and tissue sections, Journal of Histochemistry & Cytochemistry, 41(7):1023-1030 (1993).

Goldman, A.S. et al., Production of male pseudohermaphroditism in rats by two new inhibitors of steroid 17alpha-hydroxylase and C 17-20 lyase, Journal of Endocrinology, 71(3):289-297 (1976).

Gomez-Orellana, I., Strategies to improve oral drug bioavailability, Expert Opinion on Drug Delivery, 2(3):419-433 (2005).

Goodin, et al. Effect of docetaxel in patients with hormone-dependent prostate-specific antigen progression after local therapy for prostate cancer. J Clin Oncol. May 20, 2005; 23(15): 3352-7. Epub Feb. 28, 2005.

Gormley, G.J., Role of 5 alpha-reductase inhibitors in the treatment of advanced prostatic carcinoma, Urologic Clinics of North America, 18(1):93-98 (1991).

Goss, P.E. et al., Treatment of advanced postmenopausal breast cancer with an aromatase inhibitor, 4-hydroxyandrostenedione: phase II report, Cancer Research, 46(9):4823-4826 (1986).

Goya, S. et al., Studies on cardiotonic steroid analogs, V.: synthesis of 17β(or α)-isoxazolyl and pyrazolyl-16-methyl-14β(or α)-androst-5-enes, Yakugaku Zasshi, 90(5):537-543 (1970) [English Abstract Only].

Gravina, G.L. et al., The TORC1/TORC2 inhibitor, Palomid 529, reduces tumor growth and sensitizes to docetaxel and cisplatin in aggressive and hormone-refractory prostate cancer cells, Endocr. Relat. Cancer, 18(4):385-400 (2011).

Greene, et al. Protective Groups in Organic Synthesis, 2nd Ed. John Wiley and Sons. 1991.

Griengl, H. et al. Phosphonoformate and phosphonoacetate derivatives of 5-substituted 2'-deoxyuridines: synthesis and antiviral activity, J. Med. Chem., 31(9):1831-9 (1988).

Grigoryev, D. N. et al., Cytochrome P450c17-expressing *Escherichia coli* as a first-step screening system for 17alpha-hydroxylase-C17,20-lyase inhibitors, Analytical Biochem. 267(2):319-30 (1999).

Grigoryev, D. N. et al., Effects of new 17alpha-hydroxylase/C(17,20)-lyase inhibitors on LNCaP prostate cancer cell growth in vitro and in vivo. Br J Cancer. 81(4):622-630 (1999).

Guarna, A. et al., A concise route to 19-nor-10-azasteroids, a new class of steroid 5α-reductase inhibitors. 3.1 synthesis of (+)-19-nor-10-azatestosterone and (+)-17β-(acetyloxy)-(5β)-10-azaestr-1-en-3-one, The Journal of Organic Chemistry, 63(12):4111-4115 (1998).

Guo, Z. et al., A Novel Androgen Receptor Splice Variant is Up-regulated during Prostate Cancer Progression and Promotes Androgen Depletion-Resistant Growth, Cancer Res., 69(6):2305-2313 (2009).

Haase-Held, M. et al., The synthesis of 4-cyanoprogesterone: a potent inhibitor of the enzyme 5-α-reductase, Journal of the Chemical Society, Perkin Transactions 1, 22:2999-3000 (1992).

Habernicht, U.F. et al., Induction of estrogen-related hyperplastic changes in the prostate of the cynomolgus monkey (*Macaca fascicularis*) by androstenedione and its antagonization by the aromatase inhibitor 1-methyl-androsta-1,4-diene-3,17-dione, The Prostate, 11(4):313-326 (1987).

Haffner, C., Synthesis of 6-azacholesten-3-ones: potent inhibitors of 5?-reductase, Tetrahedron Letters, 36(23):4039-4042 (1995).

Haidar, S. et al. Effects of novel 17alpha-hydroxylase/C17, 20-lyase (P450 17, CYP 17) inhibitors on androgen biosynthesis in vitro and in vivo. J Steroid Biochem Mol Biol. 84(5):555-562 (2003).

Haidar, S. et al., Novel steroidal pyrimidyl inhibitors of P450 17 (17 alpha-hydroxylase/C17-20-lyase). Arch Pharm, Pharm Med. Chem 334(12):373-374 (2001).

Hakki, T. and Bernhardt, R., CYP17- and CYPIIB-dependent steroidhydroxylases as drug development targets, Pharmacology & Therapeutics, 111(1):27-52 (2006).

Hamilton, G.A., Chemical models and mechanisms for oxygenases, Molecular Mechanisms of Oxygen Activation, 1:405-451 (1974).

Hamm, R. et al., Patient self-injection: A new approach to administering luteinizing hormone-releasing hormone analogues, 86(7): 840-842 (2000).

Handratta, V. D. et al, Potent CYP17 inhibitors: improved syntheses, pharmacokinetics and anti-tumor activity in the LNCaP human prostate cancer model. J Steroid Biochem Mol Biol. 92(3):155-165 (2004).

Handratta, V. et al., Novel C-17-heteroaryl steroidal CYP17 inhibitors/antiandrogens: synthesis, in vitro biological activity, pharmacokinetics, and antitumor activity in the LAPC4 human prostate cancer xenograft model, Journal of Medicinal Chemistry, 48(8):2972-2984 (2005).

Harada, N., Novel properties of human placental aromatase as cytochrome P-450: purification and characterization of a unique form of aromatase, The Journal of Biochemistry, 103(1):106-113 (1988).

Harlow, et al. Antibodies, a laboratory manual. 1988.

Hartley, T. et al., Endoplasmic reticulum stress response in an INS-1 pancreatic beta-cell line with inducible expression of a folding-deficient proinsulin, BMC Cell Biology, 11:59 (2010).

Hartmann, R. W. et al. Synthesis and evaluation of novel steroidal oxime inhibitors of P450 17 (17 alpha-hydroxylase/C17-20-lyase) and 5 alpha-reductase types 1 and 2. J Med Chem. 43(22):4266-4277 (2000).

Henderson, D. et al., Estrogens and benign prostatic hyperplasia: the basis for aromatase inhibitor therapy, 50(1-3):219-233 (1987).

Higuchi and Stella, V., Pro-drugs as novel drug delivery systems. American Chemical Soceity. ACS symposium series 14. (1975).

Hochhaus, et al. A selective HPLC/RIA for dexamethasone and its prodrug dexamethasone-21-sulphobenzoate sodium in biological fluids. Biomed Chromatogr. Nov.-Dec. 1992; 6 (6): 283-6.

Hoehn, W. et al., Human prostatic adenocarcinoma: some characteristics of a serially transplantable line in nude mice (PC 82), The Prostate, 1(1):95-104 (1980).

Holt, D.A. et al., Inhibition of steroid 5 alpha-reductase by unsaturated 3-carbonysteroids, The Journal of Medicinal Chemistry, 33(3):943-950 (1990).

Hsiang, Y.H. et al., The influence of 4-hydroxy-4-androstene-3,17-dione on androgen metabolism and action in cultured human foreskin fibroblasts, Journal of Steroid Biochemistry, 26(1):131-135 (1987).

Hu, R. et al., Ligand-Independent Androgen Receptor Variants Derived from Splicing of Cryptic Exons Signify Hormone-Refractory Prostate Cancer, Cancer Res., 69(1):16-22 (2009).

(56) References Cited

OTHER PUBLICATIONS

Hudes, et al. Paciltaxel plus estramustine in metastatic hormone-refractory prostate cancer. Seminars in Oncology, vol. 22, No. 5. Suppl. 12. Oct. 1995, pp. 41-45.
Huggins, C. et al., Studies in prostate cancer: The effects of castration on advanced carcinoma of the prostate gland, Arch. Surg., 43(2):209-22 (1941), retrieved on Sep. 30, 2009 <www.archsurg.com>.
Humber, D. C. et al. Synthesis and biological activity of some cardiotonic compounds related to digitoxigenin. Steroids. 42(2):189-202 (1983).
Humez, S. et al., Role of endoplasmic reticulum calcium content in prostate cancer cell growth regulation by IGF and TNFalpha, Journal of Cellular Physiology, 201(2):201-213 (2004).
Hussain, et al. Docetaxel followed by hormone therapy after failure of definitive treatments for clinically localized/locally advanced prostate cancer; preliminary results. Seminars in Oncology, vol. 28, No. 4, Suppl. 15 Aug. 2001, pp. 22-31.
Huynh, C. and Julia, Fixation d'un Groupe Nitrile en Position 4 des Ceto-3.sub..DELTA..sup.4-Steroides, Bull. Soc. Chim. Fr., 4396, (1971) [English translation of introduction].
Inkster, S. et al., Human testicular aromatase: immunocytochemical and biochemical studies, The Journal of Clinical Endocrinology & Metabolism, 80(6):1941-1947 (1995).
International Search Report and Written Opinion for PCT/US10/044570 (Apr. 29, 2011).
International Search Report and Written Opinion for PCT/US2010/023391 (Jun. 17, 2010).
International Search Report and Written Opinion for PCT/US2010/040448 (Nov. 30, 2009).
International Search Report and Written Opinion for PCT/US2010/055996 (Jul. 28, 2011).
International Search Report and Written Opinion for PCT/US2012/071485 (Feb. 27, 2013).
International Search Report for PCT/US2006/007143, 1 page (Aug. 14, 2006).
International Search Report for PCT/US2009/036891, 3 pages (Oct. 7, 2009).
International Search Report for PCT/US2009/037610, 4 pages (Dec. 1, 2009).
International Search Report for PCT/US2010/023381 (dated Jun. 9, 2010).
International Search Report for PCT/US2010/023387 (Jul. 5, 2010).
International Search Report for PCT/US2012/047253, 5 pages (Dec. 7, 2012).
Ishibashi, K. et al., Synthesis of b-nor-4-aza-5α-androstane compound as 5α-reductase inhibitor, Bioorganic & Medicinal Chemistry Letters, 4(5):729-732 (1994).
Jain, et al. Food and oral antineoplastics: more than meets the eye. Clin Cancer Res. Sep. 1, 2010; 16(17): 4305-7. doi: 10.1158/1078-0432.CCR-10-1857. Epub Aug. 24, 2010.
Jarman, M. et al., Hydroxyperfluoroazobenzenes: novel inhibitors of enzymes of androgen biosynthesis, The Journal of Medicinal Chemistry, 33(9):2452-2455 (1990).
Jarman, M. et al., Inhibitors of enzymes of androgen biosynthesis: cytochrome P450(17) alpha and 5 alpha-steroid reductase. Nat Prod Rep. 15(5):495-512 (1998).
Jarman, M. et al., The 16,17-double bond is needed for irreversible inhibition of human cytochrome p45017alpha by abiraterone (17-(3-pyridyl)androsta-5, 16-dien-3beta-ol) and related steroidal inhibitors, The Journal of Medicinal Chemistry, 41(27):5375-5381 (1998).
Jefcoate, C. R., Measurement of substrate and inhibitor binding to microsomal cytochrome P-450 by optical-difference spectroscopy. Methods Enzymol. 52:258-279 (1978).
Jemal, A. et al. Cancer statistics, 2004. CA cancer J. Clin. 54(1):8-29 (2004).
Kadar et al., Technical and safety aspects of blood and marrow transplantation using G-CSF mobilized family donors, Transfusion Science 17(4):611-618 (1996).
Kim, O. et al. Synergism of cytoplasmic kinases in IL6-induced ligand-independent activation of androgen receptor in prostate cancer cells. Oncogene. 23(10):1838-1844 (2004).
Kitz, R. and Wilson, I.B., Esters of methanesulfonic acid as irreversible inhibitors of acetylcholinesterase, The Journal of Biological Chemistry 237(10):3245-3249 (1962).
Klein, K. A. et al. Progression of metastatic human prostate cancer to androgen independence in immunodeficient SCID mice. Nat Med. 3(4):402-408 (1997).
Klus, G.T. et al., Growth inhibition of human prostate cells in vitro by novel inhibitors of androgen synthesis, Cancer Research, 56(21):4956-4964 (1996).
Kozák, I. et al., Nuclei of stroma: site of highest estrogen concentration in human benign prostatic hyperplasia, The Prostate, 3(5):433-438 (1982).
Krieg, M. et al., Stroma of human benign prostatic hyperplasia: preferential tissue for androgen metabolism and oestrogen binding, Acta Endocrinologica (Copenhagen), 96(3):422-432 (1981).
Kuppens, I.E.L.M. et al., Oral bioavailability of docetaxel in combination with OC144-093 (ONT-093), Cancer Chemother. Pharmacol., 55: 72-78 (2005).
Kyprianou, N. and Isaacs, J.T., Expression of transforming growth factor-beta in the rat ventral prostate during castration-induced programmed cell death, Molecular Endocrinology, 3(10):1515-1522 (1989).
Kyprianou, N. et al., Programmed cell death during regression of PC-82 human prostate cancer following androgen ablation, Cancer Research, 50(12):3748-3753 (1990).
Labrie, F. et al., Combination therapy for prostate cancer. Endocrine and biologic basis of its choice as new standard first-line therapy, Cancer, 71(3 Suppl):1059-1067 (1993).
Lai, E. et al., Endoplasmic reticulum stress: signaling the unfolded protein response, Physiology (Bethesda, Md.), 22(3):193-201 (2007).
Laneri, et al. Ionized prodrugs of dehydroepiandrosterone for transdermal iontophoretic delivery, Pharm. Res., 16(12): 1818-24 (1999).
Larsen, J.D. and Bundgaard, H., Prodrug forms for the sulfonamide group. I. Evaluation of N-acyl derivatives, N-sulfonylamidines, N-sulfonylsulfilimines and sulfonylureas as possible prodrug derivatives, Int. J. Pharmaceutics, 37:87-95 (1987).
Larsen, J.D. et al., Prodrug forms for the sulfonamide group. II. Water-soluble amino acid derivatives of N-methylsulfonamides as possible prodrugs, Int. J. Pharmaceutics, 47:103-110 (1988).
Li, J. et al., 4-pregnene-3-one-20β-carboxaldehyde: a potent inhibitor of 17α-hydroxylase/c17,20-lyase and of 5α-reductase, The Journal of Steroid Biochemistry and Molecular Biology, 42(3-4):313-320 (1992).
Li, J. et al., Inhibition of androgen synthesis by 22-hydroximino-23,24-bisnor-4-cholen-3-one, The Prostate, 26(3):140-150 (1995).
Li, J. et al., Synthesis and evaluation of pregnane derivatives as inhibitors of human testicular 17 alpha-hydroxylase/C17,20-lyase, The Journal of Medicinal Chemistry, 39(21):4335-4339 (1996).
Ling,Y.Z. et al., 17-Imidazolyl, pyrazolyl, and isoxazolyl androstene derivatives. Novel steroidal inhibitors of human cytochrome C17,20-lyase (P450(17 alpha), The Journal of Medicinal Chemistry, 40(20):3297-3304 (1997).
Long, B.J. et al., In vitro and in vivo inhibition of LNCaP prostate cancer cell growth by novel inhibitors of androgen synthesis, Proceedings of the American Association for Cancer Research, 90th Annual Meeting, Apr. 10-14, 1999, vol. 40, Abstract #423 (1999).
Lu, Q. et al., Expression of aromatase protein and messenger ribonucleic acid in tumor epithelial cells and evidence of functional significance of locally produced estrogen in human breast cancers, Endocrinology, 137(7):3061-3068 (1996).
Maggiolini, et al. The mutant androgen receptor T877A mediates the proliferative but not the cytotoxic dose-dependent effects of genistein and quercetin on human LNCaP prostate cancer cells. Molecular Pharmacology, vol. 62, pp. 1027-1035, 2002.
Matsunaga, N. et al. C(17,20)-lyase inhibitors. Part 2: design, synthesis and structure-activity relationships of (2-naphthylmethyl)-1H-imidazoles as novel C(17,20)-lyase inhibitors. Bioorg Med Chem. 12(16):4313-4336 (2004).

(56) References Cited

OTHER PUBLICATIONS

Matsunaga, N. et al. C17,20-lyase inhibitors I. Structure-based de novo design and SAR study of C17,20-lyase inhibitors. Bioorg Med. Chem. 12(9):2251-2273 (2004).
Matsunaga, N. et al. Synthetic studies on (1S)-1-(6,7-dimethoxy-2-naphthyl)-1-(1H-imidazol-4-yl)-2-methylpropan-1-o-I as a selective C17,20-lyase inhibitor. Tetrahedron: Asymmetry. 15:2021-2028 (2004).
Mawhinney, M.G. and Belts, J.A., Androgens and estrogens in prostatic neoplasia, Advances in Sex Hormone Research, 2:141-209 (1976).
McCague, R. et al., Inhibition of enzymes of estrogen and androgen biosynthesis by esters of 4-pyridylacetic acid, The Journal of Medicinal Chemistry, 33(11):3050-3055 (1990).
McConnell, J. D., Physiologic basis of endocrine therapy for prostatic cancer. Urol Clin North Am. 18(1):1-13 (1991).
McDonald, I.A. et al., Inhibition of steroid 5-alpha-reductase by "inverted" competitive inhibitors, Bioorganic and Medicinal Chemistry Letters, 4(6):847-851 (1994).
McLeod, et al. A glucocorticoid prodrug facilitates normal mucosal function in rat colitis without adrenal suppression. Gastroenterology. Feb. 1994; 106 (2): 405-13.
Metcalf, B.W. et al., Substrate-induced inactivation of aromatase by allenic and acetylenic steroids, Journal of the American Chemical Society, 103(11):3221-3222 (1981).
Mohler, J. L. et al., The androgen axis in recurrent prostate cancer. Clin Cancer Res. 10(2):440-448 (2004).
Montgomery, R.B. et al., Galeterone in men with CRPC: results in four distinct patient populations from the ARMOR2 study, Abstract #5029, Poster, Presented at the 50th Annual Meeting of the American Society of Clinical Oncology (ASCO), Chicago, Illinois (May 30, 2014-Jun. 3, 2014).
Moreira, V. et al. Synthesis and evaluation of novel 17-indazole androstene derivatives designed as CYP17 inhibitors, Steroids 72(14):939-948 (2007).
Moreira, V.M. et al., CYP17 inhibitors for prostate cancer treatment—an update, Curr. Med. Chem., 15(9):868-99 (2008) [Abstract Only].
Muscato, J. J. et al., Optimal dosing of ketoconazole (KETO) and hydrocortisone (HC) leads to long responses in hormone refractory prostate cancer, Thirtieth Annual Meeting of the Americal Society of Clinical Oncology, May 14-17, 1994, vol. 13, p. 229, Abstract 701 (1994).
Nakajin, S. and Hall, P.F., Microsomal cytochrome P-450 from neonatal pig testis. Purification and properties of a C21 steroid side-chain cleavage system (17 alpha-hydroxylase-C17,20 lyase), The Journal of Biological Chemistry, 256(8):3871-3876 (1981).
Nakajin, S. et al., Inhibitory effects and spectral changes in pig testicular cytochrome P-450(17 alpha-hydroxylase/lyase) by 20 beta-hydroxy-C21-steroids, Yakugaku Zasshi (Journal of the Pharmaceutical Society of Japan), 108(12):1188-1195 (1988) [English Abstract Only].
Nakajin, S. et al., Microsomal cytochrome P-450 from neonatal pig testis: two enzymatic activities (17 alpha-hydroxylase and c17,20-lyase) associated with one protein, Biochemistry, 20(14):4037-4042 (1981).
Nawrocki, S.T. et al., Bortezomib sensitizes pancreatic cancer cells to endoplasmic reticulum stress-mediated apoptosis, Cancer Research, 65(24):11658-11666 (2005).
Nicolaou, K. C. et al., Natural Product-like Combinatorial Libraries Based on Privileged Structures. 1. General Principles and Solid-Phase Synthesis of Benzopyrans, J. Am. Chem. Soc. 122(41):9939-9953 (2000).
NIH Grant Project Reference No. 2R01 CA27440-24A1, 2R01 CA27440-25A1 Revised Grant Renewal Application, approximate submission date Feb. 18, 2004; approximate award date Sep. 23, 2004, SAI.MD04. 02 12-5610-360221, 51 pages, signed Feb. 18, 2004.
NIH Grant Project Reference No. 3R01 CA27440-22S1 Grant Application for Supplemental Funding, approximate date Jun. 21, 2001; approximate award date Aug. 17, 2001, SAI:MD01:06 20-5504-360221, 31 pages, received Jun. 21, 2001, signed Jun. 14, 2001.
NIH Grant Project Reference No. 3R01 CA27440-23S1 Grant Continuation Application and Progress Report, approximate date May 3, 2002; approximate award date Jun. 21, 2002, MD01-0220-5807-360221, 3 pages, signed May 3, 2002.
NIH Grant Project Reference No. 5R01 CA27440-23 Grant Continuation Application and Progress Report, approximate date Jan. 21, 2002; approximate award date Apr. 29, 2002, SAI.MD02 17-5787-360221, 7 pages, signed Jan. 21, 2002.
NIH Grant Project Reference No. 5R01 CA27440-24 Grant Continuation Application and Progress Report, approximate date Feb. 20, 2003; approximate award date Jun. 3, 2003. CA27440-24, signed Apr. 1, 2003.
NIH Grant Project Reference No. 5R01 CA27440-24S1 Grant Continuation Application and Progress Report, 11 pages, approximate date Apr. 1, 2003; approximate award date Jun. 3, 2003.
NIH Grant Project Reference No. 5R01 CA27440-25 Grant Renewal Application, 39 pages, approximate submission date Jun. 26, 2003—Unfunded.
NIH Grant Project Reference No. 5R01 CA27440-26 Grant Renewal Continuation Application and Progress Report, approximate submission date Jul. 1, 2005; approximate award date Aug. 2, 2005, CA27440-26, 7 pages, signed Jul. 1, 2005.
NIH Grant Project Reference No. 5R01 CA27440-27 ESNAP Report, 9 pages, approximate submission date May 8, 2006.
NIH Grant Project Reference No. 5R01 CA27440-27 Grant Continuation Application and Progress Report, approximate submission date Apr. 26, 2006, CA27440-27, signed Apr. 26, 2006.
Nishimura, et al. Effects of flutamide as a second-line agent for maximum androgen blockade of hormone refractory prostate cancer. Int J Urol. Mar. 2007; 14 (3): 264-7.
Njar, V. and Brodie, A., Inhibitors of 17alpha-hydroxylase/17,20-lyase (CYP17): potential agents for the treatment of prostate cancer, Curr Pharm Des. 5(3):163-180 (1999).
Njar, V. et al., Novel 17-azolyl steroids, potent inhibitors of human cytochrome 17 alpha-hydroxylase-C17,20-1yase (P450(17) alpha): potential agents for the treatment of prostate cancer, J Med Chem. 41(6):902-912 (1998).
Njar, V. et al., Nucleophilic vinylic "addition-elimination" substitution reaction of 3.beta.-acetoxy-17-chloro-16-formylandrosta-5,16-diene: A novel and general route to 17-substituted steroids. Part 1—synthesis of novel 17-azolyl-.DELTA..sup.16steroids; inhibitors of 17.alpha.-hydroxylase/17,20-lyase (17.alpha.-lyase), Bioorganic & Medicinal Chemistry Letters, 6(22):2777-2782 (1996).
Njar, V.C. et al., Synthesis of novel 21-trifluoropregnane steroids: inhibitors of 17 alpha-hydroxylase/17,20-lyase (17 alpha-lyase), Steroids, 62(6):468-473 (1997).
Njar, V.C.O. et al., Novel 10β-aziridinyl steroids; inhibitors of aromatase, Journal of the Chemical Society, Perkin Transactions 1, 10:1161-1168 (1993).
Nnane, I. P. et al., Effects of novel 17-azolyl compounds on androgen synthesis in vitro and in vivo. J Steroid Biochem Mol Biol. 71(3-4):145-152 (1999).
Nnane, I.P. et al., Effects of some novel inhibitors of C17,20-lyase and 5alpha-reductase in vitro and in vivo and their potential role in the treatment of prostate cancer, Cancer Res., 58(17):3826-32 (1998).
Notice of Allowance for U.S. Appl. No. 12/851,070 (May 5, 2014).
Notice of Allowance for U.S. Appl. No. 13/145,997 (May 2, 2014).
O'Donnell, A. et al. Hormonal impact of the 17alpha-hydroxylase/C(17,20)-lyase inhibitor abiraterone acetate (CB7630) in patients with prostate cancer. Br J Cancer. 90(12):2317-2325 (2004).
Office Action dated Jan. 31, 2011 for U.S. Appl. No. 12/577,094.
Office Action dated Mar. 12, 2010 for U.S. Appl. No. 11/817,550.
Office Action dated Apr. 4, 2012 for U.S. Appl. No. 12/577,090.
Office Action dated May 5, 2010 for U.S. Appl. No. 12/577,091.
Office Action dated May 7, 2010 from U.S. Appl. No. 12/577,092.
Office Action dated May 12, 2014 for U.S. Appl. No. 13/146,004.
Office Action dated May 23, 2011 from U.S. Appl. No. 12/577,094.
Office Action dated May 25, 2010 for U.S. Appl. No. 12/577,096.
Office Action dated Jun. 1, 2010 from U.S. Appl. No. 12/577,090.
Office Action dated Jun. 1, 2011 for U.S. Appl. No. 12/623,257.
Office Action dated Jun. 2, 2010 for U.S. Appl. No. 11/817,550.

(56) References Cited

OTHER PUBLICATIONS

Office Action dated Sep. 8, 2011 from U.S. Appl. No. 12/577,096.
Office Action dated Sep. 9, 2011 from U.S. Appl. No. 12/577,090.
Office Action dated Sep. 19, 2013 for U.S. Appl. No. 13/146,004.
Office Action dated Oct. 5, 2011 for U.S. Appl. No. 12/577,094.
Office Action dated Oct. 17, 2012 for U.S. Appl. No. 12/577,090.
Office Action dated Oct. 20, 2010 for U.S. Appl. No. 12/623,257.
Office Action dated Oct. 28, 2010 for U.S. Appl. No. 12/577,091.
Office Action dated Oct. 28, 2010 for U.S. Appl. No. 12/577,092.
Office Action dated Oct. 29, 2010 from U.S. Appl. No. 12/577,090.
Office Action dated Nov. 01, 2010 from U.S. Appl. No. 12/577,096.
Office Action dated Aug. 29, 2013 for U.S. Appl. No. 13/145,997.
Office Action dated Feb. 5, 2015 for U.S. Appl. No. 14/313,894.
Office Action dated Feb. 8, 2013 for U.S. Appl. No. 12/934,135.
Office Action dated Sep. 16, 2013 for U.S. Appl. No. 12/934,135.
Office Action dated Sep. 19, 2013 for U.S. Appl. No. 12/851,070.
Office Action for JP 2007-558143, 7 pages (Mar. 7, 2012).
Office Action for U.S. Appl. No. 12/851,070, 19 pages (Mar. 12, 2013).
Ojida et al., Stereocontrolled synthesis of (1S)-1-(1H-imidazol-4-yl)-1-(6-methoxy-2-naphthyl)-2-methylpropan-1-ol as a potent C.sub.17,20-lyase inhibitor, Tetrahedron: Asymmetry, 15: 1555-1559 (2004).
Onoda, M. et al., Affinity alkylation of the active site of C21 steroid side-chain cleavage cytochrome P-450 from neonatal porcine testis: a unique cysteine residue alkylated by 17-(bromoacetoxy)progesterone, Biochemistry, 26(2):657-662 (1987).
Pappo, R. and Chorvat, R.J., The synthesis of 2-azasteroids, Tetrahedron Letters, 13(31):3237-3240 (1972).
Partial European Search Report for EP 10150763.0, 6 pages (Jul. 16, 2010).
Pataki, J. and Jensen, E.V., Synthesis of fluorinated 3beta-hydroxypregn-5-en-20-one derivatives, Steroids, 28(4):437-447 (1976).
Pelc, B. and Hodkova, J., Androstane derivatives substituted by pyrazole ring in position 17, Collection of Czechoslovak Chemical Communications, 34(2):442-450 (1969).
Petrow, V. and Lack, L., Studies on a 5-alpha-Reductase Inhibitor and Their Therapeutic Implications, The Prostate Cell: Structure and Function, Part B, pp. 283-297 (1981).
Picard, F. et al., Synthesis and evaluation of 2'-substituted 4-(4'-carboxy- or 4'-carboxymethylbenzylidene)-N-acylpiperidines: highly potent and in vivo active steroid 5alpha-reductase type 2 inhibitors. J Med Chem. 45(16):3406-3417 (2002).
Potter, G. A. et al., A convenient, large-scale synthesis of abiraterone acetate [3B-acetoxy-17-(3-pryidyl)androsta-5,16-diene], a potential new drug for the treatment of prostate cancer. Organic Preparations and Procedures Int. 29(1):123-134 (1997).
Potter, G.A. et al., Novel Steroidal Inhibitors of Human Cytochrome P450.sub.17.alpha.(17.alpha.-Hydroxylase-C.sub.17,20-lyase): Potential Agents for the Treatment of Prostatic Cancer, J. Med. Chem., 38(13): 2463-2471 (1995).
Purushottamachar, P. et al., Exploitation of Multi-target Prostate Cancer Clinical Candidate VN/124-1 (TOK-001) to Develop a Novel Class of Androgen Receptor Down Regulating Agents for Prostate Cancer Therapy, Poster, 242nd ACS National Meeting, Aug. 28-Sep. 1, 2011, Paper ID: 11268, 1 page (Aug. 28, 2011).
Purushottamachar, P. et al., Systematic Structure Modifications of Multi-target Prostate Cancer Drug Candidate Galeterone to Produce Novel Androgen Receptor Down-regulating Agents as an Approach to Treatment of Advanced Prostate Cancer, Journal of Medicinal Chemistry, 79 pages (2013).
Rahmani, M. et al. The kinase inhibitor sorafenib induces cell death through a process involving induction of endoplasmic reticulum stress, Molecular and Cellular Biology, 27(15):5499-5513 (2007).
Randimbivololona, F. and Lesne, M., Metabolism and excretion in bile of SC4453, a new semi-synthetic derivative of digoxin following an i.v. bolus injection in the guinea-pig. J. Pharmacol. 15(1):53-64 (1984).

Rasmusson, G.H. and Toney, J.H., Therapeutic Control of Androgen Action, Annual Reports in Medicinal Chemistry, 29(23):225-232 (1994).
Rasmusson, G.H. et al., Azasteroids as inhibitors of rat prostatic 5 alpha-reductase, The Journal of Medicinal Chemistry, 27(12):1690-1701 (1984).
Rasmusson, G.H. et al., Azasteroids: structure-activity relationships for inhibition of 5 alpha-reductase and of androgen receptor binding, The Journal of Medicinal Chemistry, 29(11):2298-2315 (1986).
Recanatini, M. et al., A new class of nonsteroidal aromatase inhibitors: design and synthesis of chromone and xanthone derivatives and inhibition of the P450 enzymes aromatase and 17 alpha-hydroxylase/C17,20-lyase. Med Chem. 44(5):672-680 (2001).
Reid, et al. CYP17 inhibition as a hormonal strategy for prostate cancer. Nat Clin Pract Urol. Nov. 2008; 5 (11): 610-20.
Remington: The Science and Practice of Pharmacy, Nineteenth Ed., Mack Publishing Co., Easton, Pennsylvania, (1995).
Rittmaster, R.S. et al., Differential effect of 5 alpha-reductase inhibition and castration on androgen-regulated gene expression in rat prostate, Molecular Endocrinology, 5(7):1023-1029 (1991).
Ron, D. and Walter, P., Signal integration in the endoplasmic reticulum unfolded protein response, Nature Reviews Molecular Cell Biology, 8(7):519-529 (2007).
Russell, D.W. and Wilson, J.D., Steroid 5 alpha-reductase: two genes/two enzymes, Annual Review of Biochemistry, 63:25-61 (1994).
Saad, et al. The Canadian Uro-Oncology Group multicentre phase II study of docetaxel administered every 3 weeks with prednisone in men with metastatic hormone-refractory prostate cancer progressing after mitoxantrone/prednisone. BJU Int. Aug. 5, 2008; 102 (5); 551-5, doi: 10.1111/j.1464-410X.2008.07733.x Epub May 28.
Saulnier, et al. An efficient method for the synthesis of guanidino prodrugs. Bioorganic and Medicinal Chemistry Letters. 1994; 4(16):1985-1990.
Schayowitz, A. et al., Prolonging hormone sensitivity in prostate cancer xenografts through dual inhibition of AR and mTOR, Br. J. Cancer, 103(7):1001-7 (2010).
Schayowitz, et al. Synergistic effect of a novel antiandrogen, VN/124-1, and signal transduction inhibitors in prostate cancer progression of hormone independence in vitro. Mol. Cancer Ther., vol. 7 (1), pp. 121-132, Jan. 2008.
Schayowitz. Synergistic effect of anti-androgens and signal transduction inhibitors in prostate cancer progression, University of Maryland Baltimore Thesis, 86 pages (2008).
Schieweck, K. et al., Anti-tumor and endocrine effects of non-steroidal aromatase inhibitors on estrogen-dependent rat mammary tumors, The Journal of Steroid Biochemistry and Molecular Biology, 44(4-6):633-636 (1993).
Schwarzel, W.C. et al., Studies on the mechanism of estrogen biosynthesis. 8. The development of inhibitors of the enzyme system in human placenta, Endocrinology, 92(3):866-880 (1993).
Shao, T.C. et al., Effects of finasteride on the rat ventral prostate, Journal of Andrology, 14(2):79-86 (1993).
Shearer, R. and Davies, J.H., Studies in Prostatic Cancer with 4-Hydroxyandrostenedione, 4-hydroxyandrostenedione—A new approach to hormone-dependent cancer, Royal Society of Medicine Services, Limited, Ed. Coombes, R.C. and Dowsett, M., Royal Society of Medicine Services International Congress and Symposium Series No. 180, pp. 41-44 (1991).
Simmons, et al. Combined androgen blockade revisited: emerging options for the treatment of castration-resistant prostate cancer. Urology. Apr. 2009; 73 (4): 697-705.
Sinkula, J.A. and Yalkowsky, S.H., Rationale for design of biologically reversible drug derivatives: prodrugs, J. Pharm. Sci., 64(2):181-210 (1975).
Sjoerdsma, A., Suicide enzyme inhibitors as potential drugs, Clinical Pharmacology & Therapeutics, 30(1):3-22 (1981).
Skryma, R. et al., Store depletion and store-operated Ca2+ current in human prostate cancer LNCaP cells: involvement in apoptosis, The Journal of Physiology, 527(Pt 1):71-83 (2000).
Small, E. J. et al. Ketoconazole retains activity in advanced prostate cancer patients with progression despite flutamide withdrawal. J Urol. 157(4):1204-1207 (1997).

(56) References Cited

OTHER PUBLICATIONS

Snider, C.E. and Brueggemeier, R.W., Covalent modification of aromatase by a radiolabeled irreversible inhibitor, Journal of Steroid Biochemistry, 22(3):325-330 (1985).
Souillac et al., Characterization of Delivery Systems, Differential Scanning Calorimetry in Encyclopedia of Controlled Drug Delivery, John Wiley & Sons, 212-227 (1999).
Stangelberger, et al. The combination of antagonists of LHRH with antagonists of GHRH improves inhibition of androgen sensitive MDA-PCa-2b and LuCaP-35 prostate cancers. Prostate. Sep. 1, 2007; 67 (12): 1339-53.
STN Registry No. 851983-85-2, CAS Registry, 1 page, entered STN Jun. 9, 2005.
Stoner, E., The clinical development of a 5 alpha-reductase inhibitor, finasteride, The Journal of Steroid Biochemistry and Molecular Biology 37(3):375-378 (1990).
Szendi, Z. et al., Steroids, LIII: new routes of aminosteroids[1], Monatshefte für Chemie Chemical Monthly, 127(11):1189-1196 (1996).
Thompson T. A. and Wilding, G., Androgen antagonist activity by the antioxidant moiety of vitamin E, 2,2,5,7,8-pentamethyl-6-chromanol in human prostate carcinoma cells. Mol Cancer Ther. 2(8):797-803 (2003).
Tindall, D. et al., Symposium on androgen action in prostate cancer. Cancer Res. 64(19):7178-7180 (2004).
Trachtenberg, J. et al. Ketoconazole: a novel and rapid treatment for advanced prostatic cancer. J Urol. 130(1):152-153 (1983).
Trachtenberg, J., Ketoconazole therapy in advanced prostatic cancer, The Journal of Urology, 132(1):61-63 (1984).
Tunn, U.W. et al., Comparison of LH-RH analogue 1-month depot and 3-month depot by their hormone levels and pharmacokinetic profile in patients with advanced prostate cancer, 60(Suppl. 1): 9-17 (1998).
UK Examination report dated Sep. 27, 2013 for GB Application No. 1114153.8.
UK Examination report dated Oct. 8, 2014 for GB Application No. 1114153.8.
UK Examination report dated Nov. 21, 2014 for GB Application No. 1114153.8.
UK Examination report dated Nov. 21, 2014 for GB Application No. 1416433.9.
Vakatkar, V.V. et al., Cleavage of steriodal oximes, semicarbazones and thiosemicarbazones with titanous chloride under mild conditions, Abstract, Chemistry and Industry, Society of Chemical Industry, London, No. 17, p. 742 (1977).
Van Steenbrugge, G.J. et al., Transplantable human prostatic carcinoma (PC-82) in athymic nude mice. III. Effects of estrogens on the growth of the tumor tissue, The Prostate, 12(2):157-171 (1988).
Vasaitis, T. et al., The Effects of Novel Anti-Androgens on Androgen Receptor Action and Expression, Proceedings of the American Association for Cancer Research 47, Abstract 5340 (2006)http://aacrmeetingabstracts.org/cgi/content/abstract/2006/1/252-d.
Vehring. Pharmaceutical particle engineering via spray drying. Pharm Res. May 2008;25(5):999-1022. Epub Nov. 28, 2007.
Veldscholte, J. et al., Anti-androgens and the mutated androgen receptor of LNCaP cells: differential effects on binding affinity, heat-shock protein interaction, and transcription activation, Biochemistry, 31(8):2393-2399 (1992).
Vescio, R.A. et al., Cancer biology for individualized therapy: correlation of growth fraction index in native-state histoculture with tumor grade and stage, Proceedings of the National Academy of Sciences of the USA, 87(2):691-695 (1990).
Vippagunta, S. R. et al., Crystalline solids. Adv Drug Deliv Rev. 48(1):3-26 (2001).
Visakorpi, T. et al., In vivo amplification of the androgen receptor gene and progression of human prostate cancer, Nature Genetics 9(4):401-406 (1995).
Voets, M. et al., Heteroaryl-substituted naphthalenes and structurally modified derivatives: selective inhibitors of CYP11B2 for the treatment of congestive heart failure and myocardial fibrosis. J Med Chem. 48(21):6632-6642 (2005).
Wainstein M.A. et al., CWR22: androgen-dependent xenograft model derived from a primary human prostatic carcinoma, Cancer Research, 54(23):6049-6052 (1994).
Weintraub, P.M. et al., Chemical Abstract No. 116:214776V for EP 0469547, Chemical Abstracts Service, American Chemical Society, Columbus, OH, 116(22):778 (1992).
Weintraub, P.M. et al., Chemical Abstract No. 117 for EP0469-548 A2, Steroids, 117:985 (1992).
Wicha, J. and Masnyk, M., Cardiotonic Steroids, Part 8., Synthesis of 17beta-(3'-Pyridyl)-14beta-androst-4-ene-3beta, 14-diol from 17-Oxandrostane Derivatives, Bulletin of the Polish Academy of Sciences, Chemistry, 33(1-2):19-27 (1985).
Wilkinson, G.R., Chapter One: Pharmacokinetics, The Dynamics of Drug Absorption, Distribution, and Elimination, Goodman and Gilman's the Pharmaological Basis of Therapeutics, 10th Supp. Edition, 2 pages (2001).
Williams, G. et al., Objective responses to ketoconazole therapy in patients with relapsed progressive prostatic cancer, British Journal of Urology, 58(1):45-51 (1986).
Written Opinion for PCT/US2006/007143, 4 pages (Aug. 14, 2006).
Written Opinion for PCT/US2009/037610, 5 pages (Dec. 1, 2009).
Written Opinion for PCT/US2012/047253, 9 pages (Dec. 7, 2012).
Wu, J. and Kaufman, R.J., From acute ER stress to physiological roles of the Unfolded Protein Response, Cell Death & Differentiation, 13(3):374-384 (2006).
Yen, W.C. et al., Differential effect of taxol in rat primary and metastatic prostate tumors: site-dependent pharmacodynamics, Pharmaceutical Research, 13(9):1305-1312 (1996).
Yue, W. et al., A new nude mouse model for postmenopausal breast cancer using MCF-7 cells transfected with the human aromatase gene, Cancer Research, 54(19):5092-5095 (1994).
Yue, W., et al. Effect of aromatase inhibitors on growth of mammary tumors in a nude mouse model, Cancer Research, 55(14):3073-3077 (1995).
Zenger, M. et al., Structure-Activity Relationship and Drug Design, Remington's Pharmaceutical Sciences (Sixteenth Edition), Mack Publishing, Chapter 27: 420-425 (1980).
Zhang, J. et al. A small composite probasin promoter confers high levels of prostate-specific gene expression through regulation by androgens and glucocorticoids in vitro and in vivo. Endocrinology. 141(12):4698-4710 (2000).
Zheng, J.Y. and Fulu, M., Decrease of genital organ weights and plasma testosterone levels in rats following oral administration of leurpolide microemulsion, International Journal of Pharmaceutics, 307: 209-215 (2006).
Zhou, J.L. and Brodie, A., The effect of aromatase inhibitor 4-hydroxyandrostenedione on steroid receptors in hormone-dependent tissues of the rat, The Journal of Steroid Biochemistry and Molecular Biology, 52(1):71-76 (1995).
Zhuang, Q.Y. et al., [Effects of rapamycin on prostate cancer PC-3 cells], Ai Zheng, 28(8):851-5 (2009) [English Abstract Only].
Antonarakis, E.S. et al., AR-V7 and resistance to enzalutamide and abiraterone in prostate cancer, N. Engl. J. Med., 371(11):1028-38 (2014).
Author Not Known, A Study of Galeterone Compared to Enzalutamide in Men Expressing Androgen Receptor Splice Variant-7 mRNA (AR-V7) Metastatic CRPC (ARMOR3-SV), ClinicalTrials.gov, first received Mar. 19, 2015, last updated Mar. 16, 2016, 3 pages, retrieved online on Mar. 23, 2016: <https://clinicaltrials.gov/ct2/show/NCT02438007?term=galeterone&rank=1>.
Author Not Known, FDA approves Zytiga for late-stage prostate cancer, FDA Press Release of Apr. 28, 2001, U.S. Food and Drug Administration, 3 pages (2001) retrieved from the internet on Feb. 7, 2016 <http://www.fda.gov/NewsEvents/Newsroom/PressAnnouncements/ucm253055.htm>.
Author Not Known, Galeterone shows activity in a variant form of castration-resistant prostate cancer, European Cancer Organisation Report, www.ecco-org.eu, 3 pages (2014) retrieved from the internet on Feb. 17, 2016 <https://www.ecco-org.eu/Global/News/

(56) References Cited

OTHER PUBLICATIONS

ENA2014PR/2014/11/Galeteroneshowsactivityinavariantformofcastrationresistantprostatecancer>.

Cai, C. et al., Intratumoral de novo steroid synthesis activates androgen receptor in castration-resistant prostate cancer and is upregulated by treatment with CYP17A1 inhibitors, Cancer Res., 71(20):6503-13 (2011).

Castles, C.G. et al., Expression of a constitutively active estrogen receptor variant in the estrogen receptor-negative BT-20 human breast cancer cell line, Cancer Res., 53(24):5934-9 (1993).

Corbishley, T.P. et al., Androgen Receptor in Human Normal and Malignant Pancreatic Tissue and Cell Lines, Cancer, 57:1992-1995 (1986).

Dransfield, D.T. et al., Galeterone-induced Degradation of the Androgen Receptor Involves Inhibition of a Deubiquitnating Enzyme, ASCO-GU, Jan. 2016, Abstract #345, 1 page (2016).

Hall, P. F., Cytochrome P-450 C21scc: one enzyme with two actions: hydroxylase and lyase. J Steroid Biochem Mol Biol. 40(4-6):527-532 (1991).

International Search Report for PCT/US2014/050793, 4 pages (Jan. 12, 2015).

Jacoby, D.B. et al., Galeterone Shows Anti-Tumor Activity in Multiple Pre-Clinical Models that Express Androgen Receptor Splice Varients, Supporting Correlative Patient Data Seen in ARMOR2, AACR-NCI-EORTC International Conference on Molecular and Cancer Therapeutics, Abstract, 1 page (2015).

Jaworski, T., Degradation and beyond: control of androgen receptor activity by the proteasome system, Cell Mol. Biol. Lett., 11(1):109-31 (2006).

Li, Y. et al., Androgen receptor splice variants mediate enzalutamide resistance in castration-resistant prostate cancer cell lines, Cancer Res., 73(2):483-9 (2013).

Libertini, S.J. et al., Evidence for Calpain-Mediated Androgen Receptor Cleavage as a Mechanism for Androgen Independence, Cancer Res, 67(19):9001-9005 (2007).

Litvinov, I.V. et al., PC3, but not DU145, human prostate cancer cells retain the coregulators required for tumor suppressor ability of androgen receptor, Prostate, 66(12):1329-38 (2006).

Long, B.J. et al., Antiandrogenic effects of novel androgen synthesis inhibitors on hormone-dependent prostate cancer, Cancer Research, 60(23):6630-6640 (2000).

Maggiolini, et al. The mutant androgen receptor T877A mediates the proliferative but not the cytotoxic dose-dependent effects of genistein and quercetin on human LNCaP prostate cancer cells, Molecular Pharmacology, 62:1027-1035 (2002).

Njar, V.C. and Brodie, A.M., Discovery and development of Galeterone (TOK-001 or VN/124-1) for the treatment of all stages of prostate cancer, J. Med. Chem., 58(5):2077-87 (2015).

Purushottamachar, P. et al., Systematic structure modifications of multitarget prostate cancer drug candidate galeterone to produce novel androgen receptor down-regulating agents as an approach to treatment of advanced prostate cancer, J. Med. Chem., 56(12):4880-98 (2013).

Rathkopf, D. et al., Phase I dose-escalation study of the novel antiandrogen BMS-641988 in patients with castration-resistant prostate cancer, Clin. Cancer Res., 17(4):880-7 (2011).

Stanbrough, M. et al., Increased expression of genes converting adrenal androgens to testosterone in androgen-independent prostate cancer, Cancer Res., 66(5):2815-25 (2006).

Tepper, C.G. et al., Characterization of a Novel Androgen Receptor Mutation in a Relapsed CWR22 Prostate Cancer Xenograft and Cell Line, Cancer Research, 62:6606-6614 (2002).

Tran, C. et al., Development of a second-generation antiandrogen for treatment of advanced prostate cancer, Science, 324(5928):787-90 (2009).

Vasaitis, T. et al., Androgen receptor inactivation contributes to antitumor efficacy of CYP17 inhibitor VN/124-1 in prostate cancer, Molecular Cancer Therapeutics, 7(8): 2348-2357 (2008).

Vasaitis, T.S. et al., CYP17 inhibitors for prostate cancer therapy, J. Steroid Biochem. Mol. Biol., 125(1-2):23-31 (2011).

Veldscholte, J. et al., The androgen receptor in LNCaP cells contains a mutation in the ligand binding domain which affects steroid binding characteristics and response to antiandrogens, J. Steroid Biochem. Molec. Biol., 41(3-8): 665-669 (1992).

Written Opinion for PCT/US2014/050793, 7 pages (Jan. 12, 2015).

Zhou, Z.X. et al., The androgen receptor: an overview, Recent Prog. Horm. Res., 49:249-74 (1994).

* cited by examiner

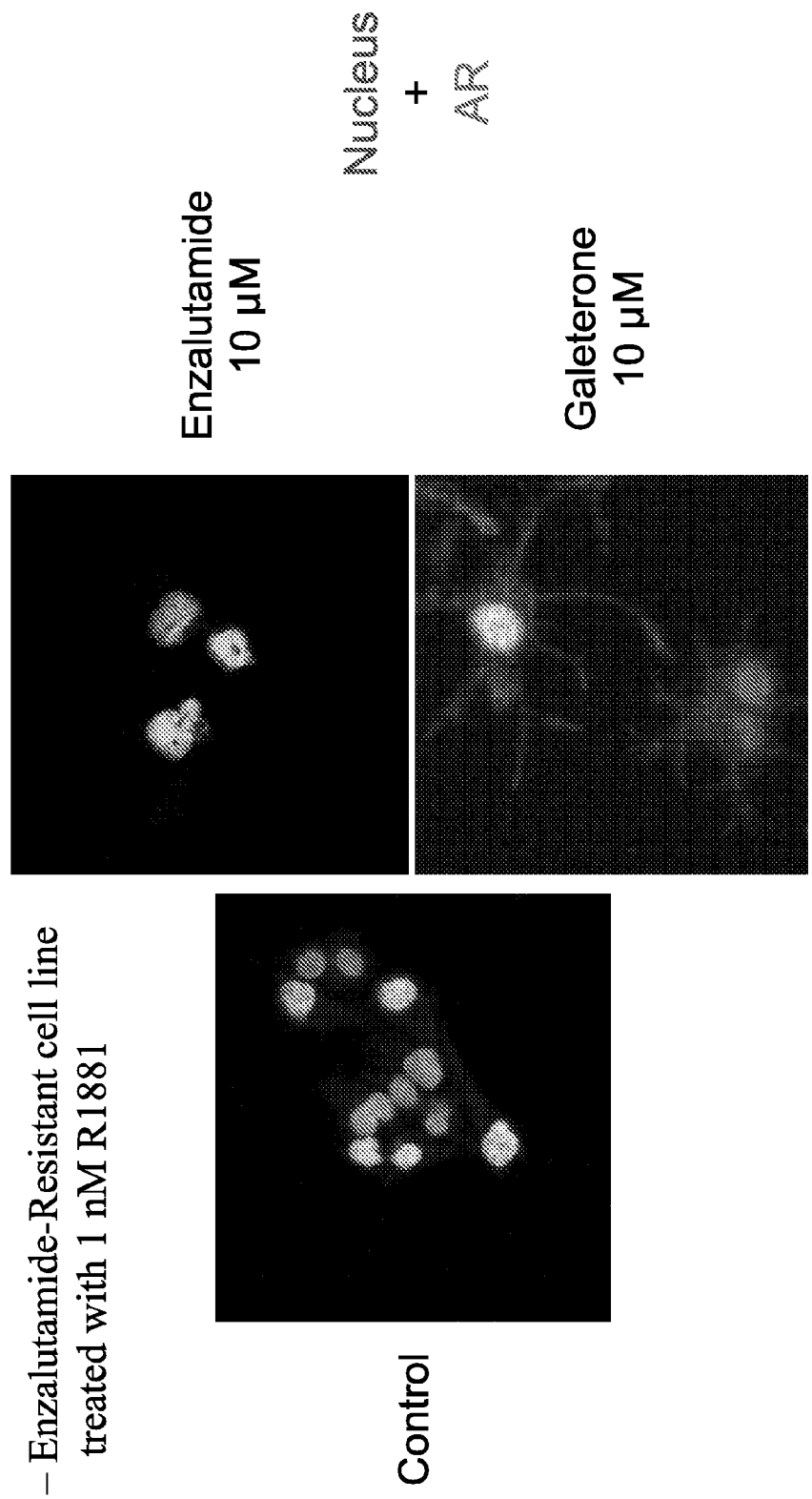

FIG. 18

| AR | IC50 (nM) |
|---|---|
| PC3-AR$_{wt}$ | 445 |
| LAPC4 (AR$_{wt}$) | 463 |
| LNCaP (T878A) | 576 |
| PC3-AR-W741C | 188 |
| PC3-AR-W741L | 980 |

BIOMARKERS FOR TREATMENT OF NEOPLASTIC DISORDERS USING ANDROGEN-TARGETED THERAPIES

CROSS-REFERENCE

This application claims the benefit of U.S. Provisional Application No. 61/865,038, filed Aug. 12, 2013, U.S. Provisional Application No. 61/990,570, filed on May 8, 2014, and U.S. Provisional Application No. 62/002,110, filed on May 22, 2014, which applications are incorporated herein by reference in their entirety.

BACKGROUND OF THE INVENTION

Cancer represents a significant burden on human health, accounting for an estimated 13% of all deaths each year. In particular, several common cancers and diseases are associated with androgen hormone signaling, such as, for example, prostate cancer, breast cancer, ovarian cancer, bladder cancer, pancreatic cancer, and polycystic ovary disease. For example, prostate cancer (PCa) is the second most common cancer in men. The majority of prostate cancer deaths are due to the development of metastatic disease that is unresponsive to conventional androgen deprivation therapy. Androgen deprivation therapy has been the standard of care in subjects with prostate cancer since the 1940s. Despite androgen deprivation, most subjects ultimately experience disease progression. For many years this later phase of the disease was called "hormone insensitive prostate cancer" or "androgen independent prostate cancer." It has since become clear that the prostate cancer that emerges after androgen deprivation therapy remains dependent upon androgen. The prostate cancer cells that have survived have gained the ability to import low levels of circulating androgens (expressed from adrenal glands), become much more sensitive to these low levels of testosterone, and actually synthesize testosterone within the prostate cancer cell itself. This stage of prostate cancer is now termed "castration resistant prostate cancer" or CRPC.

Identification of patients that are likely to respond or identification of those patients that are responding to therapy for prostate cancer is a goal for medical management of this disease. While current clinical guidelines are focused on symptoms, blood levels of prostate specific antigen (PSA), and imaging studies, other biological markers may be useful for clinical decision making. There remains a need for biomarkers of the disease and their relationship to identification of efficacy or toxicity of a therapeutic compound, and biomarkers which could provide information regarding identification of patients most likely to respond to therapeutic agents, or to identify patients receiving therapeutic agents who are not responding (either through primary or acquired resistance mechanisms), or to predict those patients that may develop undesirable side effects.

SUMMARY OF THE INVENTION

The biomarkers identified below may be used, for example, to evaluate treatment options at various points in the course of treatment of a patient. For example, the biomarkers are used in the evaluation of treatment options at various cancer treatment transition points by analysis of one ore more biomarkers or a biomarker panel to identify and optimize therapeutic choices. Biomarkers may also be used to predict unresponsiveness or poor responsiveness to existing anti-cancer therapy and responsiveness to galeterone in the same patient.

In one embodiment, biomarker detection is performed and correlated with galeterone efficacy in the treatment of prostate cancer.

A method of treating a disease in a patient in need thereof is provided, comprising: a) determining whether the disease is characterized by an altered form of androgen receptor; and b) if said altered form of androgen receptor is present, administering to said subject a pharmaceutical composition comprising a therapeutically effective amount of a compound of Formula I,

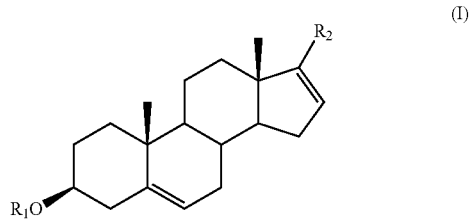

or a pharmaceutically acceptable salt, N-oxide, active metabolite, prodrug, or solvate thereof; wherein $R_1$ is H or acetyl; and $R_2$ is benzimidazole.

For example, $R_1$ is acetyl and the compound is a pro-drug of galeterone.

For example, $R_1$ is H and $R_2$ is benzamidazole and the compound is galeterone.

Provided herein is a method of treating a cancer in a patient in need thereof, comprising: a) obtaining a sample from said patient, for example a sample of circulating tumor cells; b) determining whether a truncated form of androgen receptor is present in the sample, for example ARV-7 or AR-V567es; and c) if said altered form of androgen receptor is present, administering to said subject a pharmaceutical composition comprising a therapeutically effective amount of a compound of Formula I,

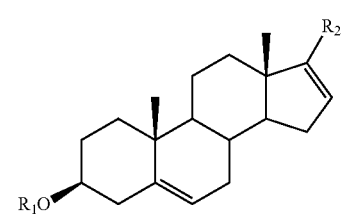

or a pharmaceutically acceptable salt, N-oxide, active metabolite, prodrug, or solvate thereof; wherein $R_1$ is H or acetyl; and $R_2$ is benzimidazole. For example, $R_1$ is hydrogen, $R_2$ is benzimidazole and the compound is galeterone. In some embodiments, the altered form of androgen receptor is a truncated AR lacking the ligand-binding domain, for example ARV-7. Said determining may include, for example, use of an antibody capable of binding to a ligand binding domain of the androgen receptor, such that absence of binding of the antibody results in absence of signal. Said determining may also include the use of two antibodies, for example one to the $NH_2$ terminal of the AR and one to the COOH terminal (ligand binding domain) of the AR to differentiate or generate a ratio of the presence of the NH2 terminal and absence of the COOH terminal (ligand binding). In a preferred embodiment, the analysis result is a ratio of antibody detection signals of the NH2 terminal and the C-terminal in the same subject sample. Said determining may also include detection of a truncated AR lacking the ligand binding domain by nucleic acid amplification, either quantitative or qualitative, or by a gene expression assay. In one embodiment, the detection of the truncated AR lacking the ligand binding domain is from a patient or subject sample, for example where the patient/subject sample has been enriched for circulating tumor cells. In another embodiment the patient/subject sample is enriched for circulating DNA. In yet another preferred embodiment, the patient/subject sample is a tumor biopsy or tissue sample.

In some embodiments, the disease is a prostate disease, for example prostate cancer. The prostate cancer may be resistant to castration. In some cases, the subject has undergone castration, for example chemical castration or surgical castration, or has undergone androgen receptor antagonist treatment or treatment to reduce nascent androgen production, such as interference with the steroidogenesis pathway, for example a CYP-17 lyase inhibitor, or combination therapy. In some embodiments, the disease is cancer, such as ovarian, bladder, pancreatic or breast cancer. The cancer may be resistant to an anti-androgen such as an androgen receptor antagonist, for example to enzalutamide or bicalutamide or ARN-509. The cancer may be resistant to a CYP17-lyase inhibitor, for example to abiraterone. The cancer may be resistant to a taxane, for example docetaxel or cabazitaxel. In some embodiments, the disease is androgen dependent.

The patient may be determined to have a mutated androgen receptor, for example a truncated AR such as AR-V1, AR-V2, AR-V3, AR-V4. AR-V5, AR-V567es, AR-V6, or AR-V7. The mutated AR can carry a point mutation such as T877A (T878A), D879G, (D878G), W741C, W741L, M749L, R629Q, G142V, P533S, T575A, H874Y, or F876L.

Also provided herein are methods of optimizing therapy of a disease in a patient in need thereof, comprising: identifying a patient undergoing treatment of a disease using a treatment regimen, wherein said treatment regimen comprises administration of a compound of Formula I:

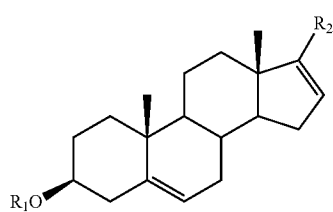

(I)

or a pharmaceutically acceptable salt, N-oxide, active metabolite, prodrug, or solvate thereof; wherein $R_1$ is H or acetyl; and $R_2$ is benzimidazole;
determining the status of at least one biomarker; and based on the determination of said biomarker, maintaining or modifying the therapy regimen. In a preferred embodiment, $R_1$ is hydrogen and $R_2$ is benzamidazole.

For example, the biomarker is the expression level or function of an androgen receptor, for example a wild-type or mutated AR. The mutated AR can be a splice variant and/or truncated AR, including AR-V1, AR-V2, AR-V3, AR-V4. AR-V5, AR-V567es, AR-V6, or AR-V7. Mutated AR can be AR with point mutations including, but not limited to, T877A (T878A), D879G (D878G), W741C, W741L, M749L, R629Q, G142V, P533S, T575A, H874Y, F876L.

In some embodiments, the disease is a prostate disease, for example prostate cancer. The prostate cancer may be resistant to castration. In some embodiments, the disease is cancer, such as ovarian, bladder, pancreatic or breast cancer. The cancer may be resistant to an anti-androgen such as an androgen receptor antagonist, for example to enzalutamide or bicalutamide or ARN-509. The cancer may be resistant to taxanes, for example docetaxel or cabazitaxel. In some cases, the subject has undergone castration or has undergone androgen receptor antagonist treatment, or both. In some embodiments, the disease is an androgen dependent disease.

The biomarker may also be a decrease in the number of circulating tumor cells (CTCs), for example wherein the number of circulating tumor cells is determined after at least 1 week of galeterone therapy. Suitable biomarkers include, but are not limited to: an increase in apoptotic CTCs; a decrease in PSA or a reduction in PSA doubling time; an increase in PSMA expression; a reduction in the tumor $^{18}$F-DHT-PET signal; a tissue biopsy based test, for example ProMark; the presence or expression of a proteosome degradation pathway member; a 5-kallikrein panel; the pre- and post-treatment testosterone blood level; a change in the level of at least one steroid after initiation of the treatment regimen; a metabolic marker, for example in the level of a P450 enzyme; a mutation or variant of a CYP17 protein; determination of a CTLA-4 blockade; a prostate health index; the presence or level of PCA3; the prostate core mitomic test; the presence of a mutation in a cell cycle progression gene; the level of hemoglobin, lactate dehydrogenase, or alkaline phosphatase, as determined by a serologic test; and resistance to chemotherapy (including enzalutamide or abiraterone, bicalutamide or ARN-509).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 15B describes the results of the experiment described in FIG. 15A and shows that galeterone, but not enzalutamide, reduces AR nuclear translocation.

FIG. 18 shows the results of a binding assay of galeterone to wild type AR and AR point mutants.

DETAILED DESCRIPTION OF THE INVENTION

Definitions

Figure 1:
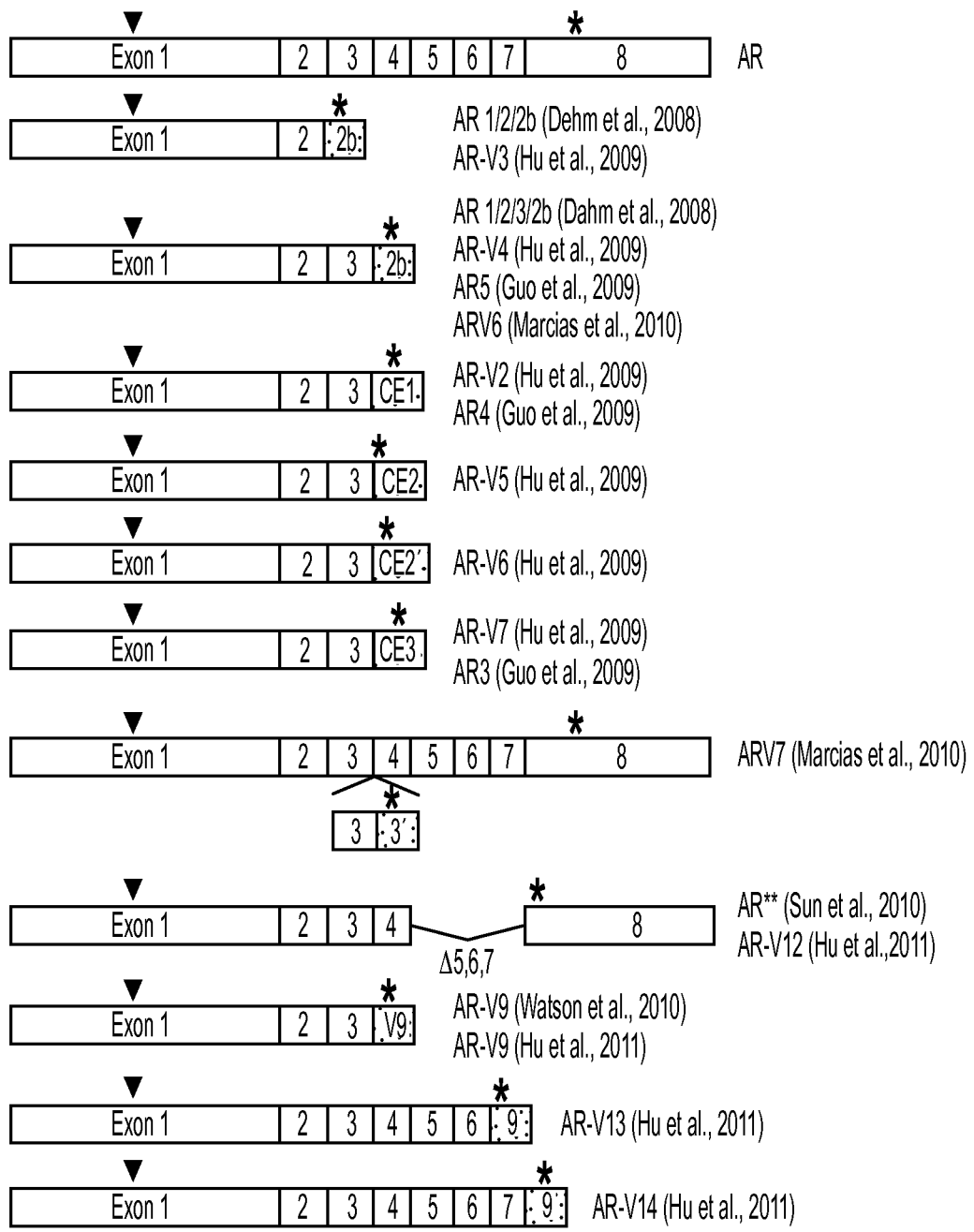
FIG. 1 depicts androgen receptor (AR) and alternative splice variants thereof.

A "subject" as used herein refers to a patient or subject in a clinical trial and more broadly a biological entity containing expressed genetic materials. Tissues (including biopsied materials), cells and their progeny from a subject obtained in vivo or cultured in vitro are also encompassed.

By "sample" is meant a fluid, solid, or tissue removed from a subject and includes whole blood, serum, plasma, tissue, semen, cell, biopsy, mucous, feces, bone, teeth, nasal or throat or cheek swab, urine, skin, tears, organ biopsy (liver, kidney, colon, lung, pancreas), tumor biopsy, or tumor tissue, circulating tumor cells, exosomes from the primary tumor or metastatic tissue. The sample may also include a portion of the collected fluid, solid, or tissue from a subject, for example a circulating tumor cell, or an analyte. By "processed sample" is meant the fluid, solid, or tissue from the subject is treated, handled, or managed via laboratory techniques to enrich for an analyte. By "processed whole blood sample" is meant that the whole blood sample is processed through in vitro laboratory techniques to analyze a component of the whole blood sample including cells, DNA, RNA, proteins, peptides, or an analyte as described below; for example, cells found in a whole blood sample may be enriched, washed, and analyzed separately; more specifically, circulating tumor cells may be enriched from a whole blood sample and analyzed for a biomarker or biomarkers, and these biomarkers may include a mutated form of androgen receptor. Another example is to enrich a whole blood sample for DNA (for example circulating DNA or tumor cell DNA) that can be analyzed for a biomarker or biomarkers and these biomarkers may include a mutated form of androgen receptor.

By "analyte" is meant a substance or a constituent of a sample to be analyzed. Exemplary analytes include one or more species of one or more of the following: a protein, a peptide, a polypeptide, an amino acid, a nucleic acid, an oligonucleotide, mRNA, RNA, microRNA, long non-coding RNA, DNA, circulating DNA, cDNA, an antibody, a carbohydrate, a polysaccharide, glucose, a lipid, a gas (e.g., oxygen or carbon dioxide), an electrolyte (e.g., sodium, potassium, chloride, bicarbonate, BUN, magnesium, phosphate, calcium, ammonia, lactate, zinc, citrate), a lipoprotein, cholesterol, a fatty acid, a glycoprotein, a proteoglycan, a lipopolysaccharide, a cell surface marker (e.g., CD3, CD4, CD8, IL2R, or CD35), a tumor marker (BCL-2, Ki-67, ERK5), prostate specific antigen (PSA), a cytoplasmic marker, a therapeutic agent, a metabolite of a therapeutic agent, a cell (e.g., a whole cell, a tumor cell, a circulating tumor cell, a stem cell, a white blood cell, a T cell (e.g., displaying CD3, CD4, CD8, IL2R, CD35, or other surface markers), or another cell identified with one or more specific markers). As used herein, the term "small molecule" refers to a drug, medication, medicament, or other chemically synthesized compound that is contemplated for human therapeutic use. As used herein, the term "biologic" refers to a substance derived from a biological source, not synthesized and that is contemplated for human therapeutic use. A biomarker is a biological substance that can be used as an indicator of a particular disease state or particular physiological state of an organism, generally a biomarker is a protein or other native compound measured in bodily fluid whose concentration reflects the presence or severity or staging of a disease state or dysfunction, can be used to monitor therapeutic progress of treatment of a disease or disorder or dysfunction, or can be used as a surrogate measure of clinical outcome or progression. As used herein, the term "metabolic biomarker" refers to a substance, molecule, or compound that is synthesized or biologically derived that is used to determine the status of a patient or subject's liver or kidney function. As used herein, the term "genotyping" refers to the ability to determine genetic differences in specific genes that may or may not affect the phenotype of the specific gene. As used herein, the term "phenotype" refers to the resultant biological expression, (metabolic or physiological) of the protein set by the genotype. As used herein, the term "gene expression profiling" refers to the ability to determine the rate or amount of the production of a gene product or the activity of gene transcription in a specific tissue, in a temporal or spatial manner. As used herein, the term "proteomic analysis" refers to a protein pattern or array to identify key differences in proteins or peptides in normal and diseased tissues. Additional exemplary analytes are described herein. The term analyte further includes components of a sample that are a direct product of a biochemical means of amplification of the initial target analyte, such as the product of a nucleic acid amplification reaction.

Combination Therapy: The term "combination therapy", as used herein, refers to those situations in which two or more different pharmaceutical agents are administered in overlapping regimens so that the subject is simultaneously exposed to two or more agents or administered in temporal regimens so that the subject is exposed to two or more agents in sequence.

Dosing Regimen: A "dosing regimen", as that term is used herein, refers to a set of unit doses (typically more than one) that are administered individually separated by periods of time. The recommended set of doses (i.e., amounts, timing, route of administration, etc.) for a particular pharmaceutical agent constitutes its dosing regimen.

Initiation: As used herein, the term "initiation" when applied to a dosing regimen can be used to refer to a first administration of a pharmaceutical agent to a subject who has not previously received the pharmaceutical agent. Alternatively or additionally, the term "initiation" can be used to refer to administration of a particular unit dose of a pharmaceutical agent during therapy of a subject.

Pharmaceutical agent: As used herein, the phrase "pharmaceutical agent" refers to any agent that, when administered to a subject, has a therapeutic effect and/or elicits a desired biological and/or pharmacological effect.

Pharmaceutically acceptable ester: As used herein, the term "pharmaceutically acceptable ester" refers to esters which hydrolyze in vivo and include those that break down readily in the human body to leave the parent compound or a salt thereof.

Therapeutically effective amount: The term "therapeutically effective amount" of a pharmaceutical agent or combination of agents is intended to refer to an amount of agent(s) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). A therapeutically effective amount is commonly administered in a dosing regimen that may comprise multiple unit doses. For any particular pharmaceutical agent, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular subject may depend upon a variety of factors including the disorder being treated and the severity of the disorder, the activity of the specific pharmaceutical agent employed; the specific composition employed; the age, body weight, general health, sex and diet of the subject; the time of administration, route of administration, and/or rate of excretion or metabolism of the specific pharmaceutical agent employed; the duration of the treatment; and like factors as is well known in the medical arts.

Treatment: As used herein, the term "treatment" (also "treat" or "treating") refers to any administration of a pharmaceutical agent, remedy, or medicament that partially or completely alleviates, ameliorates, relieves, inhibits, delays onset of, reduces severity of and/or reduces incidence of one or more symptoms or features of a particular disease, disorder, syndrome and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

As used herein, the term "unresponsiveness" or "poor responsiveness" refers to the lack of change of or minimal change of a patient's or subject's clinical or medical presentation, prognosis, symptoms, diagnostic indices, features, survival or outcomes after treatment and it further implies and infers that the treatment has not partially or completely alleviate, ameliorate, relieve, inhibit, delay onset of, reduce severity of and/or reduce incidence of one or more symptoms or features of a particular disease, disorder, syndrome and/or condition. Unresponsiveness can be used interchangeably with "lack of efficacy", "lack of response". Conversely, "response" or "responsiveness" to treatment refers to a change of a patient's clinical or medical presentation, prognosis, symptoms, diagnostic indices, features, survival or outcomes after treatment and it further implies and infers that the treatment has partially or completely alleviate, ameliorate, relieve, inhibit, delay onset of, reduce severity of and/or reduce incidence of one or more symptoms or features of a particular disease, disorder, syndrome and/or condition. Response may be used interchangeably with "efficacy" as the capacity of a treatment or remedy for producing a desired result or effect and is reflective of the quality of the treatment or remedy to produce the intended result. Thus, the biomarkers of the instant invention are used at assisting medical decision making. For example, during evaluation of a course of treatment, a sample is analyzed from the patient for a biomarker or a panel of biomarkers, determining the presence/absence or level of a biomarker or panel of biomarkers and then administering to the patient a compound of formula I or a compound of formula II based on the biomarker analysis result.

Unit dose: The term "unit dose" or "dose", as used herein, refers to a discrete administration of a pharmaceutical agent, typically in the context of a dosing regimen.

Definitions of standard chemistry terms may be found in reference works, including Carey and Sundberg "ADVANCED ORGANIC CHEMISTRY $4^{th}$ ED." Vols. A (2000) and B (2001), Plenum Press, New York, hereby incorporated by reference in its entirety. Unless otherwise indicated, conventional methods of mass spectroscopy, NMR, HPLC, protein chemistry, biochemistry, recombinant DNA techniques and pharmacology, within the skill of the art are employed.

Solid dispersion: The term "solid dispersion", as used herein, refers to composition comprising two different components, generally a solid matrix with a secondary substance (such as an active pharmaceutical ingredient) dispersed within.

Solid matrix: The term "solid matrix" refers to a solid phase in which molecules of a second substance (such as an active pharmaceutical ingredient) are embedded or dispersed within.

Methods of Treatment

Once prostate cancer is diagnosed and staged, clinical management options include expectant, regular, or interval management or surveillance, surgery, radiation therapy, cryosurgery, hormone therapy, chemotherapy, immunotherapy and vaccine treatment. Often the inclusion of age and expected life span and other concomitant health conditions are considered along with the stage and grade of the tumor in the treatment options. Since prostate cancer is an androgen-dependent disease, hormone therapy or androgen deprivation therapy (ADT) or androgen suppression therapy has the overall goal of reducing the levels of androgens in the body or to prevent them from reaching the prostate cancer cells (chemical castration). Hormone therapy includes LHRH agonists (Lupron, eligard, goserelin, tripterelin, histrelin); LHRH antagonists (firmagon). Hormone therapy may be used in conjunction with surgical resection of the tumor, orchietomy (surgical castration), or radiation therapy or radiopharmaceutical (Radium 223 Dichloride, Xofigo (Radium 223 Dichloride). Therapy aimed at reducing the production of androgens include abiraterone (a CYP17 inhibitor). Anti-androgen therapy is aimed at inhibiting the androgen receptor and examples are flutamide, bicalutamide, nilutamide, ARN-509 and enzalutamide. Anti-androgen treatment may be combined with orchiectomy or LHRH analogs as first-line hormone therapy. This is called combined androgen blockade (CAB). Other androgen suppressing drugs include estrogens and ketoconazole. Thus targeting the androgen receptor signaling pathway has been a drug development staple and broadly includes CYP17 inhibitors or modulators, antiandrogens, chaperone inhibitors (targeting heat shock proteins, Hsp-27 inhibitor), androgen-receptor modulator (blocking transactivation domain of the receptor). Vaccine treatment, currently Sipuleucel, is intended to boost the body's immune system to recognize the prostate tumor and lodge an anti-tumor immune response. This form of therapy is not "off the shelf" as each vaccine is made from the unique white cells from each individual patient after exposing in a lab to prostate acid phosphatase (PAP). Another immunotherapy includes ipilimumab (a CTLA-4 antagonist). Castration resistant prostate cancer (CRPC) is the term used for those patients for which androgen deprivation or androgen suppression therapy is no longer effective at slowing the proliferation of the prostate tumor or the metastasis, and it is a stage of the disease that is associated with primary or acquired resistance to therapy and for which there are few therapeutic options, one being broad cancer chemotherapy (docetaxel and cabazitaxel being examples).

Currently there are available the following compounds for use in treating patients with prostate cancer: Abiraterone Acetate, Bicalutamide, Cabazitaxel, Casodex (Bicalutamide), Degarelix, Docetaxel, Enzalutamide, Goserelin Acetate, Jevtana (Cabazitaxel), Leuprolide Acetate, Lupron (Leuprolide Acetate), Lupron Depot (Leuprolide Acetate), Lupron Depot-3 Month (Leuprolide Acetate), Lupron Depot-4 Month (Leuprolide Acetate), Lupron Depot-Ped (Leuprolide Acetate), Prednisone, Provenge (Sipuleucel-T), Radium 223 Dichloride, Sipuleucel-T, Taxotere (Docetaxel), Viadur (Leuprolide Acetate), Xofigo (Radium 223 Dichloride), Xtandi (Enzalutamide), Zoladex (Goserelin Acetate), Zytiga (Abiraterone Acetate).

Galeterone (the compound of Formula II), is being developed as a therapeutic for androgen-sensitive cancers. Galeterone has been shown to be a potent inhibitor of CYP17 lyase in the steroidogenic pathway and uniquely also to antagonize binding of androgens to the androgen receptor, and down-regulate the androgen receptor. The overall result of these effects on the androgen signaling pathway is the inhibition of prostate cancer growth. (See U.S. Pat. No. 7,875,599, incorporated herein by reference.)

Methods are provided herein to assist medical decision making in androgen dependent disease, disorders, syndromes, and conditions as a means to enhance the assessment and evaluation of, and optimize the predictive course of, treatment and to optimize the use of a compound of formula I and more preferably formula II. Methods are described and provided herein to identify patients that are more likely to respond to galeterone therapy or to identify patients who are not responding to the drug. By prospectively screening patients who are more likely to respond to the drug, galeterone, or a clinical evaluation of therapy options by analyzing a biomarker or biomarker panel from a patient sample, patients with prostate cancer will benefit because if selected as more likely to respond to galeterone, they may have a decreased risk of cancer progression and metastases and overall better outcomes. In addition, diagnostic methods that identify patients who are responding to the drug, galeterone, will benefit non-responsive patients as these same methods may identify those patients that could benefit from a switch to a different therapeutic approach far earlier than empiric therapeutic management. Due to its triad of mechanistic advantages, e.g. inhibiting the production of androgens, antagonizing and down regulating the androgen receptor activity, galeterone is a potential candidate of choice in cases where there is observed PCa therapy resistance. For example, if an antiandrogen has lost its ability to inhibit androgen receptor activity via the ligand binding site on the receptor, galeterone is a choice therapy as it has been shown to function as an anti-proliferative agent in antiandrogen resistant cells. Further, if a taxane has lost its ability to block cell division in a tumor cell or ablate proliferation of a tumor, galeterone is a potential candidate of choice therapy as it has the potential to be an anti-proliferative agent in taxane (for example docetaxel or cabazitaxel) resistant cells. Thus, identification of therapy resistance biomarkers may optimize selection of therapies known to be active by circumventing these resistance mechanisms.

Further, as PCa is a multifactorial disease, a biomarker for optimal galeterone therapy may be in the form of a panel of biomarkers or a biomarker panel that are indicators of disease status, therapeutic optimization, and outcomes. Galeterone may be prescribed alone or in combination with another therapy, thus a biomarker, biomarkers, or a biomarker panel can help predict utility, efficacy, safety, or toxicity and can help guide optimal medical decision making for not only galeterone alone, but galeterone in combination with other therapies.

Biomarkers can be prognostic, predictive, pharmacodynamic/mechanistic, or surrogate. Prognostic biomarkers are predictive of likely outcome of a disease independent of treatment. In PCa, prognostic biomarkers include PSA level, Gleason score, monitoring pattern of spread of disease, presence/absence/morphology/enumeration of CTCs, lactate dehydrogenase levels, and pain. Predictive biomarkers come in the form of a disease or host characteristic that may be involved in the improvement of outcomes with a particular treatment; for PCa predictive biomarkers include: PSA levels, when to biopsy, when to re-biopsy, when to start treatment and when to alter treatment. Pharmacodynamic biomarkers are able to reveal the mechanism of action or result of a pharmaceutical intervention, and in PCa these may include loss of androgen (testosterone or DHT), up or down regulation of AR specific gene expression (i.e. protein analysis), immune reactivity (detection of antibody or specific immune cells), PSA levels, or broadly, tumor shrinkage. Surrogate biomarkers are used to estimate the treatment effect as an intermediate endpoint for a gold standard outcome (eg. survival). In PCa, surrogate markers include CTC enumeration, PSA reduction, radiographic progression free survival. Overall, biomarkers pose a rational approach to addressing current clinical challenges including when and in which patient to biopsy or re-biopsy, offer interventional therapies (surgery and the like), or alter/combine therapies. Identifying a biomarker or a panel of biomarkers for companion use in galeterone therapy will provide powerful decision making capability to the therapeutic management of disease. While predictive and surrogate biomarkers carry a greater degree of importance in therapeutic management and decision making, either or both combined with prognostic biomarkers may provide even greater value to clinical management.

Prognostic factors for post-treatment include PSA decline relative to pretreatment levels, pain improvements, quality of life improvements (direct patient measure), changes in CTC count (for example greater than 5 to less than 5 per mL blood sample) and changes in CTC characterization (for example, size of CTCs), PSA Progression Free Survival (PFS), radiographic PFS, induction of immunity to tumor antigens (sipuleucel-T). PCa has a high propensity for bone metastasis and it is postulated that this is mediated through the acquisition of osteomimicry or adhesion molecules that allow attachment to the bone microenvironment. Agents such as zoledronic and denosumab may interfere with tumor bone stromal interactions and thus limit the skeletal related events (SREs) such as fractures, radiation/surgery to the bones, and spinal cord compression. Effects of PCa bone metastases can be indirectly related to bone turnover markers such as the bone type 1 collagen breakdown product N-telopeptide (urine/serum Ntx) and others such as tartrate-resistant acid phosphatase 5b, serum type 1 C telopeptide, osteopontin. Other biomarkers might include osteoclast activators such as bone alkaline phosphatase (BAP, or a component of total alkaline phosphatase), or broadly one or more of the OPG/RANKL/RANK system, a dominant, final mediator of osteoclastogenesis. Another clinical consequence of PCa is anemia brought on by bone marrow suppression. While anemia might be a consequence of androgen deprivation therapy, renal disease, chemotherapy toxicity, anemia of chronic disease, iron deficiency from blood loss, bone marrow infiltration or other co-existing disease, hemoglobin levels and anemia has been shown to be a prognostic factor in the nomogram CRPC risk-based classification (anemia, progression by bone scan, visceral metastases, pain). Anemia falls into the category of reflecting both burden of PCa as well as host response.

Another leading prognostic indicator of PCa is lactate dehydrogenase (LDH). Elevations of LDH are thought to be reflective of the underlying tumor burden or of an aggressive tumor phenotype. It is thought that LDH levels are useful for the clinical stratification of randomized patients in clinical trials and use for prognostic decision making.

Androgen receptor activity and gene expression profiling has been studied in prostate cancer. In seeking a biomarker, one begins with identifying an up-regulated gene and testing if this gene product can be a candidate biomarker. Gene expression profiling and linking the expression to mechanism of therapeutic resistance has been described by Holzbeierlein et al, Am. J. Path. 164(1), pp 217-227 2004. While enhanced or reduced expression of certain genes have been identified, genomic alterations in certain genes may also occur in prostate cancer and these include: rearrangement (ETS transcription factors, RAF, KRAS); mutation (androgen receptor, PIK3CA, AKT, RAF, KRAS); amplification (androgen receptor, PIK3CA, MYC, AURKA); loss (PTEN, RB 1). Other known genetic alterations occur in the SPOP, FOXA 1, AURKA, MED 12, MAGI-1 and CHD 1 genes. ETS fusions can be found it upwards of 50% of PCa and a targeted therapy or biomarker may be useful, for example targeting inhibition of PARP or DNAPK or analyzing patient samples for the ETS fusions. Oncogene expression, RAS/RAF, MYC, as well as the tumor suppressor gene RB 1 may be useful biomarkers.

Androgen receptor is known to regulate a large repertoire of genes central to the identity and behavior of prostate cancer cells. Overexpression of long non-coding RNA, for example PCGEM1 and PRNCR1, is associated and has been correlated with susceptibility of prostate cancer. Recently it was reported that both PCGEM1 and PRNCR1 are highly overexpressed in CRPC and they bind to and activate both ligand dependent and ligand independent AR-mediated gene activation programs and can lead to unchecked proliferation in prostate cancer cells. (Yang et al. Nature 2013, 500(7464): 598-602)

Prostate cancer biology varies from locally confined tumors with low risk for relapse to tumors with high risk for progression. Currently, few biomarkers are in use for patients with prostate cancer. For example, Gleason score and serum prostate specific antigen (PSA) levels are used separately to predict pathological stage in patients with localized prostate cancer. Because the degree of tumor differentiation has a profound influence on the expression of serum PSA, serum PSA levels alone do not reflect tumor burden accurately. CTC may have the potential to accurately and independently predict aspects of PCa and studies have linked identifying CTC to overall survival in CRPC. Other studies have pointed to the development of a panel of biomarkers such as a correlation of expression patterns of some biologically relevant proteins with clinically relevant scoring for example androgen receptor (AR) co-activators, lysine-specific histone demethylase 1 (LSD 1) and four and a half LIM-domain protein 2 (FHL2), AR, p53 along with Gleason score, Gleason grade and PSA levels.

Biomarkers for CRPC, a stage of PCa for which few therapeutic options exist, include: development of visceral metastatic disease (e.g. kidney, brain, intestine, pancreas, colon, lung, adrenal, breast, liver metastases), performance status, pain, hemoglobin, anemia, alkaline phosphatase (bone), pain, PSA and PSA by RT-PCR, PSA kinetics, CTC count, lactate dehydrogenase, albumin, type of progression (i.e. bone, measurable disease, or PSA elevation only), VEGF levels, IL-6 levels, chromagranin-A levels, serum TRAP-5b and other bone turnover markers (sCTX, P1NP, and others), Gleason sum in primary tumor, and urine N-telopeptide.

A biomarker or a biomarker panel is a measured characteristic, substance, or analyte or group of characteristics, substances or analytes that are objectively measured and evaluated as an indicator of normal biological processes, pathogenic processes, or pharmacologic responses to a therapeutic intervention. Cancer staging, including identification and/or localization of tumor, nodes, and or metastases (TNM), may the broadest clinical set of biomarkers. Biomarkers can be readily attained from patient samples for routine monitoring and thus biomarkers analyzed in whole blood, serum or plasma, urine, mucous, feces, tears, semen and the like are most easily obtainable. However, in some cases, biomarkers may be analyzed in patient samples that require more invasive procedures such as biopsy or tissue sampling for example tumor, bone, skin, teeth, organ biopsy (liver, kidney, colon, lung pancreas). Alternatively, circulating tumor cells or exosomes from prostate tumor or metastatic cells may be tested for biomarkers. Biomarkers include biological, physiological molecules, compounds, substances, or analytes and are analyzed to determine an absence/presence, level, concentration, value, intensity, activity, or measurement.

Employing the least invasive procedure to analyze a biomarker is most favorable, such as imaging methods and specific detection or evaluation employing imaging analyses may be employed, such as biomarker specific nanoparticles or magnetic nanoparticles, radioactive substances, or other tools to specifically image a biomarker in vivo. Biomarkers may be detected using standard methods known in the art, including: immunodetection, PCR (realtime PCR, RT-PCR, qPCR, Taq-Man PCR), chromatography, mass spectrometry, NMR and the like. Biomarkers stemming from gene expression assays using RNA isolated or derived from a patient or subject sample, may include RNA quantification, RNA QC and reverse transcription, DNase1 treatment and PCR based quantitative gene expression analysis and microRNA assays. The gene expression analysis may include high, medium or low density arrays or a combination of gene expression arrays, and these analyses are focused on allowing for analysis of gene expression pattern identification across many genes that are known to be induced by androgen receptor activation. Biomarkers may be characteristic of a pathogenic processes and may include a measurement of health quality of life, such as pain, ease and frequency of urination, sexual function, and the like.

Androgen Receptor and Androgen Receptor Variants as Biomarkers

The androgen receptor gene has a cytogenetic location at Xq12 and the molecular location on the X chromosome is at base pairs 67,544,031 to 67/730,618. Androgen receptor is currently understood to consist of 8 exons (see FIG. 1). Exon 1 encodes amino-terminal domain (NTD) containing transcriptional activation sites; exons 2-4 encode DNA-binding domain (DBD); while exons 5-8 encode a Ligand-binding domain (LBD). Alternative spliced variants exist, for example, lacking the LBD. Such variants may be constitutively active. A splice variant lacking the LBD may, for example, localize in the nucleus, where it binds DNA and activates transcription independently of ligands.

The androgen receptor gene contains two polymorphic trinucleotide microsatellites in exon 1. The first microsatellite (nearest the 5' end) contains 8 to 60 repetitions of the glutamine codon "CAG" and is thus known as the polyglutamine tract. The second microsatellite contains 4 to 31 repetitions of the glycine codon "GGC" and is known as the polyglycine tract. In the polyglutamine tract normally, the number of CAG repeats in the AR gene ranges from fewer than 10 to about 36 and in Caucasian men the average number is 21 and in Black men the average number is 18. In prostate cancer, some studies have shown an increased risk of prostate cancer in men with a short CAG repeat, and extra copies of the gene in cancer cells may be associated with progression of the disease. Spinal and bulbar atrophy (Kennedy's disease) results from an expansion of the CAG trinucleotide repeat in the AR gene. In Kennedy's disease, CAGs are abnormally repeated from 38 to more than 60 times. In breast cancer it has been suggested that a long CAG repeat region is associated with an increased risk of breast cancer in women, and that a shorter CAG repeat region is associated with a reduced risk. Other research indicates that a shorter CAG repeat region may be related to an increased risk of both breast cancer and benign breast disease. Shorter CAG repeat regions have also been associated with more aggressive forms of breast cancer. Further, a longer CAG repeat region in the AR gene may increase the risk of endometrial cancer in women. Although the extended CAG region changes the structure of the androgen receptor, it is unclear how the altered protein disrupts cells and androgen-AR mediated intracellular response. A fragment of the androgen receptor protein containing the CAG repeats appears to accumulate within cells and the accumulation may interfere with normal cell functions. This buildup may lead to apoptosis and in Kennedy's disease there is nerve cell loss in the brain and spinal cord that control muscle movement. In contrast, a prostate cancer cell, or a cell having low CAG repeats in the AR gene product, has circumvented the buildup of AR protein fragments by having low number of CAG repeats in the AR gene and hence a more likely process of AR protein expression and functionality. Thus, identification of the number of CAG repeats in the AR gene product may provide a formidable biomarker of androgen-dependent disease or therapy of androgen-dependent disease.

Prostate cancer is an androgen receptor dependent disease. Treatments, as described above, are often aimed at the androgen receptor, ligand binding to the receptor, or androgen mediated intracellular signaling pathways. PCa has been shown to circumvent these treatment pathways (resistance, resistance to treatment, treatment failure) by processes of selectivity and treatment pressures, to mutate the key proteins involved in the proliferation and "health" of the tumor. Mutations or genetic alterations may result in gain or loss of function, increased or decreased ligand binding, increased or decreased gene expression (changes or selectivity on gene expression of the androgen receptor itself or a gene product that is involved in steroid receptor activity), increase or decrease of steroid receptor DNA binding, receptor constitutive activity or loss of ligand responsivity, changes to the ability of the receptor to dimerize, changes to ligand binding sites on the effector proteins—e.g. cofactors become enhancers or inhibitors, antagonists become agonists, ligand promiscuity (e.g. progesterone, hydroxycortisone, estrogen, and cortisol under normal conditions do not bind the androgen receptor and ligand binding mutations within the androgen receptor may allow binding and activation by these other physiological relevant steroids). Thus, "altered" or "mutated" or "mutant" androgen receptor is used to refer to an androgen receptor which has changed relative to its wild-type form. For example, the altered androgen receptor phenotypically expresses one or more of the above described gain or loss of function. Changes include, but are note limited to splice variants including exon skipping, cryptic splicing donor/acceptor usage, and cryptic exon inclusion; amino acid substitution/s, deletion/s, or insertion/s; alterations of post transcription and/or post translation processing (i.e. glycosylation, folding, phosphorylation, ubiquinylation or the like).

Biomarkers for prostate cancer include the expression variants of the androgen receptor and known mutations have been found in established cell lines or from tumor biopsies. Mutations can be amino acid substitutions, insertions or deletions. Alternatively, there are splice variants that have been identified. Exemplary mutations include, for example, E43G, L54S, Q58L, L57Q, Q64R, ΔQ86, Q112H, G142V, E166S, K180R, L192F, Q198G, E211E, D221H, N222D, T227C, M266T, P269S, A251V, E253K, S296R, P334F, P340L, A356V, P390L, G414S, W433L, T438P, T438I, L444S, G449D, G451D, G456S, G457D, R484C, T497I, A498T, P499P, V508L, G524S, G524D, D528G, ΔL547, ΔP554, T573A, L574P, K580R, A586V, A587S, L594M, K609E, R629Q, K630T, S646D, S647N, E665D, Q670R, I672T, G683A, V716M, V715M, L701H, L720E, A721T, V730M, R726L, L744V, A748V, M749I, G750S, F754L, T755A, V757A, S759P, Y763C, W741C, F747L, N756A, V757I, R760K, W741X, ΔG743, W751X, S782N, R786X, W7960, L797P, Q798E, S791P, I799P, L830P, R846G, Q867X, H874Y, T877A, T877S, V866M, L880Q, L872P, D879G, M886I, A896T, Q902R, F891L, G909Q, Q919R, D890N, M895V, and K910R. For example, the amino acid substitutions are: T877A (T878A), D879G (D878G), W741C, W741L, M749L, R629Q, G142V, P533S, T575A, H874Y or, F876L. These point mutations may be categorized into the three main regions of the steroid receptor protein 1) LBD mutants (T877A, D879G, W741C. W741L, M749L, H874Y, F876L) and mutations in the LBD may have altered ligand binding due to receptor protein conformation changes or alterations in amino acid R groups in the ligand binding pocket or conformation resulting in loss of ligand binding, loss of ligand recognition, switching of antagonist to agonist, and/or ligand promiscuity; 2) NTD or hinge region mutants (R629Q, G142V, P533S) that may affect the ability of receptor transactivation, interaction with the transcription machinery or cofactors/regulators and result in alterations of receptor functions such as DNA binding, regulating gene expression, or nuclear translocation; or 3) DBD mutants (T575A) that may affect the receptor's ability to regulate of gene expression. Examples include: H874Y mutation in the androgen receptor has been shown to allow estradiol, progesterone, hydrocortisone, flutamide, and bicalutamide binding in 22Rv1 and CWR22RV1 cells; D878G has been shown to confer loss of DHT and testosterone binding and activity; W741C mutations confers bicalutamide and flutamide as agonists; F876L changes ARN-509 and enzalutamide from antagonists to agonists; M749L confers a hypersensitivity to estradiol; T575A leads to preferential binding to AR-nonspecific motifs, i.e. GRE; R629Q leads to gain of function with DHT.

Splice variants include exon skipping, cryptic splicing donor/acceptor usage, and cryptic exon inclusion. Variants that have been identified include AR-V1, AR-V2, AR-V3, AR-V4, AR-V5, AR-V6, ARV7, AR-V567es, AR-V7, AR-V9, AR-V12, AR-V13, and AR-V14. See, e.g. US Patent Application No. 2011/0110926, U.S. Pat. No. 8,133,724, and US Patent Application No. 2013/0130241). Generally, the androgen receptor variants are lacking some or all of the LBD and/or that portion of the carboxyl terminal of the androgen receptor protein that confers ligand binding.

In a clinical study of castrate resistant prostate cancer (Antonarakis E, Lu C, Wang H, et al. Androgen Receptor Splice Variant-7 Predicts Resistance to Enzalutamide in Patients with Castration Resistant Prostate Cancer. 2014 AACR Annual Meeting. Abstract 2910. Presented Apr. 7, 2014), 39% of patients expressed AR-V7 mRNA in circulating tumor cells. This subset of patients had a worse prognosis and worse response to anti-androgen treatment. Specifically, these patients showed no PSA decline when treated with enzalutamide and had shorter time to progression (2.1 months) relative to AR-V7 negative patients, for which PSA levels dropped by 50% in 53% of patients, and which had a longer time to progression (6.1 months). In some embodiments, the presence of the androgen AR-V7 variant correlates with resistance to anti-androgens such as enzalutamide (Efstathiou et al. European Urology 2014). In some embodiments, galeterone is administered to subjects identified to have tumors in which AR-V7 is expressed. In other embodiments, galeterone is administered to subjects identified to have tumors in which an androgen receptor is expressed which has a carboxy terminal loss.

Another variant known as AR-V12, has been shown to have about a 40% prevalence in androgen receptor positive metastatic samples. Since it has been proposed that nearly 60% of androgen receptor positive metastasis samples express one or more androgen receptor splice variants, it would follow that a large percentage of the tumors would then have the AR-V12 splice variant. Further, AR-V12 has been observed in samples from men that have demonstrated resistance to abiraterone (Mostaghel et al. 2011). The AR-V12 variant has been shown to be constitutively active, as it is lacking the ligand binding domain.

Another such variant is the AR point mutation T878A (alternatively "T877A"), which is reported in 33% of hormone-refractory tumors. This mutation increases the promiscuity of AR, allowing progesterone, which is elevated in patients treated with abiraterone, to activate AR-T878A. The tumor therefore continues to grow despite continued androgen blockade and abiraterone resistance can be conferred by expression of this mutant AR variant. The mutation also changes the binding specificity of the receptor such that in tumors carrying this mutation, flutamide acts as an agonist, while bicalutamide loses its activity. AR-T878A has a 6-fold increase in activity relative to wild type AR. In some embodiments, the presence of the androgen AR-T878A variant correlates with resistance to anti-androgens such as enzalutamide and abiraterone. In some embodiments, galeterone is administered to subjects identified to have tumors in which AR-T878A is expressed.

Another such variant is the AR point mutation F876L. This single amino acid mutation is within the AR LBD and it has shown to affect both enzalutamide and ARN-509 binding and ultimately potentially mediates tumor resistance to both compounds. The F876L mutation was identified in approximately 10% of ARN-509 treated patients. It has been postulated that the F876L mutation switches an antagonist to agonist effects and hence the mutation drives resistance to the anti-androgen compound.

In some embodiments, an AR variant is detected in a tumor sample isolated from a subject. For example, circulating tumor blood cells are isolated from the subject the cells are tested for the presence of the AR variant. In one embodiment, cells are tested for immunoreactivity of an antibody to bind the C-terminal portion (e.g. the ligand-binding domain) of the AR protein. For example, an antibody having specificity to the ligand-binding domain is used. Lack of immunoreactivity indicates the presence of an AR variant which lacks the ligand-binding domain, while presence of immunoreactivity indicates presence of an AR protein which possesses the ligand-binding domain, including the wild-type AR protein. The analysis can also be performed using an antibody specific to the NH2 portion of the AR protein, thus it can detect the presence of all AR proteins, whether they have a C-terminal truncation or not. In another embodiments, detection of the AR variant is performed by detecting the presence or level of a nucleic acid (including DNA or RNA) coding for the AR variant. Detection is performed, for example, by using a nucleic acid amplification reaction, a gene expression assay, or by using a sequencing-based method. In some embodiments, detection of ARV-7 is performed as described in US Patent Application NO. 2011/0110926, filed on Jan. 18, 2011, which is hereby incorporated by reference in its entirety. For example, PCR amplification of an RNA transcript is performed using primers designed to amplify the truncated ARV-7 transcript. In some embodiments, quantitative PCR amplification is performed.

Resistance to taxanes in PCa has been observed to be correlated with antiandrogen insensitivity. Further, taxanes have been shown to have a differential effect on prostate cancer cells that are expressing ARv567 vs ARv7, which are clinically relevant splice variants. ARv567, appearing in about 59% of prostate cancer tumor specimens from patients having CRPC and arises in response to ADT or abiraterone therapy, appears to have an effect on dynamic microtubules and the dynein motor protein. Hence the AR variant ARv567 is sequestered in the cytoplasm and thus is inactive in promoting transcription in the presence of taxane therapy. In contrast, ARv7 is present in both benign and malignant prostate tissues, but has been described as enriched in metastatic disease. In a recent study, ARv7, a variant that lacks the hinge region, did not co-sediment with microtubules or co-precipitate with dynein motor protein and both nuclear accumulation and transcriptional activity of ARv7 was unaffected by the presence of taxanes. (Thadani-Mulero et al. Cancer Res. 74(8):2270-2282) In some embodiments, galeterone is administered to subjects identified to have tumors resistant to taxanes by analyzing a biomarker in the subject for one or more AR mutants.

Abiraterone, a CYP17 inhibitor, reduces CRPC growth via suppression of intratumoral androgens. Resistance to abiraterone may occur through upregulation of CYP17A1 and/or induction of androgen receptor and AR splice variants that confer ligand independent signaling. In some embodiments, galeterone is administered to subjects identified to have tumors resistant to abiraterone.

Epithelial-mesenchymal transitions (EMTs) occur as key steps during embryonic morphogenesis, and are now implicated in the progression of primary tumors towards metastases. EMTs in prostate cancer are a reasonable candidate for progression to CRPC. Recent advances have fostered a more detailed understanding of molecular mechanisms and networks governing EMT in tumor progression. Besides TGFβ and RTK/Ras signaling, autocrine factors and Wnt-, Notch-, Hedgehog- and NF-κB-dependent pathways were found to contribute to EMT. Repression of E-cadherin by transcriptional regulators such as Snail or Twist emerges as one critical step driving EMT, and this stage is currently being molecularly linked with many of the new players. Increasing evidence suggests that EMT plays a specific role in the migration of cells from a primary tumor into the circulation and may provide a rationale for developing more effective cancer therapies or for understanding metastasis.

One of the main limitations in evaluating treatments for metastatic PCa is the inability to use available clinical imaging modalities to assess treatment response in bone, which is the predominant and often the only site of metastasis in 85% to 90% of patients. Traditional clinical assessment of bony metastases is achieved through radionuclide bone scintigraphy. Although the use of bone scintigraphy (bone scan), ultrasound, positron emission tomography (PET), (18)F-16beta-fluoro-5alpha-dihydrotestosterone ((18)F-FDHT) PET in prostate cancer patients undergoing therapy, computed tomography (CT), endorectal coil magnetic resonance imaging, and magnetic resonance imaging (MRI) plays a distinct role in identifying and characterizing the extent of disease. The use of diffusion MRI for assessing response to anticancer therapy is based on its ability to quantify the random or Brownian motion of water. Diffusion of water within a tumor is reduced in the presence of cellular membranes that act to impede the random motion of water molecules. During the course of successful treatment, loss of tumor cells and/or tumor cell membrane integrity occurs, which will then result in a reduction in the barriers that impede mobility of water molecules. Diffusion MRI can be used to assess the treatment effect through quantification of the amount of increased apparent diffusion coefficient (ADC) values in tumor regions experiencing a loss of cellular density. Thus, water mobility within a tumor will increase over time following effective treatment, as represented by an increase in MRI-quantified ADC values, with the magnitude of the change related to the effectiveness of the therapy. An alternative post-processing approach known as the functional diffusion map (fDM) was developed to standardize the processing of clinical diffusion MRI data to provide for a sensitive and quantifiable means for early assessment of cancer treatment outcome. The fDM approach of monitoring anticancer therapy allows spatial, voxel by voxel tracking of changes in tumor water diffusion values over time. Changes in diffusion values are depicted in fDM images by color encoding of tumor diffusion voxels that were altered due to therapy (either increased or decreased ADC value), thereby allowing for a spatially resolved analysis of ADC within an individual lesion.

By sampling blood and tumor biopsies, or using imaging techniques, it is possible to identify specific markers, e.g. one or more biologically relevant species that when analyzed have the potential to predict whether the patient will respond to galeterone. These biomarkers comprise molecular and cellular markers and include:

a. Genomic sequencing of specific genes within tumor cells or CTCs from a patient (ex. TP53, ZFHX3, RP1, PTEN, TMPRSS2 fusion, APC, wnt signaling, AR mutations and truncations, AR amplification, hepsin, PIM-1)

b. PTEN is a tumor suppressor gene that is involved in cell cycle regulation and is consistently associated with poor prognosis in PCa. Deletion of PTEN is associated with a higher Gleason grade, risk of progression, advanced localized or metastatic disease, and recurrence after therapy. Typically measured by fluorescence in situ hybridization (FISH), the test is typically ordered in conjunction with biopsy tests to indicate partial (hemizygous) or complete (homozygous) deletions of the gene c. Mutations in the androgen receptor:
   i. Point mutations leading to amino acid substitutions, including: T877A (T878A), D879G (D878G), W741C, W741L, M749L, R629Q, G142V, P533S, T575A, H874Y, F876L
   ii. Splice variants, including AR-V1, AR-V2, AR-V3, AR-V4, AR-V5, AR-V567es, AR-V6, AR-V7, ARV7, AR-V9, AR-V12, AR-V13, AR-V14. (see US2011/0110926, U.S. Pat. No. 8,133,724, US2013/0130241).

d. Circulating tumor cells (CTC)

e. Enumeration at baseline (circulating cells with the profile: CK+, CD45−) or at some time after initiation of therapy f. Enumeration of a sub-set of CTC which are small in size or by another cellular shape/size characteristic at baseline or at some time after initiation of therapy g. Enumeration of CK−, CD45− CTC candidates at baseline or at some time after initiation of therapy h. Androgen receptor (AR) expression in CTC or tumor biopsies at baseline or at some time after initiation of therapy i. Sub-cellular localization of AR protein in CTC or tumor biopsies (nuclear: cytoplasmic ratio) at baseline or at some time after initiation of therapy j. Assessing deletions and gene rearrangements in CTC and tumor biopsies by FISH (ex. PTEN deletion, TMPRSS2 fusions) at baseline or at some time after initiation of therapy k. TMPRSS2-ERG is a fusion between the transmembrane protease serine 2 gene and the v-ets erythroblastosis virus E26 oncogene homolog (avian (ERG) gene. This gene fusion is the predominant variant in approximately 40-80% of PCa. Quantitative levels of TMPRSS2-ERG in the urine appears to be associated with clinically significant PCa based on the Epstein criteria—a stratification of disease aggressiveness using PSA density and characteristics of the patient's biopsy (Gleason score), the % of tumor vs normal tissue observed, and number of cores with the tumor. TMPRRSS2-ERG detection combined with detection of PCA3 in urine has shown to have utility in predicting the severity of the PCa.

l. Absolute Prostate specific antigen (PSA) blood level and PSA doubling time prior to treatment m. Prostate specific membrane antigen (PSMA) expression as determined by imaging modalities such as radiolabeled ligands of PSMA or antibodies than bind PSMA.

n. 5 Kallikrein panel (total PSA, free PSA, intact PSA, Kallikrein 2)
o. Pre-treatment testosterone blood level
p. Changes in steroid levels at some time after initiation of therapy. Steroids include: androgens (testosterone, DHT), androgen precursors (DHEA, DHEA-Sulfate, androstenedione), corticosteroids, progestogens, mineralocorticoids, and androgen precursors in the "backdoor" pathway.
q. Staging of prostate tumor via Gleason Score (a biopsy grading scale from 1-5; lower Gleason grades are associated with small, closely packed glands and cells spread out and lose glandular architecture as Gleason grade increases)
r. Metabolic markers such as P450 enzymes that may be used to determine hi-, med-, low-metabolizers
s. CYP17 mutations that may change the efficacy of galeterone
t. Immune checkpoint blockade and immunologic approaches (CTLA-4 blockade)
u. Immune modulators, programmed death ligands 1 and 2 (PD-L1 and PD-L2) and their receptor, for example PD-1.
v. Prostate health index—a ratio of pro-PSA to free PSA
w. PCA3—a noncoding mRNA that has been shown to be elevated in >90% of men with PCa. PCA3 is measured in urine
x. Prostate core mitomic test—identifies a large-scale depletion in mitochondrial DNA that indicates cellular change associated with undiagnosed prostate cancer and detects the presence of malignant cells in normal appearing prostate tissue across an extended area.
y. CCP genes—cell cycle progression gene mutations
z. Serologic tests include: hemoglobin, lactate dehydrogenase (LDH), alkaline phosphatase.
aa. Cross reactivity in resistance—chemotherapy resistance and enzalutamide resistance appears to be common in CRPC therefore a biomarker that suggests chemotherapy resistance may also indicate a resistance to enzalutamide or to the broader class of anti-androgen compounds.

By sampling blood and tumor biopsies, or using imaging techniques, it may be possible to determine whether a patient is responding to galeterone therapy. Markers that are measured include:

a. Decrease in numbers of CTC (particularly after 1 week of galeterone therapy)
b. Increase in apoptotic CTC
c. Decrease in PSA or reduction in PSA doubling time
d. Increase in PSMA expression as determined by imaging modalities such as radiolabeled ligands of PSMA or antibodies than bind PSMA. Because blocking androgen-signaling results in an increase PSMA expression, an increase in the PSMA signal is an indicator of anti-androgen activity.
e. Reduction in the tumor $^{18}$F-DHT-PET signal, indicating antagonism of the androgen receptor
f. ProMark—a tissue biopsy based test—differentiation of indolent from aggressive disease in formalin-fixed, paraffin-embedded tissue samples.
g. Proteosome degradation pathway members—i.e. inhibition of the tagging or removal of the androgen receptor from the cell Described herein, in certain embodiments, are compounds, methods of making such compounds, pharmaceutical compositions and medicaments comprising such compounds, and methods of using such compounds to treat androgen receptor mediated diseases or conditions including, but not limited to, prostate cancer and benign prostatic hyperplasia. In some embodiments, the androgen receptor mediated disease or condition is prostate cancer. In some embodiments, the prostate cancer is castration resistant prostate cancer.

In some embodiments, the disease is an anti-androgen resistant disease. For example, the anti-androgen resistant disease may have previously been treated by providing an anti-androgen therapy, such as, e.g., castration, treatment with an androgen receptor antagonist, or a combination thereof. The disease may have initially responded to the anti-androgen therapy, but subsequently become insensitive to the therapy (e.g., worsened despite continued anti-androgen treatment). In some embodiments, the disease may have always been insensitive to the anti-androgen therapy.

In some embodiments, the disease is an androgen dependent disease and is marked by excessive production of adrenal or gonadal androgens by adrenal adenomas, carcinomas, or hyperplasia, Leydig cell tumors in men, and arrhenoblastomas and polycystic ovarian syndrome in women. Androgen dependent disease includes Kennedy's disease, breast cancer, prostate cancer, bladder cancer, pancreatic cancer, ovarian cancer, acne, hidradennitis suppurativa, androgenic alopecia, keratosis pilaris, begin prostatic hyperplasia, hisutism.

In some embodiments, the invention provides compounds, pharmaceutical compositions, and medicaments comprising such compounds, and methods of using such compounds that decrease androgen biosynthesis, decrease androgen receptor signaling and decrease androgen receptor sensitivity.

Also contemplated is a method of treating a disease by administering to a subject in need thereof a combination therapy comprising an anti-androgen therapy and a compound of Formula I, II, and/or III. The anti-androgen therapy can be, e.g., castration, treatment with an androgen receptor antagonist, e.g., enzalutamide, ARN-509, vinclozolin, procymidone, linuron, the DDT metabolite dichlorodiphenyldichloroethylene (p.p'-DDE), ketoconazole, fenitrothion, Di-n-butyl phthalate (DBP), diisobutyl phthalate (DiBP), benzyl butyl phthalate (BBP), Bis(2-ethylhexyl) phthalate (DEHP) and di-n-pentyl phthalate (DPP), Paraben esters, such as butylparaben, 3,3'-Diindolylmethane (DIM), *Scutellaria baicalensis*, N-butylbenzene-sulfonamide (NBBS), atraric acid, bicalutamide, flutamide, spironolactone, cyproterone acetate, finasteride, dutasteride, and nilutamide, docetaxel, cabazitaxel, a taxane, or any combination thereof.

In some embodiments, the compound of Formula I or formula II and the anti-androgen therapy are administered sequentially, simultaneously, alone, or in combination. In some embodiments, the compound of Formula I and the anti-androgen therapy (e.g., the androgen receptor antagonist) are formulated into the same pharmaceutical composition for administration to the subject.

In one aspect, the compounds, pharmaceutical compositions and medicaments comprising such compounds, and methods of using such compounds decrease androgen biosynthesis. In some embodiments, the compounds disclosed herein inhibit the activity of enzymes that controls androgen production. In certain embodiments, the compounds disclosed herein inhibit the activity of cytochrome $C_{17\alpha}$-hydroxylase/$C_{17-20}$-lyase (CYP17).

In one aspect, the compounds, pharmaceutical compositions and medicaments comprising such compounds, and methods of using such compounds decrease androgen receptor signaling. In some embodiments, the compounds disclosed herein bind to the AR and are a competitive inhibitor of testosterone binding.

In one aspect, the compounds, pharmaceutical compositions and medicaments comprising such compounds, and methods of using such compounds decrease androgen receptor sensitivity. In some embodiments, the compounds disclosed herein reduce the content of AR protein within the cell and diminish the ability of the cell to be sustained by low levels of androgenic growth signals.

Compounds

In one aspect, the invention provides compositions comprising a compound of Formula I

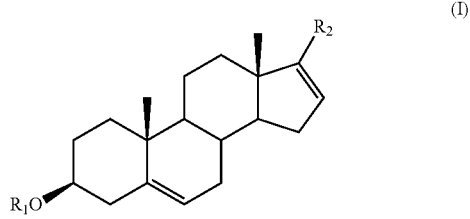

(I)

or a pharmaceutically acceptable salt, N-oxide, active metabolite, prodrug, or solvate thereof; wherein $R_1$ is H or acetyl; $R_2$ is pyridyl or benzimidazole.

In some embodiments, the compound is a compound of Formula II (also known as "galeterone"; "TOK-001"; or "VN/124-1"):

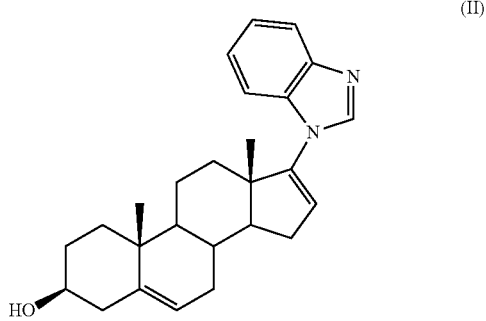 [SMILES: C[C@]12CC[C@H](O)CC1=CCC1C2CC[C@]2(C)C(n3cnc4ccccc43)=CCC12]

(II)

or a pharmaceutically acceptable salt, N-oxide, active metabolite, prodrug, or solvate thereof.

In other embodiments, the compound is a compound of Formula III:

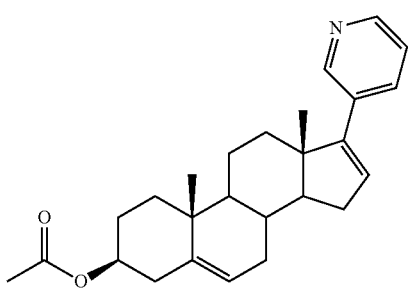 [SMILES: CC(=O)O[C@H]1CC[C@@]2(C)C(=CCC3C2CC[C@]2(C)C(c4cccnc4)=CCC32)C1]

or a pharmaceutically acceptable salt, N-oxide, active metabolite, prodrug, or solvate thereof;

The compounds of Formula I-III, pharmaceutically acceptable salts, pharmaceutically acceptable N-oxides, pharmaceutically active metabolites, pharmaceutically acceptable prodrugs, pharmaceutically acceptable polymorphs and pharmaceutically acceptable solvates thereof, modulate the activity of steroid hormone nuclear receptors and, as such, are useful for treating androgen receptor mediated diseases or conditions.

Exemplary Synthesis of the Compounds

Compounds of Formula (II) (also described as Compound (1) or 3-β-Hydroxyl 17-(1H-benzimidazol-1-yl)androsta-5, 16-diene) or TOK-001 or Galeterone) may be synthesized using standard synthetic techniques known to those of skill in the art or using methods known in the art in combination with methods described herein. Compounds of Formula (III) may be synthesized by similar methods. As one of skill in the art would understand, the solvents, temperatures and reaction conditions presented herein may vary according to the practice and knowledge of those of skill in the art.

The starting material used for the synthesis of the Compound (1) can be obtained from commercial sources, such as Aldrich Chemical Co. (Milwaukee, Wis.), Sigma Chemical Co. (St. Louis, Mo.), or the starting materials can be synthesized. The compounds described herein, and other related compounds having different substituents can be synthesized using techniques and materials known to those of skill in the art, such as described, for example, in March, ADVANCED ORGANIC CHEMISTRY 4th Ed., (Wiley 1992); Carey and Sundberg, ADVANCED ORGANIC CHEMISTRY 4th Ed., Vols. A and B (Plenum 2000, 2001), and Green and Wuts, PROTECTIVE GROUPS IN ORGANIC SYNTHESIS 3rd Ed., (Wiley 1999) (all of which are incorporated by reference in their entirety). General methods for the preparation of compounds as disclosed herein may be derived from known reactions in the field, and the reactions may be modified by the use of appropriate reagents and conditions, as would be recognized by the skilled person, for the introduction of the various moieties found in the formulae as provided herein.

Compounds of Formula I-III can be prepared as a pharmaceutically acceptable acid addition salt (which is a type of a pharmaceutically acceptable salt) by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid, metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

Compounds of Formula I-III can be prepared as a prodrug. Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they may be easier to administer than the parent drug. Prodrugs may, for instance, be bioavailable by oral administration whereas the parent is not. The prodrug may also have improved solubility in pharmaceutical compositions over the parent drug. An example, without limitation, of a prodrug would be a derivative of Formula (I-III), which is administered as a hydrophilic ester (the "prodrug") to facilitate absorption in the gastrointestinal tract where improved water solubility is beneficial, but which then is metabolically hydrolyzed to a carboxylic acid and the active entity, Formula (I-III). A further example of a prodrug is a short peptide bonded to the hydroxyl group of Compound (1), wherein the peptide is metabolized to provide a compound of Formula I, II, or III.

Prodrugs may be designed as reversible drug derivatives for use as modifiers to enhance drug transport to site-specific tissues. The design of prodrugs to date has been to increase the effective water solubility of the therapeutic compound for targeting to regions where water is the principal solvent. See, e.g., Fedorak et al., *Am. J Physiol.*, 269:G210-218 (1995); McLoed et al., *Gastroenterol*, 106:405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J Pharmaceutics*, 47, 103 (1988); Sinkula et al., *J. Pharm. Sci.*, 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein in their entirety.

Additionally, prodrug derivatives of compounds of Formula I-III can be prepared by methods known to those of ordinary skill in the art (e.g., for further details see Saulnier et al., (1994), Bioorganic and Medicinal Chemistry Letters, Vol. 4, p. 1985). Prodrug forms of the herein described compounds, wherein the prodrug is metabolized in vivo to produce a derivative as set forth herein are included within the scope of the claims. Indeed, some of the herein-described compounds may be a prodrug for another derivative or active compound.

Sites on the aromatic ring portion of compounds of Formula I-III can be susceptible to various metabolic reactions, therefore incorporation of appropriate substituents on the aromatic ring structures, for example, halogens, can reduce, minimize or eliminate this metabolic pathway.

Various methods of making compounds of Formula I-III are contemplated and the following descriptions are provided as non-limiting examples. In some embodiments, one or more of the following chemical reactions is performed in an inert atmosphere, for example, nitrogen or argon. In some embodiments, the temperature of the reaction is monitored. In some embodiments, the reaction is monitored by HPLC or TLC. In some embodiments, the pH of the reaction is monitored. In some embodiments, the temperature of the reaction is controlled. In some embodiments, the purity of the product is determined by HPLC. In some embodiments, the experiments are run on small scale, medium scale, large scale, analytical scale, or manufacturing scale. In some embodiments, the product is clarified by filtration through a pad comprising one or more of silica gel and celite.

In some embodiments, the synthesis is performed on large scale. In some embodiments, large scale comprises a scale of about 1 to about 10 kg. In some embodiments, the synthesis is performed on manufacturing scale. In some embodiments, manufacturing scale comprises a scale of greater than about 10 kg. In some embodiments, manufacturing scale comprises a scale of about 10 to about 1,000 kg. In some embodiments, manufacturing scale comprises a scale of about 10 to about 100 kg. In some embodiments, manufacturing scale comprises a scale of about 10 to about 50 kg. In some embodiments, manufacturing scale comprises a scale of about 33.4 kg.

In some embodiments, an experiment is performed on a smaller scale to gather information to be used to plan or perform synthesis on a manufacturing scale. In some embodiments, the results obtained on the smaller scales are expected to be reproducible on manufacturing scale. In some embodiments, the results obtained on smaller scales are not expected to be reproducible on manufacturing scale. In some embodiments, the yields obtained on manufacturing scale are greater than the yields obtained on smaller scales. In some embodiments, the yields obtained on manufacturing scale are lesser than the yields obtained on smaller scales.

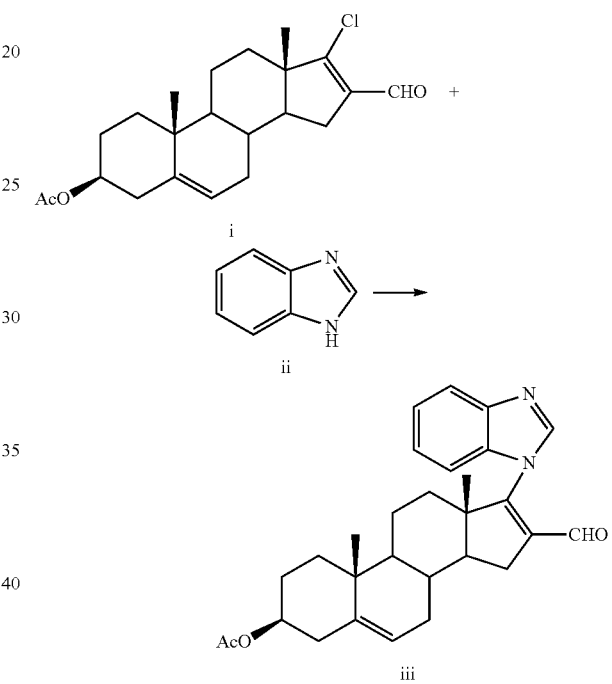

In one embodiment, a solution of a compound of Formula i in a solvent is prepared. A compound of Formula ii is then contacted to the solution, and the resultant mixture is heated in the presence of a base for a period of time sufficient to provide a compound of Formula iii. In some embodiments, the period of time is about 1 hour, about 2 hours, about 4 hours, about 8 hours, about 12 hours, or about 24 hours. In some embodiments, the time is from about 1 hour to about 24 hours. In some embodiments, the base comprises lithium carbonate, sodium carbonate, potassium carbonate, sodium bicarbonate, a sodium phosphate, or a potassium phosphate. In some embodiments, the solvent comprises DMF. In some embodiments, the temperature is about 50° C., about 70° C., about 100° C., about 150° C., or a temperature effective to sustain reflux conditions. In some embodiments, the temperature is from about 50° C. to about 200° C. The compound of Formula iii can be isolated from the reaction mixture and purified by any method known to one of skill in the art. Such methods include, but are not limited to, pouring an aqueous mixture into the reaction mixture, thereby effecting the precipitation of compound iii as a solid. The isolated compound of Formula iii may optionally be purified by any method known to one of skill in the art. Such methods include, but are not limited to, trituration with water.

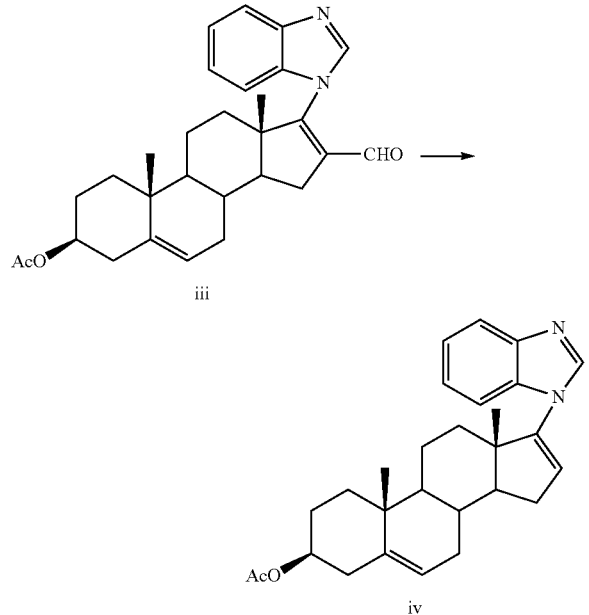

iii iv

In one embodiment, a solution of a compound of Formula iii in a solvent is prepared, and the solution is contacted with a catalyst for a period of time sufficient to provide a compound of Formula iv. In some embodiments, the period of time is about 1 hour, about 2 hours, about 4 hours, about 8 hours, about 12 hours, or about 24 hours. In some embodiments, the time is from about 1 hour to about 24 hours. In some embodiments, the catalyst comprises palladium on carbon, platinum on carbon, a transition metal salt, or a transition metal complex. In some embodiments, the solvent comprises N-methylpyrrolidone. In some embodiments, the temperature is about 50° C., about 70° C., about 100° C., about 150° C., about 190° C., about 200° C., or a temperature effective to sustain reflux conditions. In some embodiments, the temperature is from about 50° C. to about 250° C. The compound of Formula iv can be isolated from the reaction mixture and purified by any method known to one of skill in the art. Such methods include, but are not limited to, in-line filtration. The isolated compound of Formula iv may optionally be purified by any method known to one of skill in the art.

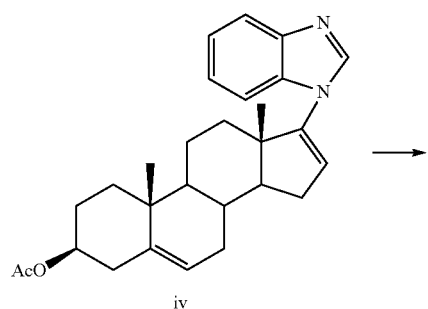

iv

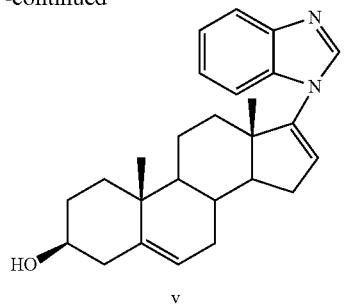

v

In one embodiment, a solution of a compound of Formula iv in a solvent is prepared, and the solution is contacted with a base for a period of time sufficient to provide a compound of Formula v (i.e., Compound (1)). In some embodiments, the period of time is about 1 hour, about 2 hours, about 4 hours, about 8 hours, about 12 hours, or about 24 hours. In some embodiments, the time is from about 1 hour to about 24 hours. In some embodiments, the base comprises lithium hydroxide, sodium hydroxide, potassium hydroxide, sodium methoxide, potassium methoxide, sodium ethoxide, potassium ethoxide, lithium carbonate, sodium carbonate, potassium carbonate, sodium bicarbonate, a sodium phosphate, or a potassium phosphate. In some embodiments, the solvent comprises water, methanol, ethanol, 2-propanol, t-butanol, or mixtures thereof. In some embodiments, the solvent comprises methanol and the base comprises sodium methoxide. In some embodiments, the temperature is about 35° C., about 50° C., about 70° C., about 100° C., or a temperature effective to sustain reflux conditions. In some embodiments, the temperature is from about 25° C. to about 100° C. The compound of Formula v can be isolated from the reaction mixture and purified by any method known to one of skill in the art. Such methods include, but are not limited to, extraction. The isolated compound of Formula v may optionally be purified by any method known to one of skill in the art. Such methods include, but are not limited to, trituration.

Exemplary Pharmaceutical Compositions/Formulations

A pharmaceutical composition, as used herein, refers to a mixture of a compound of Formula I with other chemical components, such as carriers, stabilizers, diluents, dispersing agents, suspending agents, thickening agents, and/or excipients. The pharmaceutical composition facilitates administration of the compound to an organism. Pharmaceutical composition containing a compound of Formula I can be administered in therapeutically effective amounts as pharmaceutical compositions by any conventional form and route known in the art including, but not limited to: intravenous, oral, rectal, aerosol, parenteral, ophthalmic, pulmonary, transdermal, vaginal, otic, nasal, and topical administration.

One may administer the compound in a local rather than systemic manner, for example, via injection of the compound directly into an organ, often in a depot or sustained release formulation. Furthermore, one may administer pharmaceutical composition containing a compound of Formula I in a targeted drug delivery system, for example, in a liposome coated with organ-specific antibody. The liposomes will be targeted to and taken up selectively by the organ. In addition, the pharmaceutical composition containing a compound of Formula I may be provided in the form of a rapid release formulation, in the form of an extended release formulation, or in the form of an intermediate release formulation. In some embodiments, the extended release formulation releases the compound for over 1 hour, over 2 hours, over 3 hours, over 4 hours, over 6 hours, over 12 hours, over 24 hours, or more. In some embodiments, the extended release formulation releases the compound at a steady rate for over 1 hour, over 2 hours, over 3 hours, over 4 hours, over 6 hours, over 12 hours, over 24 hours, or more.

For oral administration, a compound of Formula I can be formulated readily by combining the active compounds with pharmaceutically acceptable carriers or excipients well known in the art. Such carriers enable the compounds described herein to be formulated as tablets, powders, pills, dragees, capsules, liquids, gels, syrups, elixirs, slurries, suspensions and the like, for oral ingestion by a subject to be treated. Generally, excipients such as fillers, disintegrants, glidants, surfactants, recrystallization inhibitors, lubricants, pigments, binders, flavoring agents, and so forth can be used for customary purposes and in typical amounts without affecting the properties of the compositions.

Non-limiting examples of fillers include lactose monohydrate, microcrystalline cellulose, mannitol, xylitol, calcium diphosphate, and starch.

Non-limiting examples of disintegrants include croscarmellose, sodium starch glycholate, crospovidone, sodium alginate, methyl cellulose, and carboxymethyl cellulose sodium.

Non-limiting examples of glidants include magnesium stearate, colloidal silicon dioxide, starch and talc.

Non-limiting examples of surfactants include sodium lauryl sulfate, sorbitan esters, poloxamers, PEG block copolymers, and polysorbates.

Non-limiting examples of recrystallization inhibitors include poloxamer 188, poloxamer 407, Povidone K-90, or hypromellose.

Non-limiting examples of lubricants include magnesium stearate and calcium stearate Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. In some embodiments, the capsule comprises a hard gelatin capsule comprising one or more of pharmaceutical, bovine, and plant gelatins. In certain instances, a gelatin is alkaline processed. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal or sublingual administration, the compositions may take the form of tablets, lozenges, or gels formulated in conventional manner. Parental injections may involve for bolus injection or continuous infusion. The pharmaceutical composition of Compound (1) may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compositions described herein can be administered topically and can be formulated into a variety of topically administrable compositions, such as solutions, suspensions, lotions, gels, pastes, medicated sticks, balms, creams or ointments. Such pharmaceutical composition can contain solubilizers, stabilizers, tonicity enhancing agents, buffers and preservatives.

Formulations suitable for transdermal administration of compounds having the structure of Formula (1) may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of a compound of Formula I can be accomplished by means of iontophoretic patches and the like. Additionally, transdermal patches can provide controlled delivery of a compound of Formula I. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

For administration by inhalation, the compositions of the present invention may be in a form as an aerosol, a mist or a powder. Pharmaceutical compositions of Formula (I) are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, such as, by way of example only, gelatin for use in an inhaler or insufflator may be formulated containing a powder mix of the compound and a suitable powder base such as lactose or starch.

The compound of Formula I may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In practicing the methods of treatment or use provided herein, therapeutically effective amounts of a compound of Formula I provided herein are administered in a pharmaceutical composition to a mammal having a disease or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

Pharmaceutical compositions may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. Pharmaceutical compositions comprising a compound of Formula (I) may be manufactured in a conventional manner, such as, by way of example only, by means of conventional mixing, dissolving, granulating, dragee-making, levigating, emulsifying, encapsulating, entrapping or compression processes.

The pharmaceutical compositions can include at least one pharmaceutically acceptable carrier, diluent or excipient and a compound of Formula (I) described herein as an active ingredient in free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The compositions may be in liquid solutions or suspensions, solid forms suitable for solution or suspension in a liquid prior to use, or as emulsions. These compositions may also contain minor amounts of nontoxic, auxiliary substances, such as wetting or emulsifying agents, pH buffering agents, and so forth.

In some embodiments, the pharmaceutical composition is a solid dispersion delivery system.

In some embodiments, the solid dispersion delivery system comprises hydroxypropyl methylcellulose (HPMC).

In some embodiments, the solid dispersion delivery system comprises hydroxypropyl methylcellulose phthalate (HPMCP).

In some embodiments, the solid dispersion delivery system comprises hydroxypropyl methylcellulose acetate succinate (HPMCAS).

In some embodiments, the solid dispersion delivery system comprises Poloxamer 188.

In some embodiments, the solid dispersion delivery system comprises Poloxamer 407.

In some embodiments, the solid dispersion delivery system comprises Povidone K-90.

In some embodiments, the pharmaceutical composition is a physical mixture.

A summary of types of pharmaceutical compositions may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N. Y., 1980; and *Pharmaceutical Dosage Forms and Drug Delivery Systems*, Seventh Ed. (Lippincott Williams & Wilkins 1999), each of which is incorporated by reference herein in its entirety.

Spray Dried Compositions and Methods

In some embodiments, the present invention provides solid dispersion compositions comprising a compound of Formula I:

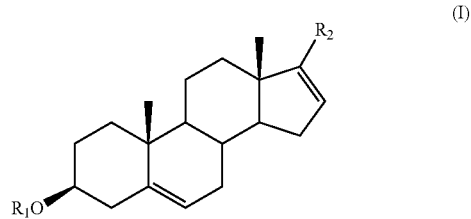

or a pharmaceutically acceptable salt, N-oxide, active metabolite, prodrug, or solvate thereof; wherein $R_1$ is H or acetyl; $R_2$ is pyridyl or benzimidazole; and a solid matrix. In some embodiments, the compound of Formula I is dispersed in said solid matrix.

In some embodiments, the solid matrix is comprised of a polymer. In some embodiments, the polymer is a water soluble polymer. Non-limiting examples of water soluble polymers used in solid dispersions include hydroxypropyl methyl cellulose (HPMC), polyvinylpyrrolidone (PVP block copolymers of ethylene oxide and propylene oxide ((K-25, 50 30, 90; PVP), hydroxypropyl cellulose (HPC), methyl cellulose (MC), and polyethyleneglycol (PEG). In other embodiments, the polymer is soluble in an aqueous solution. In particular embodiments, the polymer is soluble in an aqueous solution which has a pH of 5.5 or greater. Non-limiting examples of polymers soluble in aqueous solutions of pH 5.5 or greater include sodium carboxymethylcellulose (NaCMC, sodium cellulose glycolate) and hydroxypropylmethyl cellulose acetate succinate (HPMCAS). Other non-limiting examples of polymers suitable for use in solid dispersions include, e.g., of 3,4-dimethyl-phenomethylcarbamate (MPMC), hypromellose phthalate (HPMCP), Poloxamer 188, Poloxamer 407, Povidone K-90, poly(meth)acrylates (Eudragit), homopolymers of N-vinyl-2-pyrrolidone, povidone, copovidone (Plasdone), carboxymethylethylcellulose (CMEC), cellulose acetate phthalate (CAP), methacrylic copolymer LD (L30 D55), methacrylic copolymer S (S-100), aminoalkyl methacrylate copolymer E (gastric coating base), poly(vinyl acetal) diethylaminoacetate (AEA), ethylcellulose (EC), methacrylic copolymer RS (RS 30D), polyvinyl alcohol (PVA), hydroxypropylmethylcellulose (HPMC), HPMC 2208 (Metolose 90SH), HPMC 2906 (Metolose 65SH), HPMC (Metolose 60SH), dextrin, pullulan, Acacia, tragacanth, sodium alginate, propylene glycol alginate, agar powder, gelatin, starch, processed starch, phospholipids, lecithin, glucomannan, polyethyleneglycol (PEG) cellulose acetate trimellitate (CAT), hydroxypropyl methyl cellulose acetate trimellitate (HPMCAT), and carboxymethylcellulose acetate butyrate (CMCAB).

In some embodiments, the solid dispersion of the compound in matrix can be prepared by forming a homogeneous solution or melt of the drug and polymer, followed by solidifying the mixture, resulting in a solid composition of the compound dispersed in the solid matrix. In some embodiments, preparation of the solid dispersion comprises forming a homogenous solution comprising the compound, the polymer, and a solvent, followed by solidifying the mixture by removal of the solvent. In some embodiments, the solvent is an organic solvent or a mixture of more than one organic solvent. Non-limiting examples of organic solvents include dimethylformamide (DMF), acetone, methanol, ethanol, ethyl acetate, tetrahydrofuran, n-propanol, iso-propanol, butanol, methyl ethyl ketone, methyl iso-butyl ketone, propylacetate, acetonitrile, methylene chloride, toluene, 1,1,1-trichloroethane, dimethylacetamide, and dimethylsulfoxide. In particular embodiments, the solvent is methanol, ethanol, ethyl acetate, acetone, tetrahydrofuran, 2:1 acetone: methanol, 2:1 methanol: tetrahydrofuran, 2:1 methanol: acetone, 6:1 DMF: water, 14:7:2:1 acetone: methanol: DMF: water, 4:1:1 methanol: water: acetone, 8:1 ethanol: water.

Methods for removing the solvent from the mixture are known in the art, and can include freeze-drying, vacuum drying, spray-drying, or combinations thereof.

In particular embodiments, the solvent is removed by spray-drying. The term "spray-drying" generally broadly refers to atomizing the solution into a spray of small droplets and rapidly removing solvent from the droplets using a spray-drying apparatus that facilitates rapid evaporation of solvent from the droplets. Spray-drying processes and spray-drying equipment are described generally in Perry's Chemical Engineers' Handbook, pages 20-54 to 20-57 (Sixth Edition 1984). Solvent evaporation can be facilitated by, e.g., maintaining the pressure in the spray-drying apparatus at a partial vacuum (for example, 0.01 to 0.50 atm), contacting the droplets with a warm drying gas, or a combination of these measures. In some embodiments, spray drying comprises contacting the spray of droplets with a drying gas.

In some embodiments, removal of the solvent by spray drying results in solid dispersion compositions in the form of particles. The particles can have a mean diameter of about 100 µm or less, about 95 µm or less, about 90 µm or less, about 85 µm or less, about 80 µm or less, about 75 µm or less, about 70 µm or less, about 65 µm or less, about 60 µm or less, about 55 µm or less, about 50 µm or less, about 45 µm or less, about 40 µm or less, about 35 µm or less, about 30 µm or less, about 25 µm or less, or about 20 µm or less. In some embodiments, the particles have a mean diameter of about 50-100 µm, about 30-75 µm, about 25-50 µm, about 20-30 µm, about 10-25 µm, or about 15-20 µm. Particle size can be measured using particle size measuring techniques known to those of skill in the art. Non-limiting examples of particle size measuring techniques include sedimentation field flow fractionation, photon correlation spectroscopy, laser diffraction or disk centrifugation. Another useful characteristic diameter of the droplets produced by an atomizer is D90, the droplet diameter corresponding to the diameter of droplets that make up 90% of the total liquid volume. In some embodiments, the particles of the composition have diameters spanning about 10-20 µm at D90, 15-20 µm at D90, or 17-19 µm at D90.

In some embodiments, spray-drying results in compositions in which the compound of Formula I is amorphous. Methods and characterization of amorphousness are described herein.

Exemplary Methods of Administration and Treatment Methods

Compositions comprising a compound of Formula I-III can be used in the preparation of medicaments for the treatment of diseases or conditions in which steroid hormone nuclear receptor activity contributes to the pathology and/or symptoms of the disease. In addition, a method for treating any of the diseases or conditions described herein in a subject in need of such treatment, involves administration of pharmaceutical compositions containing at least one compound of Formula (1), or a pharmaceutically acceptable salt, pharmaceutically acceptable N-oxide, pharmaceutically active metabolite, pharmaceutically-acceptable prodrug, or pharmaceutically acceptable solvate thereof, in therapeutically-effective amounts to said subject.

The compositions containing the compound(s) described herein can be administered for prophylactic and/or therapeutic treatments. In therapeutic applications, the compositions are administered to a subject already suffering from a disease or condition, in an amount sufficient to cure or at least partially arrest the symptoms of the disease or condition, or to cure, heal, improve, or ameliorate the condition itself. Amounts effective for this use will depend on the severity and course of the disease or condition, previous therapy, the subject's health status, weight, and response to the drugs, and the judgment of the treating physician.

Once improvement of the subject's conditions has occurred, a maintenance dose is administered if necessary. Subsequently, the dosage or the frequency of administration, or both, can be reduced, as a function of the symptoms, to a level at which the improved disease or condition is retained. Subjects can, however, require intermittent treatment on a long-term basis upon any recurrence of symptoms.

In certain instances, it may be appropriate to administer therapeutically effective amounts of at least one of the compounds described herein (or a pharmaceutically acceptable salts, pharmaceutically-acceptable N-oxides, pharmaceutically active metabolites, pharmaceutically-acceptable prodrugs, and pharmaceutically acceptable solvates thereof) in combination with another therapeutic agent. By way of example only, if one of the side effects experienced by a subject upon receiving one of the compounds herein is inflammation, then it may be appropriate to administer an anti-inflammatory agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the subject is enhanced). Or, by way of example only, the benefit of experienced by a subject may be increased by administering one of the compounds described herein with another therapeutic agent (which also includes a therapeutic regimen) that also has therapeutic benefit. In any case, regardless of the disease or condition being treated, the overall benefit experienced by the subject may simply be additive of the two therapeutic agents or the subject may experience a synergistic benefit. Where the compounds described herein are administered in conjunction with other therapies, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is one of the compounds described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents. Multiple therapeutic combinations are envisioned.

In addition, compounds of Formula I-III may also be used in combination with procedures that may provide additional or synergistic benefit to the subject. By way of example only, subjects are expected to find therapeutic and/or prophylactic benefit in the methods described herein, wherein pharmaceutical composition of Formula (I) and/or combinations with other therapeutics are combined with genetic testing to determine whether that individual is a carrier of a mutant gene that is known to be correlated with certain diseases or conditions.

Compounds of Formula I-III and combination therapies can be administered before, during or after the occurrence of a disease or condition, and the timing of administering the composition containing a compound can vary. Thus, for example, the compounds can be used as a prophylactic and can be administered continuously to subjects with a propensity to conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. A compound is preferably administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the compound or a formulation containing the compound can be administered for at least 2 weeks, preferably about 1 month to about 3 years and in some embodiments from about 1 month to about 10 years. In other embodiments, the compound is administered once a day from 90 days to 2 years.

The pharmaceutical composition described herein may be in unit dosage forms suitable for single administration of precise dosages. In unit dosage form, the formulation is divided into unit doses containing appropriate quantities of one or more compounds. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for any of the compounds described herein are from about 0.03 to 60 mg/kg per body weight. An indicated daily dosage in a larger mammal, including, but not limited to, humans, is in the range from about 1 mg to about 4000 mg, conveniently administered in one or more doses, including, but not limited to, up to five times a day or in retard form. Suitable unit dosage forms for oral administration comprise from about 1 mg to about 4000 mg active ingredient. In some embodiments, a single dose of compounds of Formula (1) is within the range of about 50 mg to about 3500 mg. In some embodiments, a single dose of compounds of Formula (1) is about 90 mg, about 200 mg, about 250 mg, about 325 mg, about 500 mg, about 650 mg, about 975 mg, about 1300 mg, about 1625 mg, about 1950 mg, about 2600 mg or about 3250 mg. In some embodiments, an administration of compounds of Formula (1) of about 90 mg, about 325 mg, about 500 mg, about 650 mg, about 975 mg, about 1300 mg, about 1625 mg, about 1950 mg, about 2600 mg or about 3250 mg is given as multiple doses.

In some embodiments, the single dose of compounds of Formula (a) is between 90 to 3500 mgs and the compound is administered to a subject for between 90 days to two years.

Such dosages may be altered depending on a number of variables, not limited to the activity of the compound used, the disease or condition to be treated, the mode of administration, the requirements of the individual subject, the severity of the disease or condition being treated, and the judgment of the practitioner.

Exemplary Methods of Providing Therapy

The present invention provides therapeutic strategies for the treatment of cancer or other disease in subjects. In some embodiments, the disease is polycystic ovarian disease. In some embodiments, the cancer in prostate cancer. In other embodiments, the cancer is breast cancer. In yet other embodiments, the cancer is ovarian cancer. In some embodiments, the subject is human. In other embodiments, the subject is not a human.

In particular embodiments, the present invention provides preparations and regimens for the use of a compound of Formula I or formula II in the treatment of prostate cancer. In some embodiments, the prostate cancer is castration resistance prostate cancer. In some embodiments, the prostate cancer is chemotherapy naïve prostate cancer.

In some embodiments, the present invention provides therapeutic regimens that involve oral administration of a compound of Formula I or formula II.

In some embodiments, the present invention provides therapeutic regimens that involve administration of multiple doses of a compound of Formula I or formula II. In some embodiments, different doses are spaced apart in time. In some embodiments, all doses contain the same amount of a compound of Formula I or formula II. In some embodiments, different doses contain different amounts of a compound of Formula I or formula II. In some embodiments, different doses that are separated in time are separated from one another by the same amount of time; in some embodiments, different doses that are separated in time are separated from one another by different amounts of time. In some embodiments, the present invention provides dosing regimens that include administration of a plurality of doses separated by a regular time interval (or intervals), followed by a rest period, optionally followed by a second plurality of doses separated by a regular time interval (or intervals).

In some embodiments, at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168 or more doses of a compound of Formula I or formula II are administered. In some embodiments, at least 7, 14, 21, 28, 35, 42, 49, 56, 63, 70, 77, 84, 91, 98, 105, 112, 119, 126, 133, 140, 147, 154, 161, 168, or more doses of a compound of Formula I or formula II are administered.

EXAMPLES

Galeterone is a novel drug that exhibits three mechanisms of action to inhibit AR activity, via inhibition of de novo androgen synthesis, blocking the ligand binding domain to prevent androgen binding, and inducing AR degradation. Thus, in this study we evaluated the relationship between the mechanism of action of this drug and the utility of various biomarkers, including the status of androgen receptor in the tumor being treated.

Example 1

Galeterone Downregulates Both Wild-Type and Mutant AR

Figure 2:
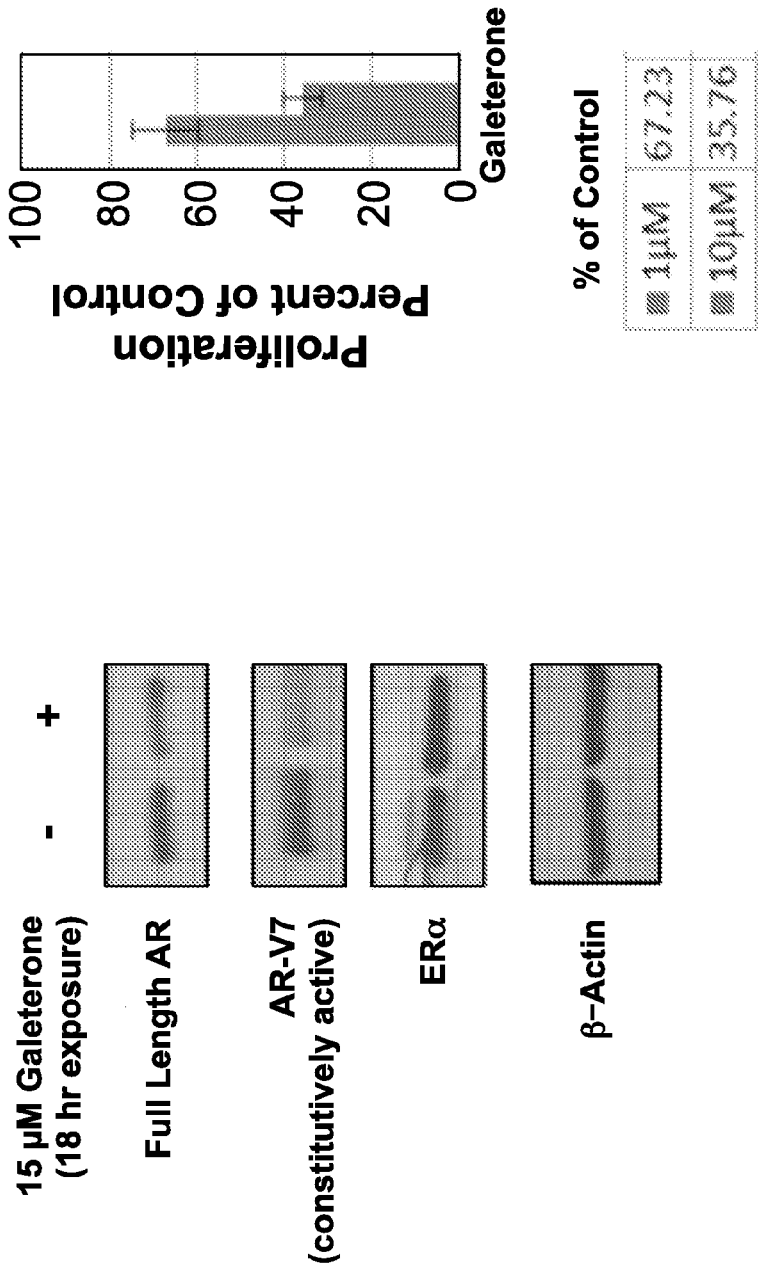
FIG. 2 shows that galeterone downregulates full-length and splice variant AR and reduces cell proliferation in a CWR22rv1 cell line.
Figure 3:
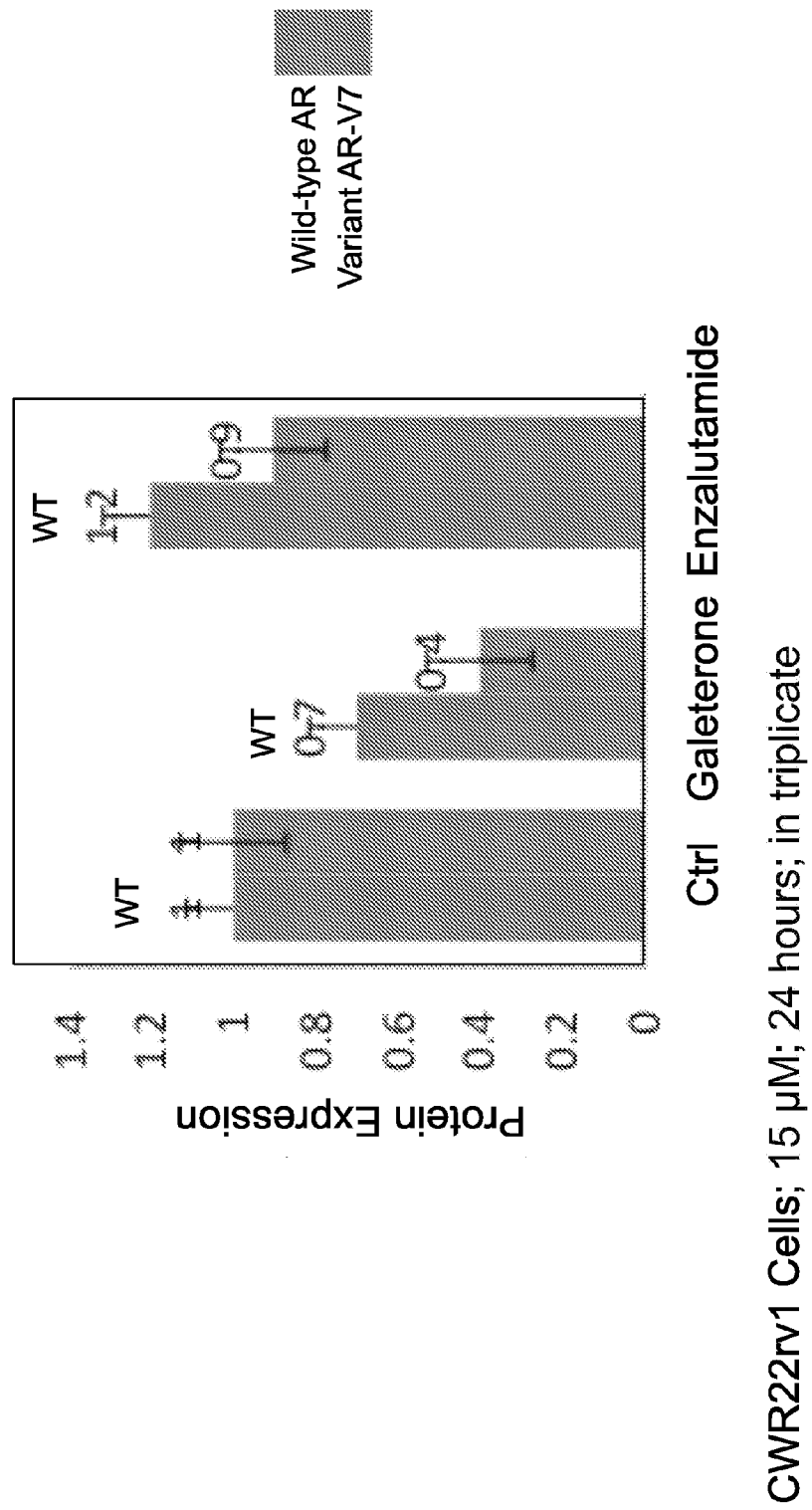
FIG. 3 shows that galeterone overcomes abiraterone and enzalutamide resistance due to AR splice variants. Galeterone, but not enzalutamide, reduces full-length and splice variant AR-V7 protein.
Figure 4:
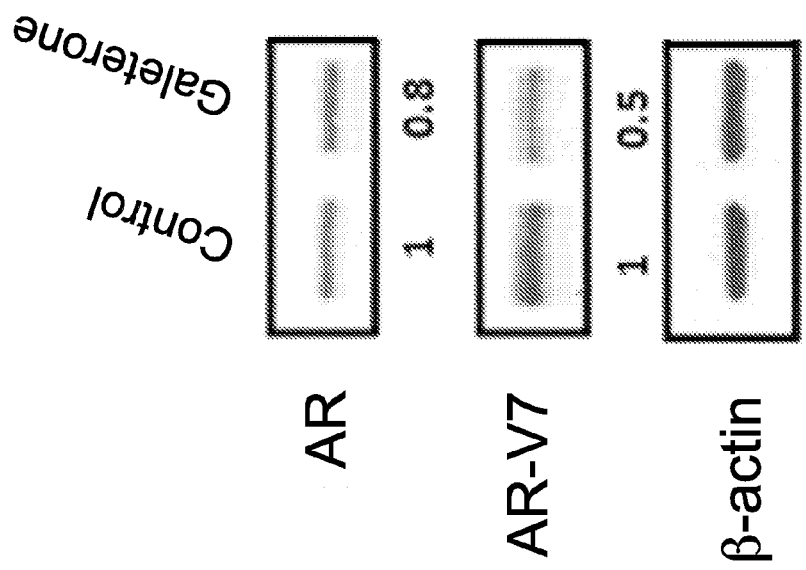
FIG. 4 shows that galeterone reduces both full-length and AR-V7 proteins in a CWR22rv1 cell line.
Figure 5:
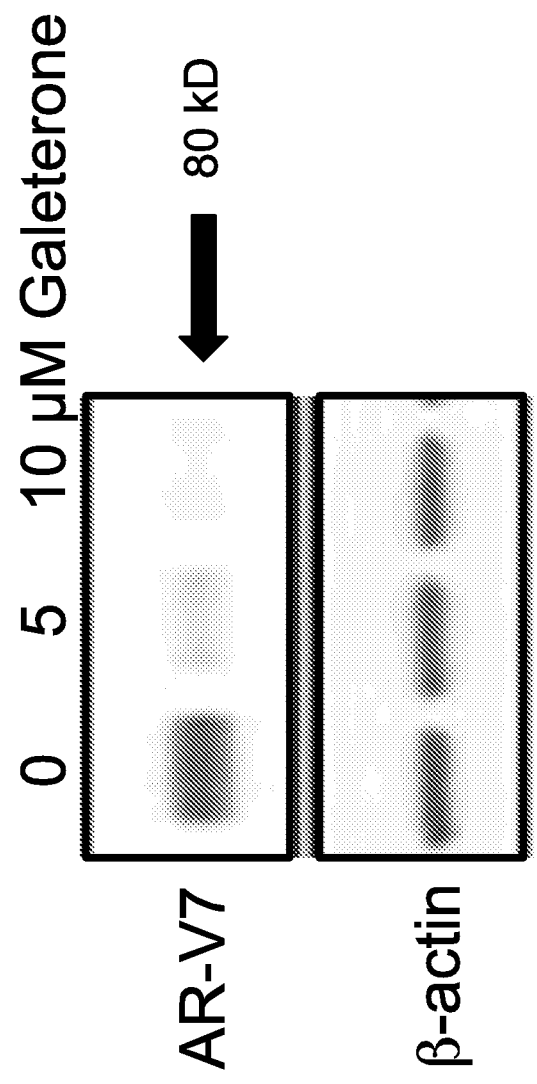
FIG. 5 shows that galeterone reduces AR-V7 in DU145 cells transfected with AR-V7 splice variant.
Figure 6:
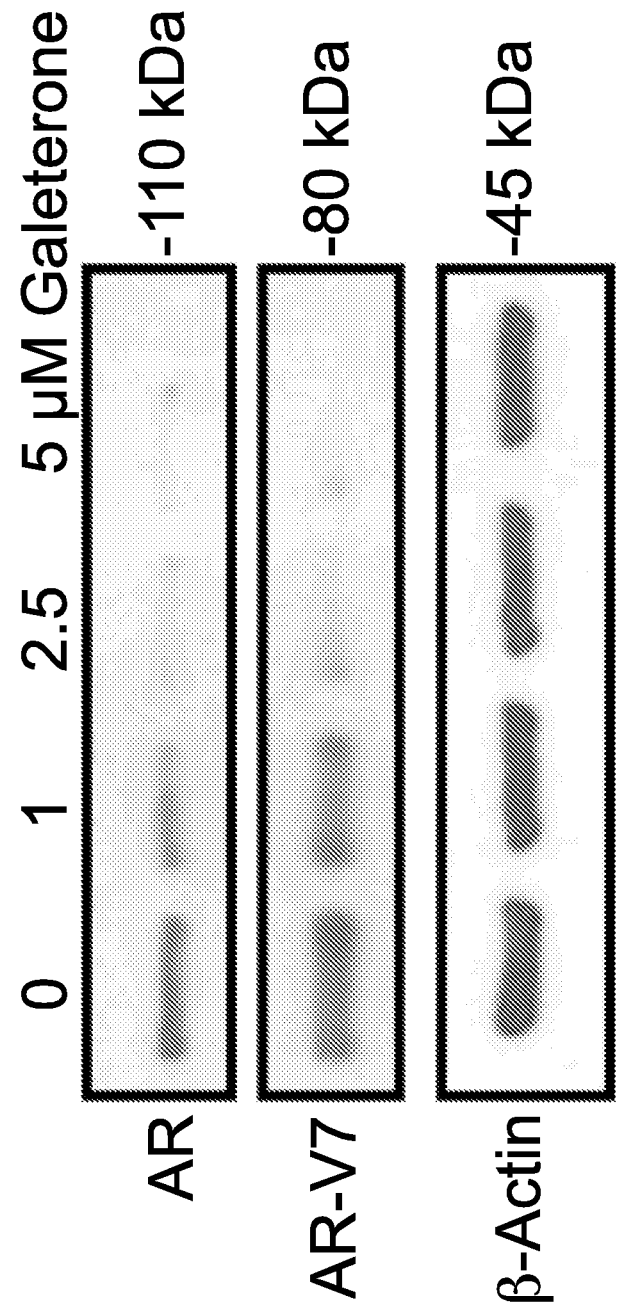
FIG. 6 shows that galeterone reduces full-length and splice variant AR-V7 with 72 hour exposure.

An experiment to detect expression of full-length AR and AR-V7 variant proteins was conducted in a CWR22rv1 cell line which constitutively expresses both AR and AR-V7. As shown in, FIG. 2, galeterone downregulates full-length and splice variant AR and reduces cell proliferation in this cell line. See also FIG. 4. Further, galeterone successfully overcomes abiraterone and enzalutamide resistance due to AR splice variants (FIG. 3). Galeterone, but not enzalutamide, reduces full-length and splice variant AR-V7 protein. Further, galeterone reduces AR-V7 in DU145 cells transfected with AR-V7 splice variant (FIG. 5). Similarly, lower levels of galeterone reduce full-length and splice variant AR-V7 with 72 hour exposure (FIG. 6).

Example 2

Galeterone is Effective in a Model of Enzalutamide Resistance

Figure 7:
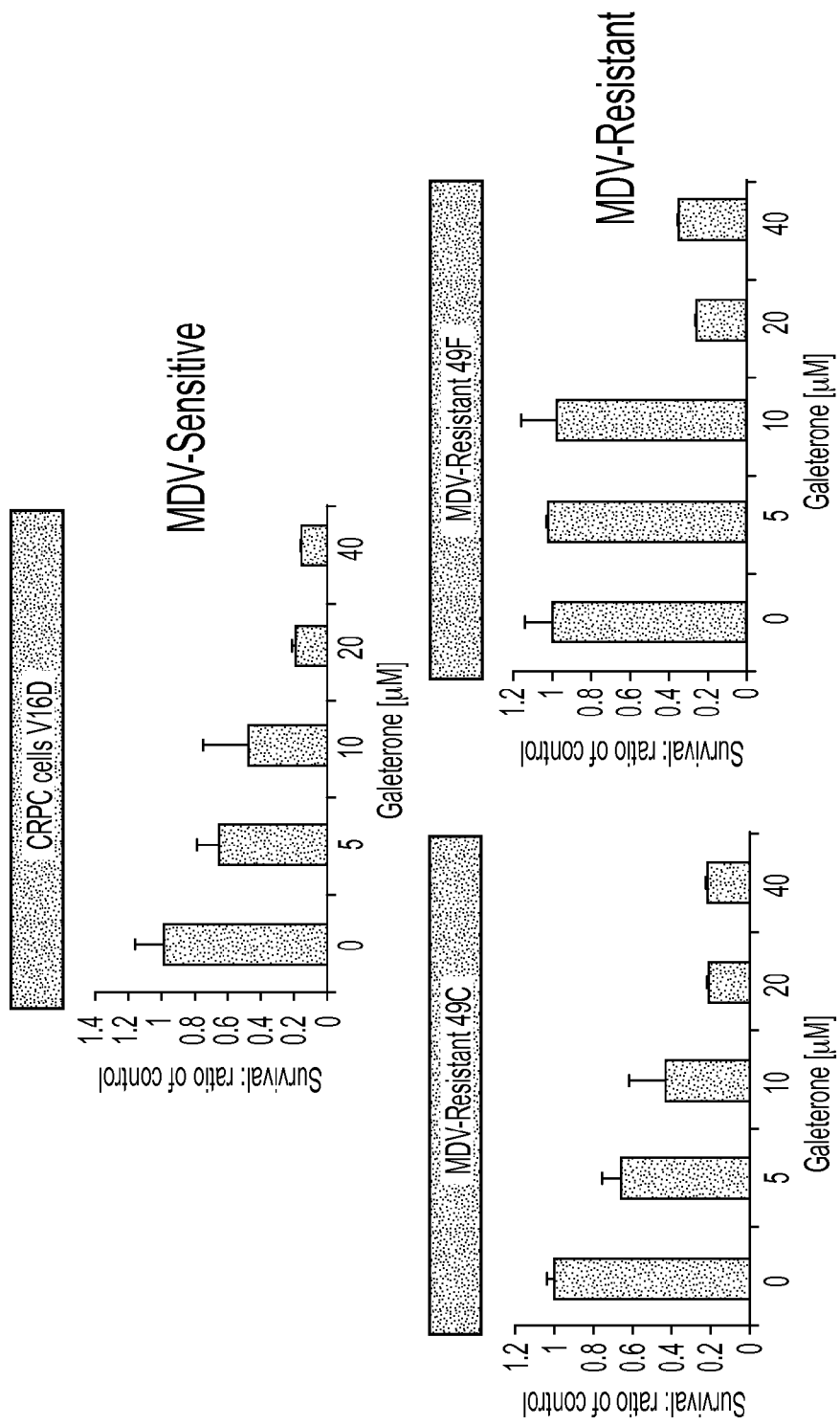
FIG. 7 depicts proliferation of castration resistant and enzalutamide resistant cell lines.
Figure 8:
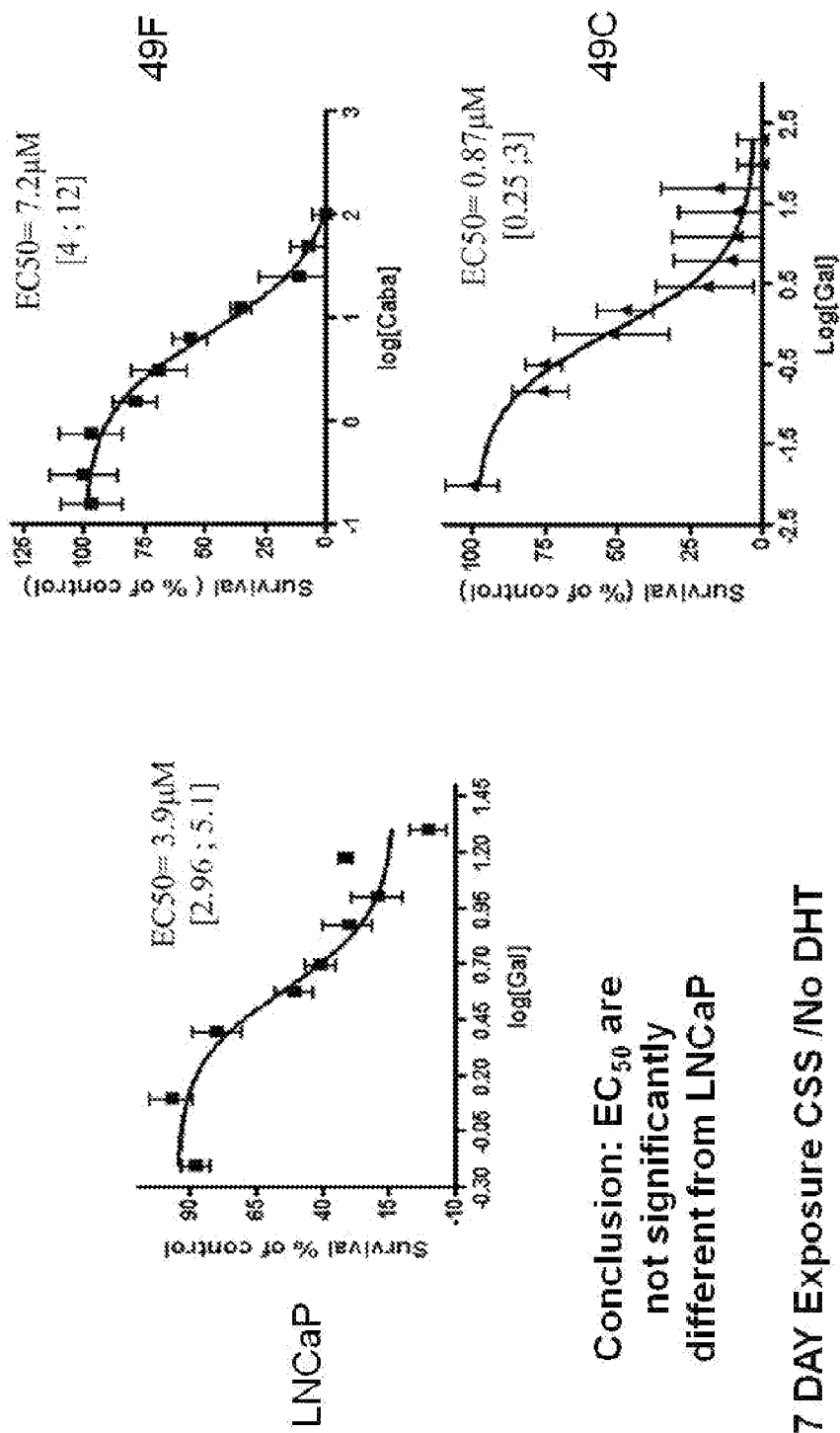
FIG. 8 depicts response of castration resistant and enzalutamide resistant cell lines to galeterone.
Figure 9A:
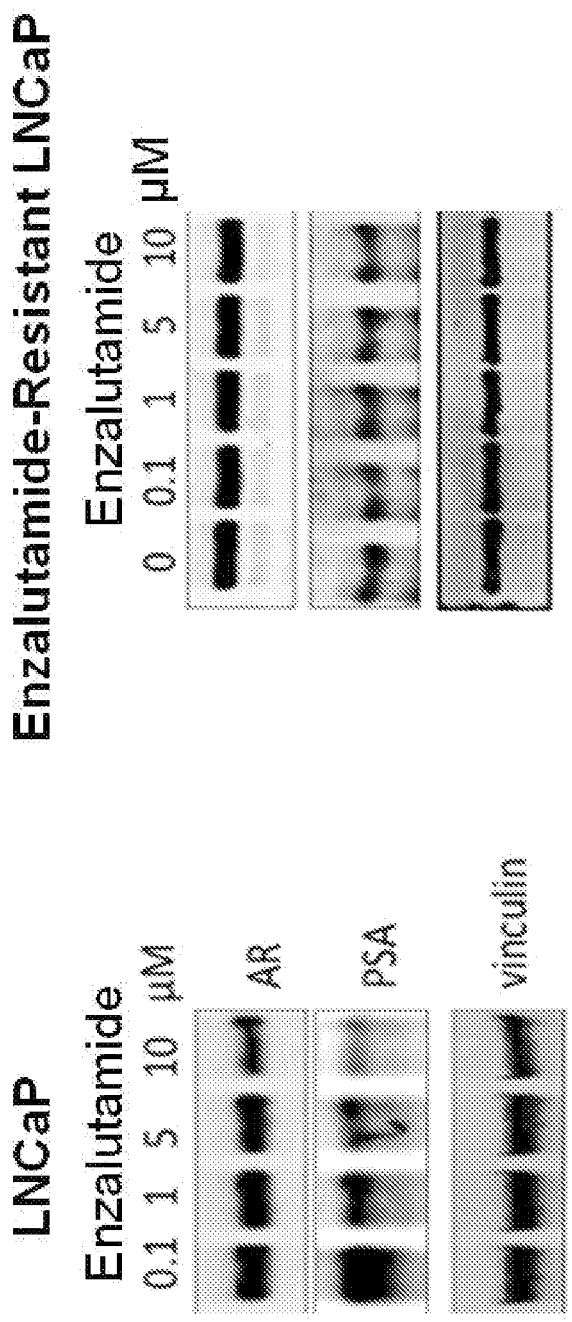
FIG. 9A depicts an Androgen Receptor (AR) and Prostate Specific Antigen (PSA) western blot of LNCaP and enzalutamide resistant LNCaP cells.
Figure 9B:
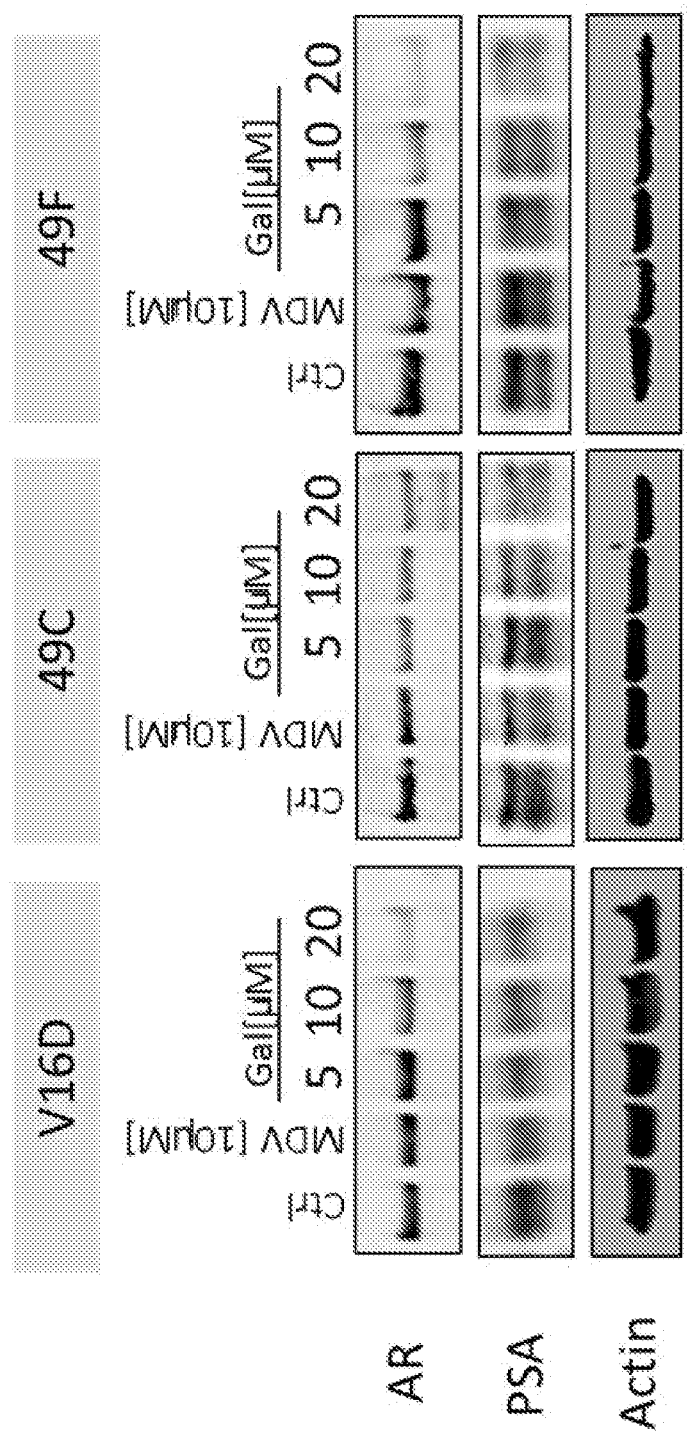
FIG. 9B depicts the effect of galeterone on AR and PSA protein levels in enzalutamide responsive and enzalutamide resistant LNCaP cells.
Figure 10:
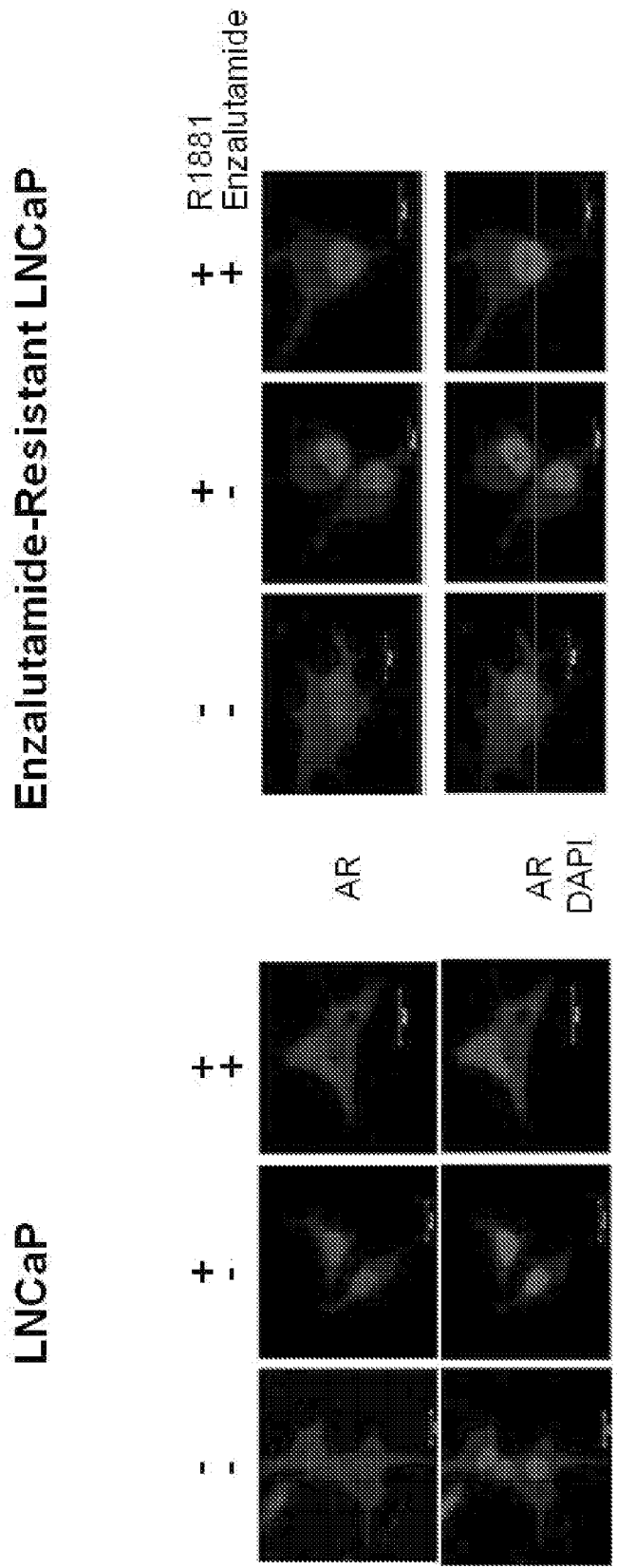
FIG. 10 depicts androgen receptor localization in cells treated with a synthetic androgen in the presence or absence of enzalutamide.
Figure 11:
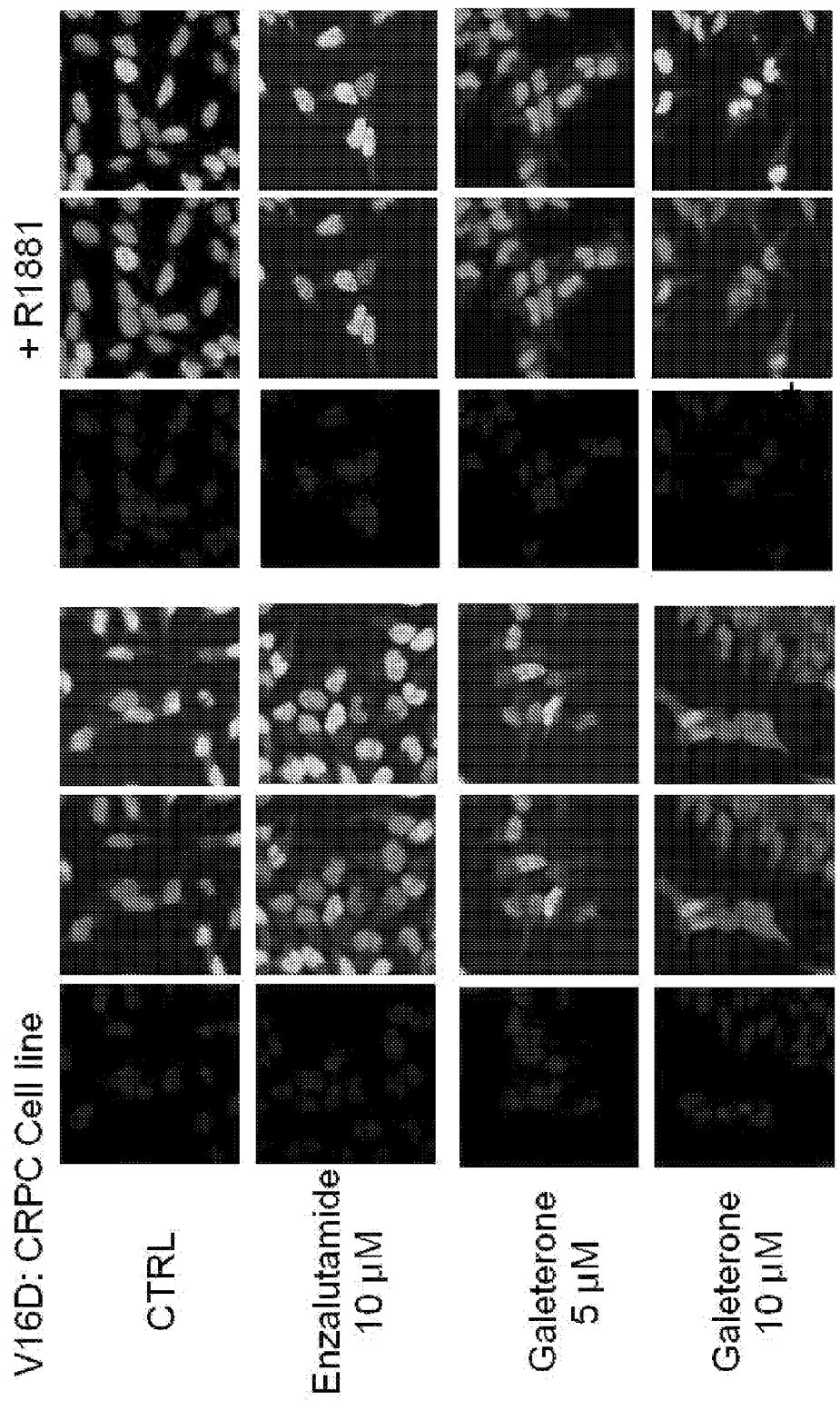
FIG. 11 depicts androgen receptor localization in a CPRC cell line treated with a synthetic androgen in the presence or absence of enzalutamide or galeterone.
Figure 12:
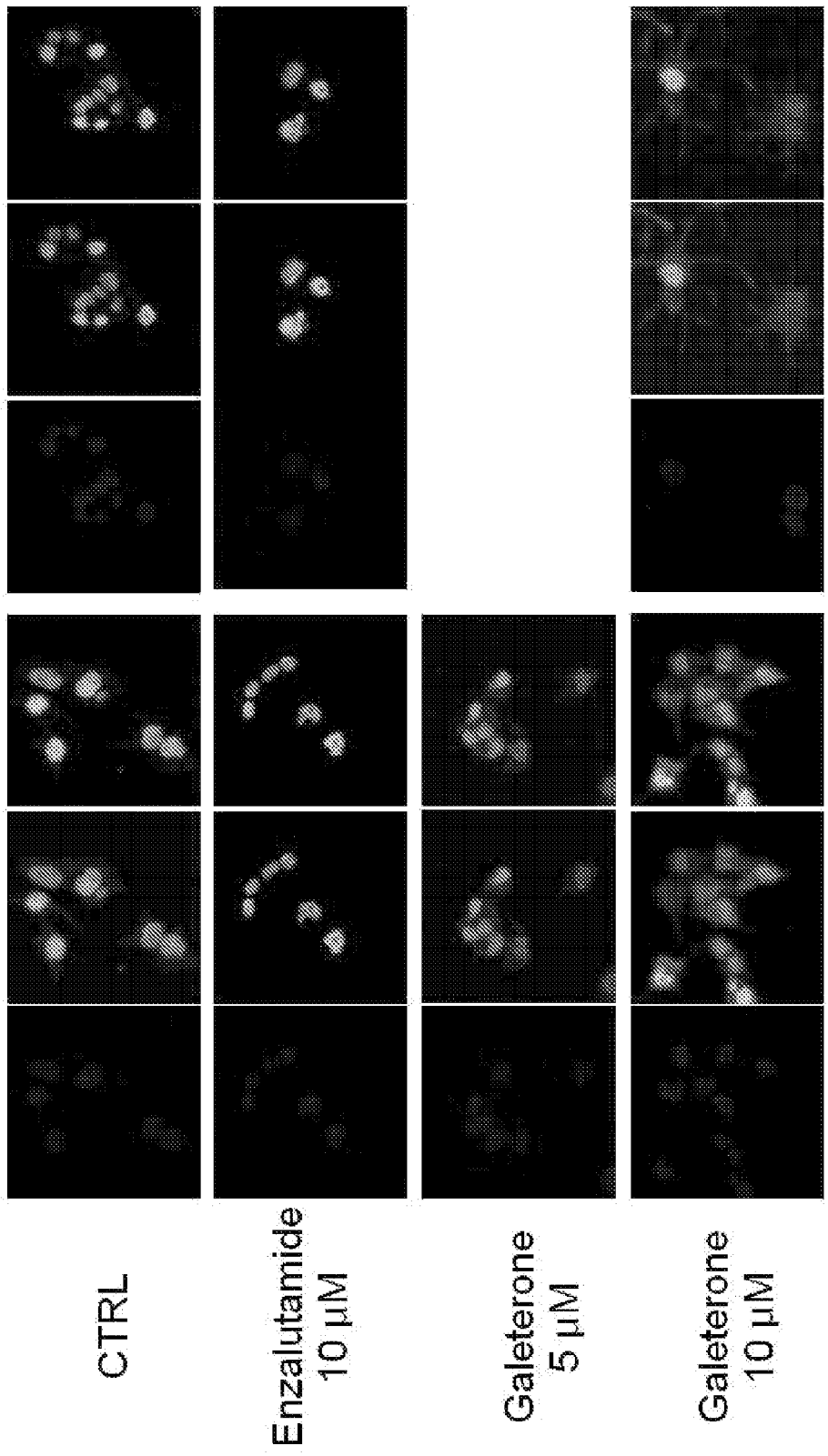
FIG. 12 depicts androgen receptor localization in an enzalutamide resistant cell line treated with a synthetic androgen in the presence or absence of enzalutamide or galeterone.
Figure 13:
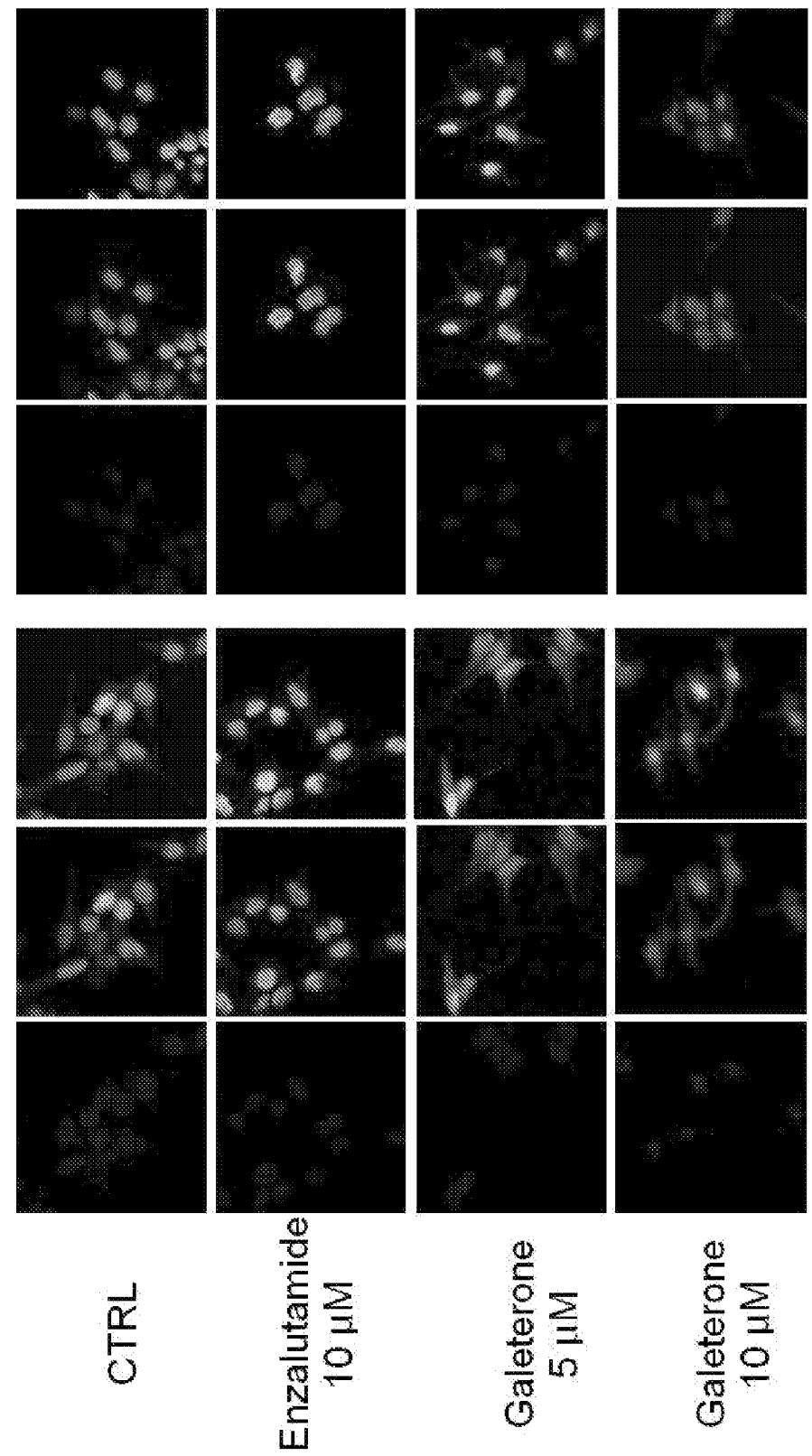
FIG. 13 depicts androgen receptor localization in an enzalutamide resistant cell line treated with a synthetic androgen in the presence or absence of enzalutamide or galeterone.
Figure 14:
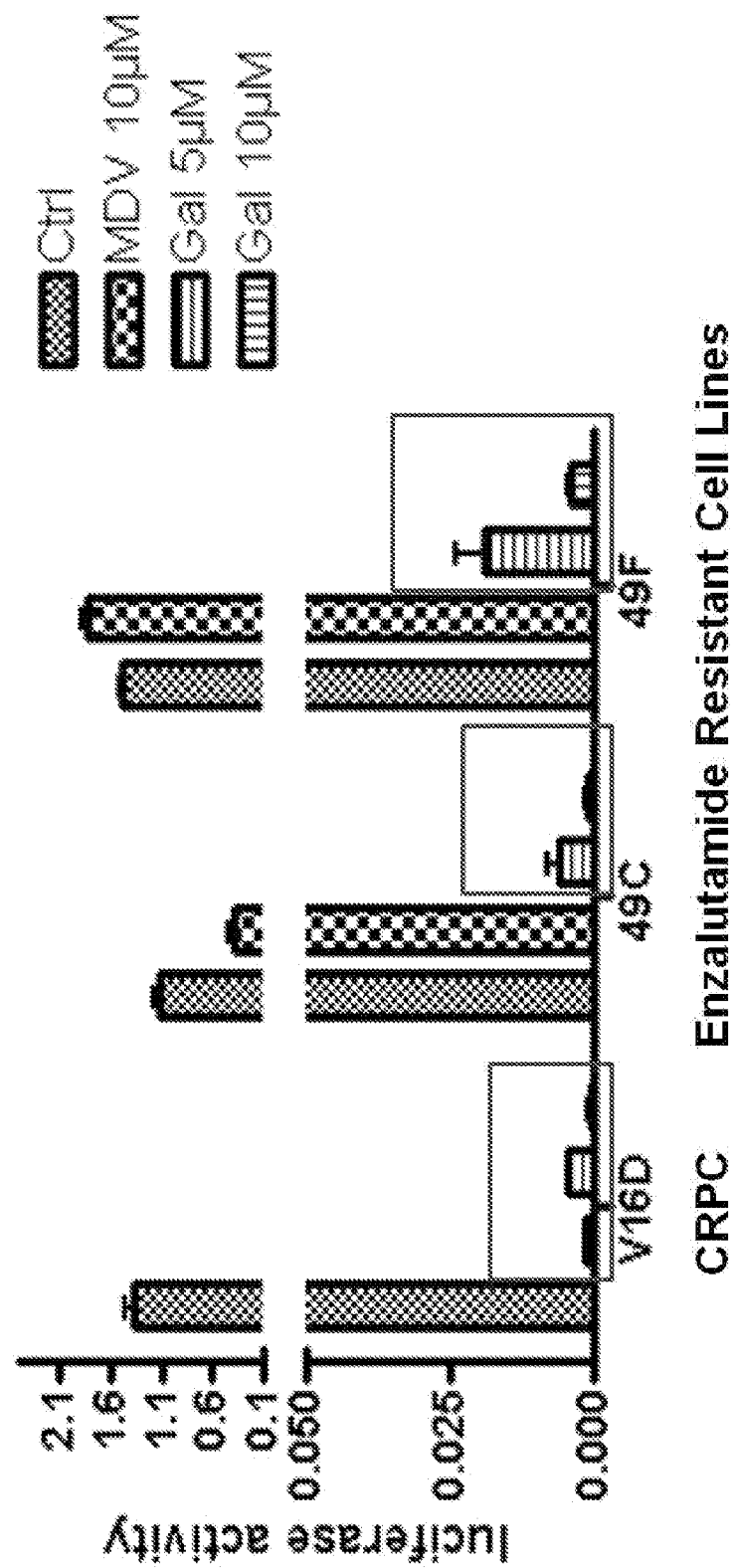
FIG. 14 depicts AR luciferase reporter activity in cell lines treated with enzalutamide or galeterone.
Figure 15A:
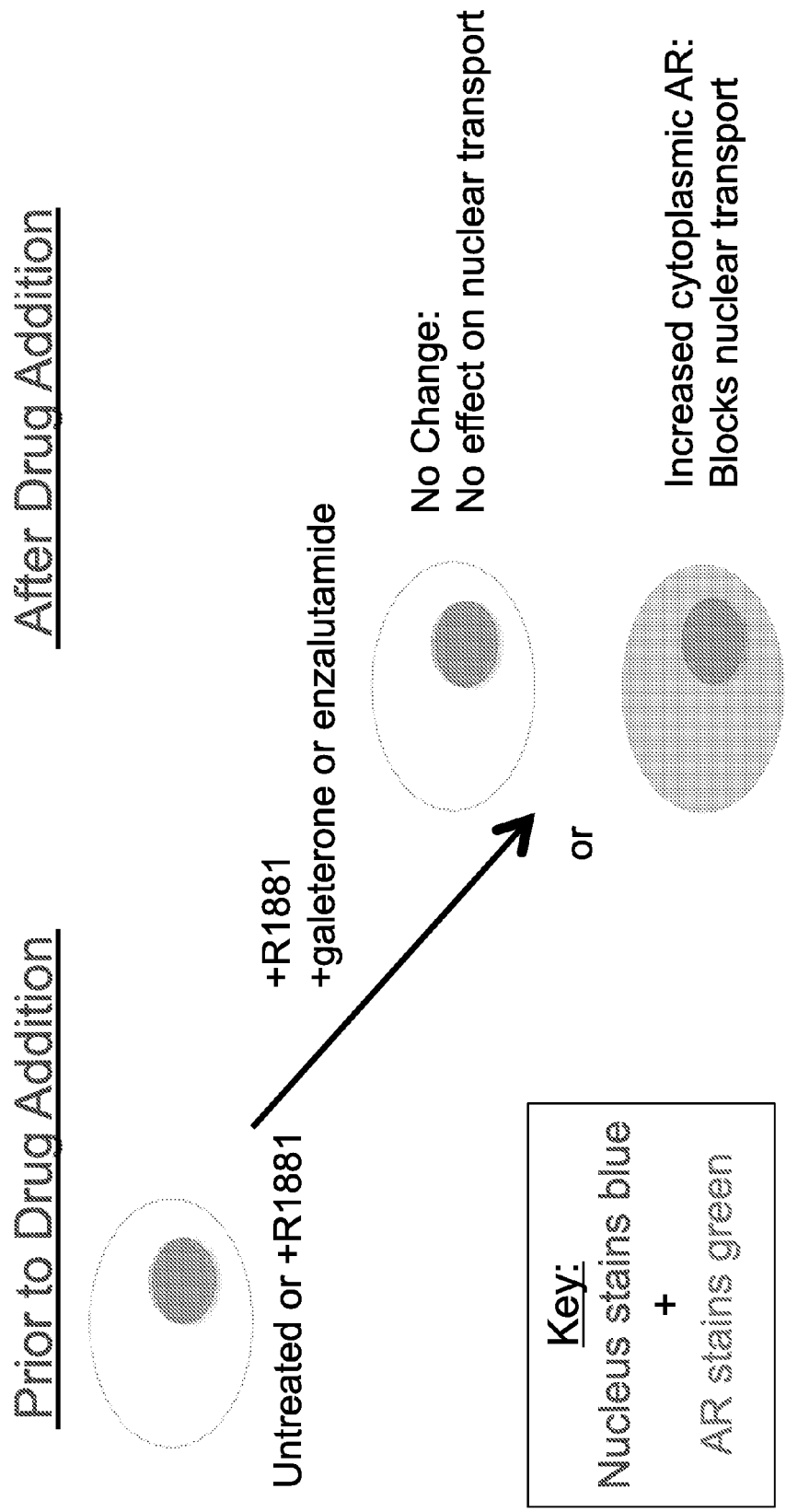
FIG. 15A shows the design of an immunofluorescence experiment to visualize nuclear localization of test compounds used.

As a pre-clinical model of Enzalutamide resistance, drug resistant and CRPC cell lines were derived from three generations of serially passaged Enzalutamide resistant, or vehicle control treated, LNCaP xenografts. Resistant cells ("49C" and "49F") were maintained in vitro under constant exposure to 10 µM of Enzalutamide and were used to study the anti-cancer and AR targeting effects of Galeterone in the Enzalutamide resistant setting. Both 49F and 49C cell lines were found to have low expression of AR-V7. Using crystal violet and MTT assays, we found that Galeterone had anti-proliferative effects in LNCaP cells, in CRPC cells, and most importantly, in those resistant to Enzalutamide (FIG. 7). Dose-response studies of Galeterone in LNCaP cells and Enzalutamide resistant cell lines demonstrated similar EC50 for Galeterone in reducing cell viability in Enzalutamide resistant cell lines 49F and 49C, as compared to the EC50 for Galeterone in Enzalutamide responsive LNCaP cells (FIG. 8). Enzalutamide treatment reduced AR and PSA protein expression levels in LNCaP cells but not in the Enzalutamide resistant cell line (FIG. 9A). Compared to Enzalutamide treatment, Galeterone induced a greater reduction in AR and prostate-specific antigen (PSA) protein expression (FIG. 9B). Strikingly, the effects of Galeterone were still observed in resistant cells (FIG. 9B), which show no decrease in AR protein expression or PSA protein expression (FIG. 9A). To determine the effects of Enzalutamide and Galeterone on AR nuclear translocation, LNCaP and Enzalutamide resistant cell lines were treated with the synthetic androgen R1881 and/or Enzalutamide. AR localization was visualized by immunocytochemistry. R1881 alone caused robust AR translocation to the nucleus in both LNCaP and Enzalutamide resistant cell lines (FIGS. 10-13) Co-treatment with R1881 and enzalutamide reduced AR nuclear translocation as compared to R1881 treatment alone in LNCaP cells but not Enzalutamide resistant cells (FIGS. 10-13). To determine the effects of enzalutamide and Galeterone on AR activity, an AR luciferase assay was performed in the enzalutamide-responsive CPRC cell line and the Enzalutamide resistant cell lines 49C and 49F. All cell lines, untreated, exhibited high AR activity levels (FIG. 14). Enzalutamide treatment reduced AR activity in the enzalutamide-responsive cell line but not in the resistant cell lines 49C or 49F (FIG. 14). Galeterone, by contrast, reduced AR activity in all three cell lines (FIG. 14). FIG. 15A shows the design of an immunofluorescence experiment to visualize nuclear localization of test compounds used, and FIG. 15B shows that galeterone, but not enzalutamide, reduces AR nuclear translocation (as seen by increased green cytoplasmic staining vs. control or enzalutamide and less nuclear green staining). Together, the data show that Galeterone strongly inhibits AR activity and suppresses castration-resistant LNCaP growth as well as enzalutamide-resistant cell growth in vitro.

Example 3

Figure 16:
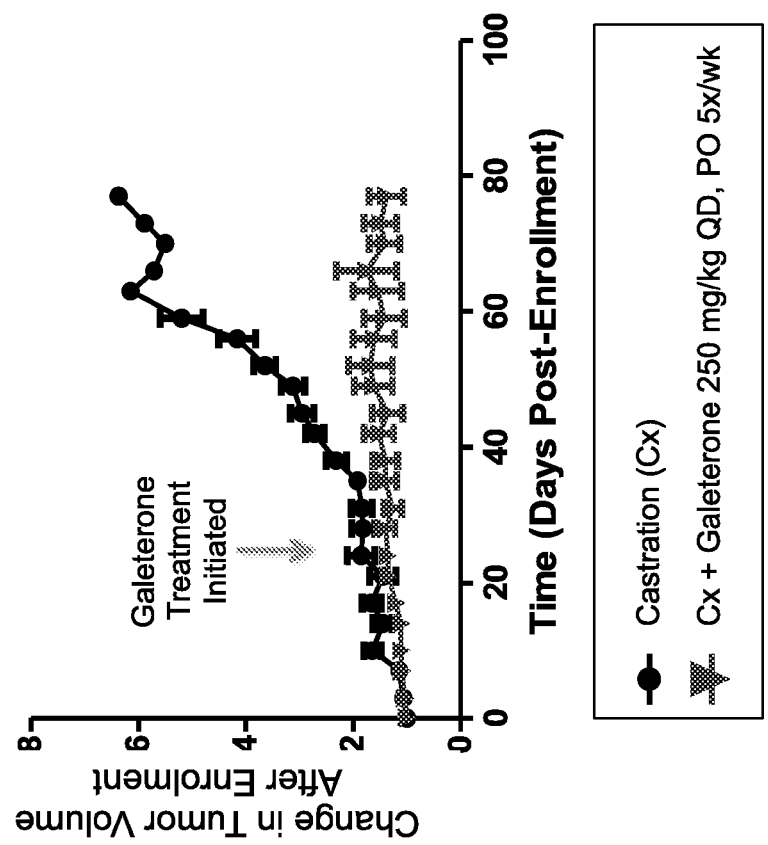
FIG. 16 shows that castration resistant tumors which express AR-V7 respond to galeterone. AR-V7 was detected in LuCaP136 castration resistant xenograft tumors using RT-PCR.

Galterone Activity in Castration Resistant Xenograft Tumors which Express Mutated Androgen Receptor Galeterone was tested in a xenograft model of CRPC in mice. FIG. 16 shows that castration resistant tumors which express AR-V7 respond to galeterone. AR-V7 was detected in LuCaP136 castration resistant xenograft tumors using RT-PCR.

Example 4

Galeterone Downregulates Mutant Androgen Receptors

Figure 17:
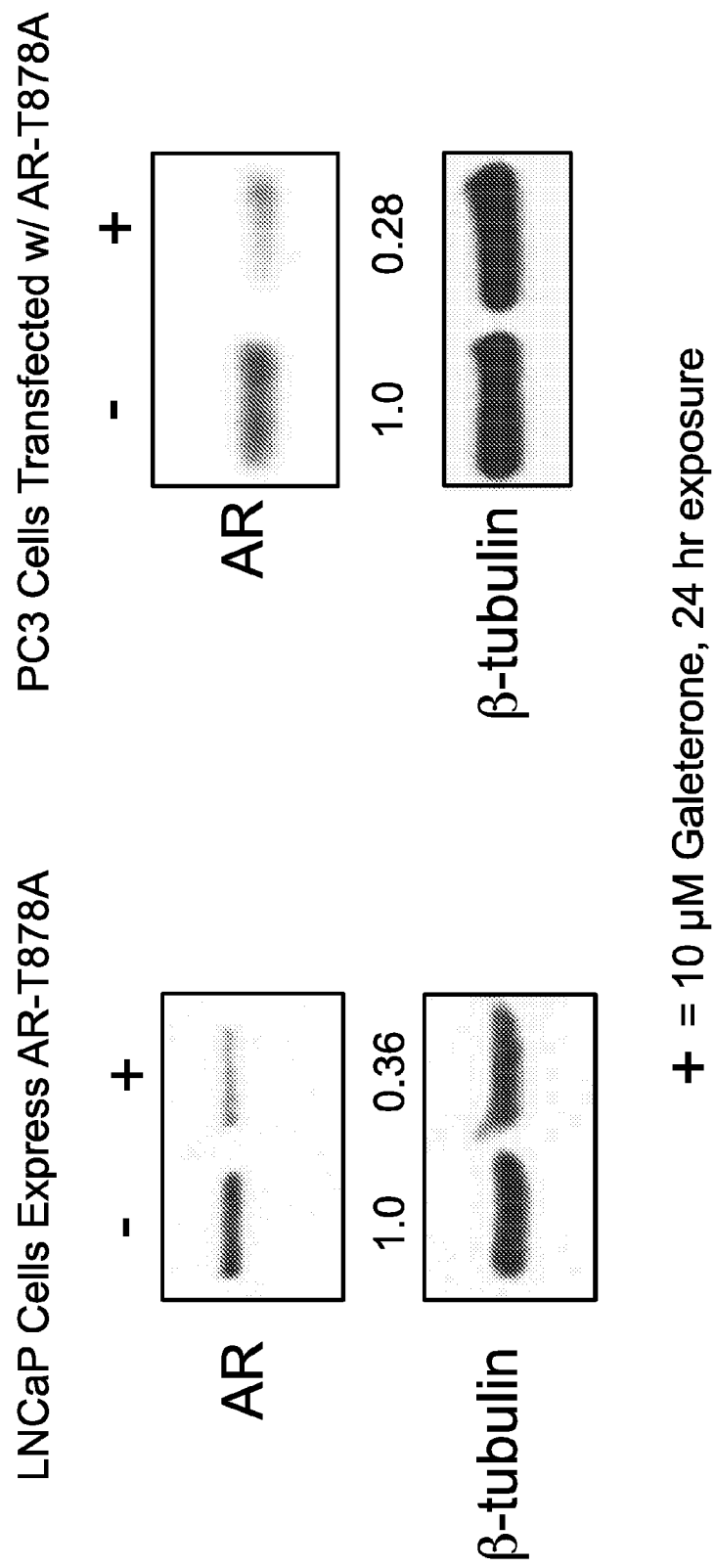
FIG. 17 shows that galeterone downregulates androgen receptors carrying the AR-T878A mutation.
Figure 19:
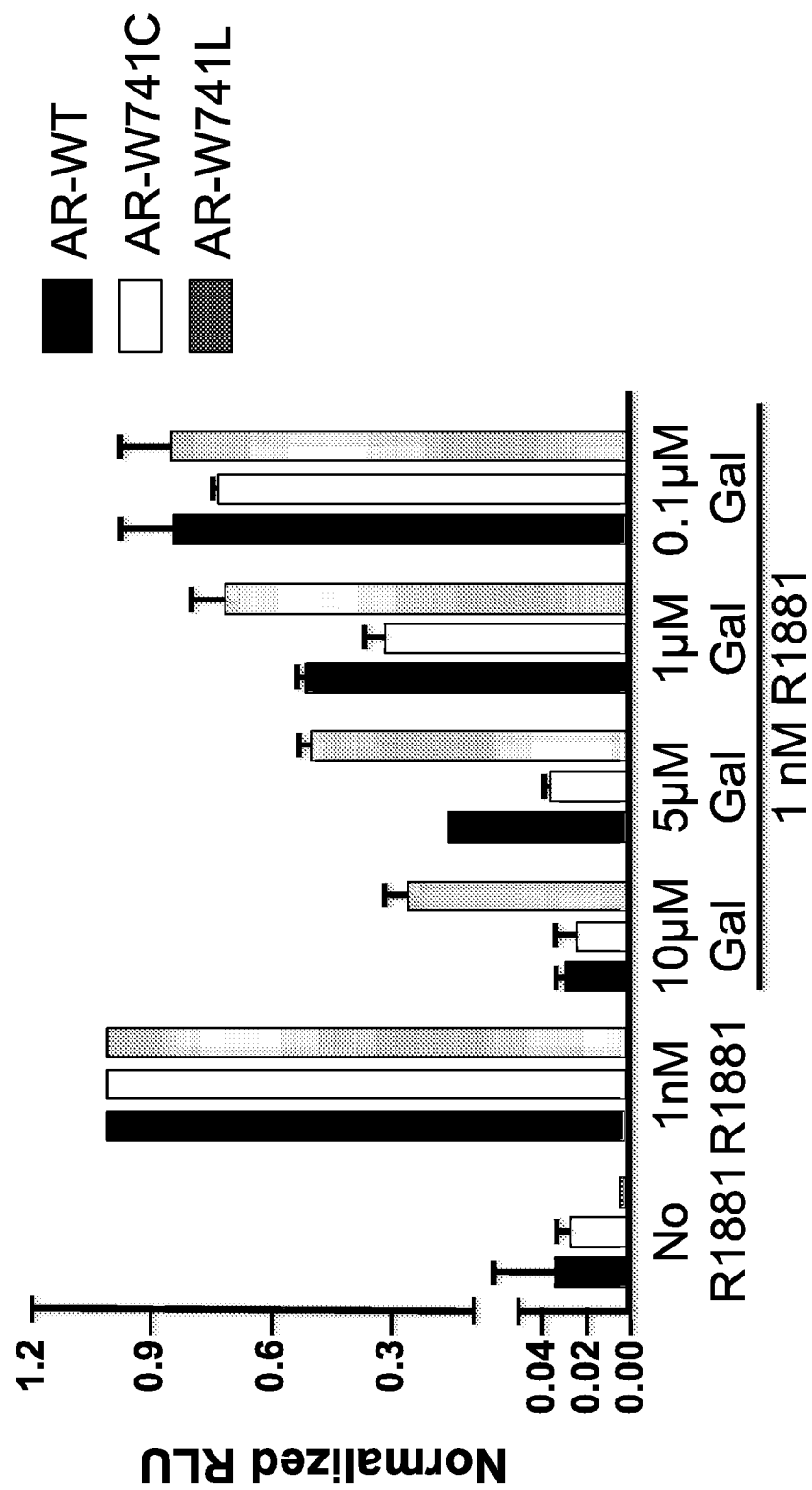
FIG. 19 shows that galeterone reduces AR-dependent gene expression in cells with wild-type AR and cells with AR point mutations. These cells also express AR receptors with F876L mutation.
Figure 20:
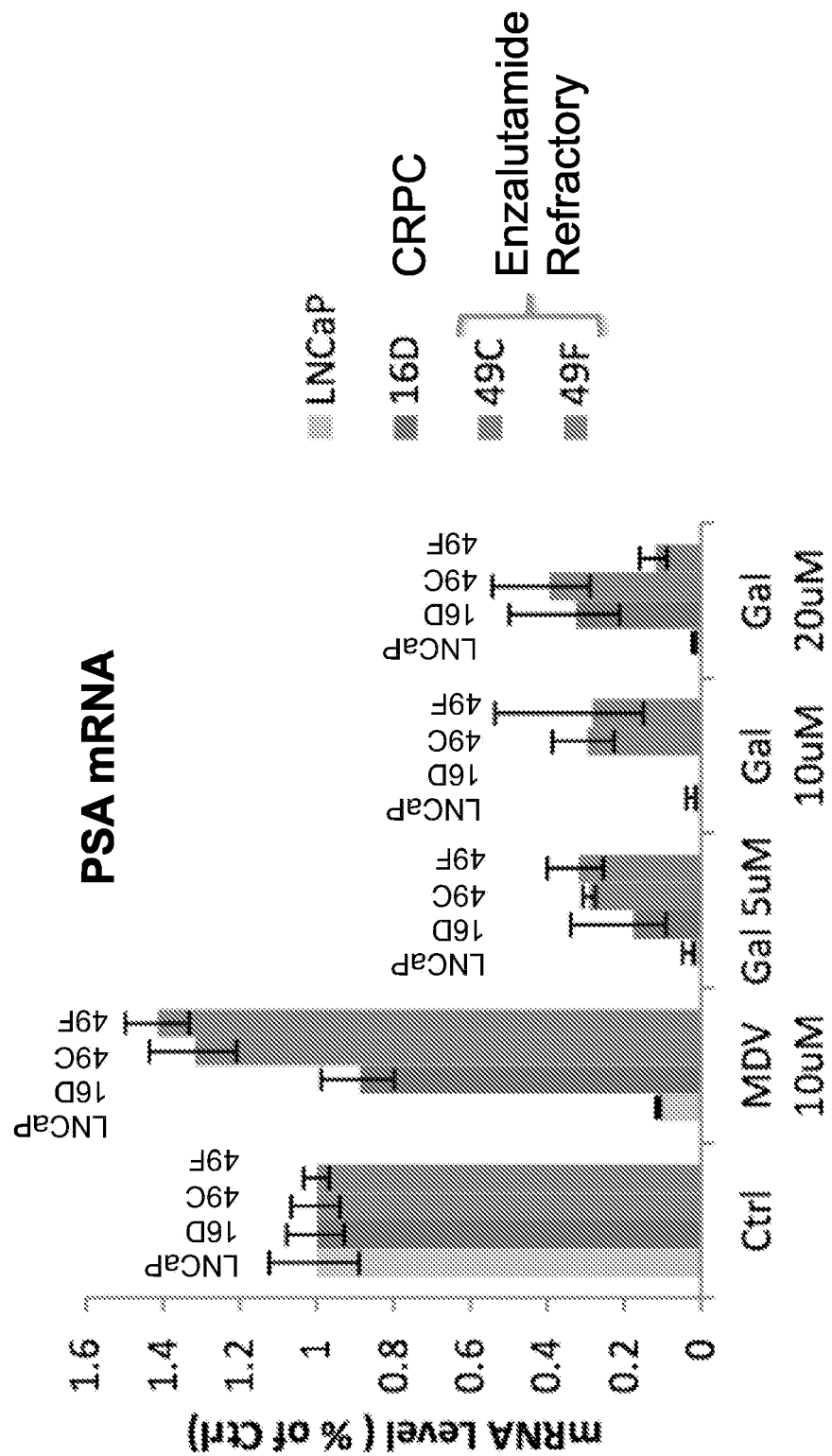
FIG. 20 shows decrease in PSA induced by PSA in CRPC and enzalutamide resistant cell lines.
Figure 21:
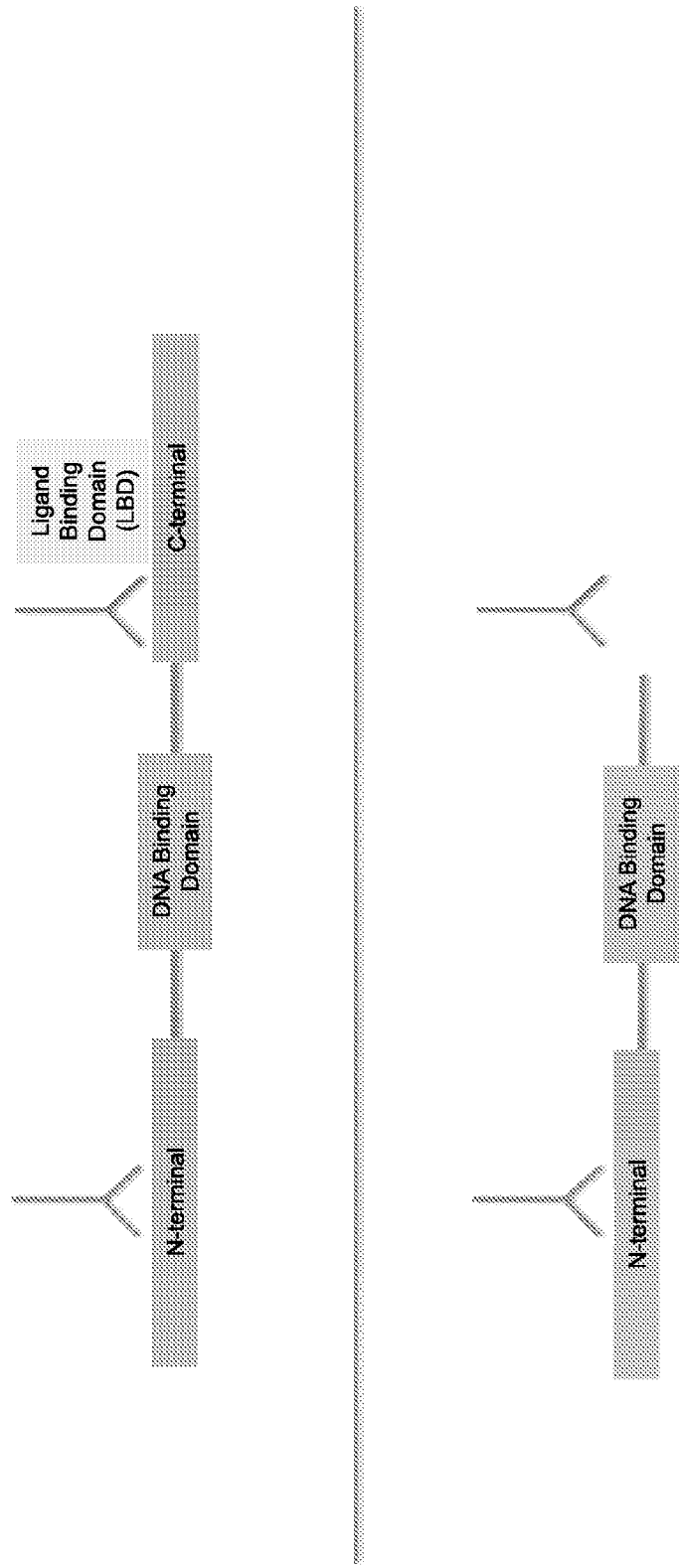
FIG. 21 depicts a scheme illustrating the detection of AR variants in which the C-terminal domain has been lost.

AR point mutation AR-T878A is commonly present in hormone refractory tumors and because the mutation is in the androgen binding site the mutant AR binds to steroids and drugs very differently. In particular, the AR-T878A mutant binds to progesterone which is elevated in abiraterone-treatment thus tumors expressing this mutation are resistant to abiraterone. An experiment was conducted to FIG. 17 shows that galeterone downregulates androgen receptors carrying the AR-T878A mutation. This effect is seen on either LNCaP cells or AR negative PC3 cells that have been transfected with AR-T878A.

Example 5

Figure 22:
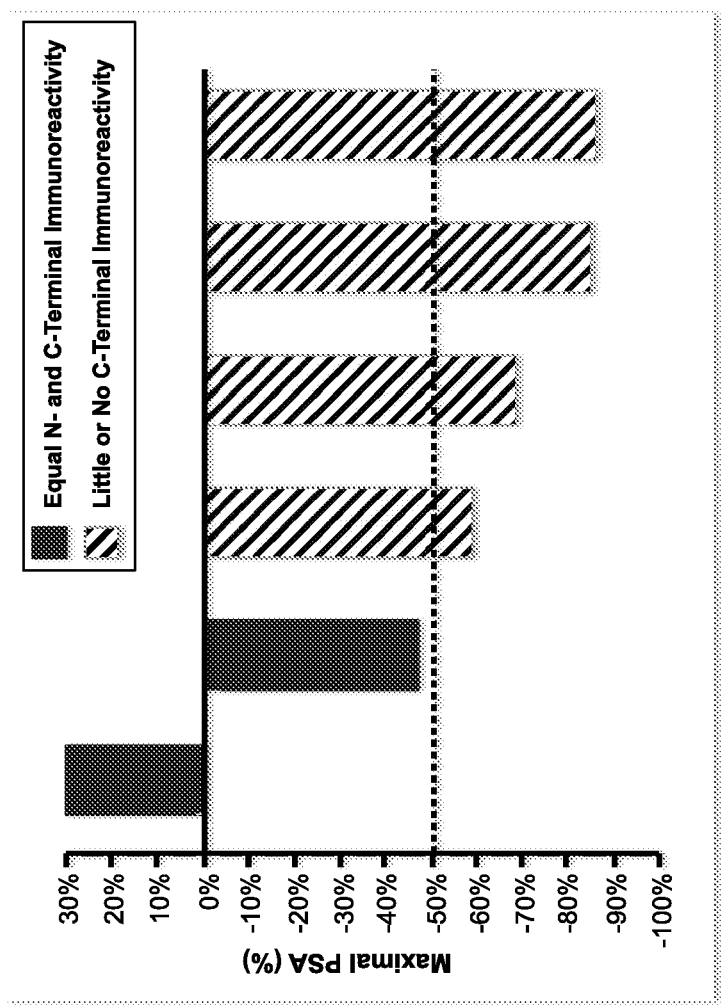
FIG. 22 shows the results of a study in which patients with C-terminal AR loss (4/4) treated with galeterone show maximal PSA response (>50%).

CRPC Patients Having Androgen Receptor Splice Variants Respond to Galeterone Therapy Galeterone was administered to a group of patients for 12 weeks at 2550 mg daily. A group of six patients naive to previous CRPC therapy was analyzed with respect to AR status. Four of the six patients were identified as having AR receptors with a C-terminal loss as determined by the evaluation of C-terminal androgen receptor expression in relation to N-terminal androgen receptor expression. The results of the experiments are shown in FIG. 22. All four of the patients having this AR variant had maximal reductions in PSA levels of at least 50%. The other two patients, which did not have AR receptors with a loss of the C-terminal domain, did not respond as strongly to galeterone as evidenced by the lesser reduction in PSA.

Therefore, galeterone is a potent inhibitor of the AR pathway and may represent the next generation of hormone therapy for patients with not only CRPC but also Enzalutamide resistant disease. Furthermore, as galeterone is a potent inhibitor of the AR pathway, it may represent an alternative to abiraterone or to patients who are resistant to abiraterone therapy. While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 6

Detection of Mutated AR by Amplification

Mutated AR in patient samples may be detected by PCR. Quantitative real-time PCR methods are known in the literature, specifically as described in Luo et al., US2011/0110926. As described Cancer Research 2009, 69:16-22, for RT-PCR analyses, total RNA was isolated and reverse transcribed to form cDNA and was used in a RT-PCR analysis. PCR primers were designed as described to specifically amplify transcript sequences that are known in the NH2 terminal (5' primers) (for example primer P6/P7/P9) and within the mutated forms (truncated, for example P7) of the AR protein (i.e. specific to AR-V7) mRNA and can be readily detected within about 30 (specifically 28) PCR amplification cycles. Using methods as described it would be possible to detect expression levels of truncated AR in samples from patients with prostate cancer. In this analysis, and due to variable expression levels in patient samples, the gene SF3A3, was used as a reference gene for normalization.

The invention claimed is:

1. A method comprising a step of:
administering therapy to a human subject having prostate cancer and expressing an androgen receptor variant that lacks the ligand binding domain,
wherein the androgen receptor variant that lacks the ligand binding domain is AR-V7, which therapy comprises administering a compound of formula I:

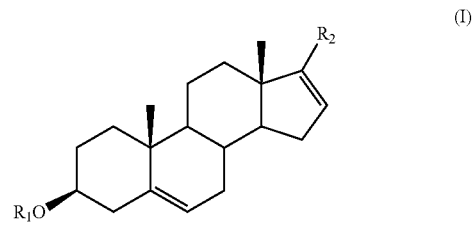

or a pharmaceutically acceptable salt thereof, wherein $R_1$ is H and $R_2$ is benzimidazole.

2. The method of claim 1, wherein the AR-V7 expression has been detected in a sample selected from the group consisting of whole blood, serum, plasma, tissue, semen, cell, biopsy, mucous, feces, bone, teeth, nasal or throat or cheek swab, urine, skin, tears, organ biopsy, tumor biopsy or tumor tissue, circulating tumor cells, exosomes from a primary tumor or from metastatic tissue, and combinations thereof.

3. The method of claim 2, wherein the sample is a processed whole blood sample.

4. The method of claim 2, wherein the sample is a tumor tissue sample or tumor biopsy sample.

5. The method of claim 2, wherein the sample is a sample enriched for circulating tumor cells.

6. The method of claim 2, where the sample is a sample enriched for circulating DNA.

7. The method of claim 1, wherein the AR-V7 is expressed in circulating tumor cells (CTC).

8. The method of claim 1, wherein the prostate cancer is resistant to castration.

9. The method of claim 1, wherein the subject has undergone chemical castration or surgical castration.

10. The method of claim 1, wherein the prostate cancer is resistant to an androgen receptor antagonist.

11. The method of claim 10, wherein the androgen receptor antagonist is enzalutamide or bicalutamide or ARN-509.

12. The method of claim 1, wherein the prostate cancer is resistant to a CYP17 inhibitor.

13. The method of claim 12, wherein the CYP17 inhibitor is abiraterone.

14. The method of claim 1, wherein the cancer is resistant to a taxane.

15. The method of claim 14, wherein the taxane is docetaxel or cabazitaxel.

16. The method of claim 1, wherein the prostate cancer is androgen dependent.

17. The method of claim 1, wherein the step of administering comprises administering a daily dosage within a range of about 0.03 to about 60 mg/kg body weight.

18. The method of claim 1, wherein the step of administering comprises administering about 2,550 mg daily.

19. The method of claim 1, wherein the step of administering comprises administering at least one unit dosage form comprising from about 90 mg to about 3,500 mg active ingredient.

20. The method of claim 1, wherein the step of administering comprises administering orally.

21. The method of claim 1, wherein the step of administering comprises administering for a period of time sufficient that the subject shows a response to the therapy, which response is or comprises a change of clinical or medical presentation, prognosis, symptoms, diagnostic indices, features, survival or outcomes.

22. The method of claim 21, wherein the response is or comprises one or more of: PSA decline relative to pretreatment level, pain improvement, quality of life improvement as assessed by direct patient measure, change in CTC count, change in CTC characterization, PSA progression free survival, radiographic progression free survival, and induction of immunity to tumor antigens.

23. The method of claim 1, wherein the step of administering comprises administering for a period of time sufficient that the subject shows one or more of:
  decrease in numbers of CTC, increase in apoptotic CTC, decrease in PSA or reduction in PSA doubling time, increase in PSMA expression as determined by imaging modalities such as radio labeled ligands of PSMA or antibodies than bind PSMA, reduction in tumor 18F-DHT-PET signal, a tissue biopsy test that differentiates indolent from aggressive disease in formalin-fixed, paraffin-embedded tissue samples, inhibition of androgen receptor tagging, and removal of androgen receptor from cells.

24. The method of claim 21, wherein the PSA decline is a maximal reduction in PSA level of at least 50%.

25. The method of claim 21, wherein the radiographic progression free survival is evaluated using a radiolabeled ligand.

26. The method of claim 25, wherein the radiolabeled ligand is a radiolabeled ligand of prostate specific membrane antigen (PSMA).

27. The method of claim 1, wherein the step of administering comprises administering to a population of subjects with prostate cancer and expressing AR-V7 and is effective to achieve one or more of: PSA decline relative to pretreatment level, pain improvement, quality of life improvement as assessed by direct patient measure, change in CTC count, change in CTC characterization, PSA progression free survival, radiographic progression free survival, and induction of immunity to tumor antigens in the population.

28. The method of claim 21, wherein the survival is overall survival.

29. The method of claim 1, wherein the AR-V7 has been detected using reverse transcription and polymerase chain reaction ("RT-PCR") with PCR primers designed to specifically amplify transcript sequences that are known in the $NH_2$ terminal (5' primers) and within the AR-V7 form of the AR protein.

30. The method of claim 1, wherein the step of administering comprises administering for a period of time sufficient that the subject shows one or more of:
  loss of androgen (testosterone or DHT), up or down regulation of AR specific gene expression (i.e. protein analysis), immune reactivity (detection of antibody or specific immune cells), PSA levels, or broadly, tumor shrinkage.

* * * * *